(12) United States Patent
Jin et al.

(10) Patent No.: US 10,262,885 B2
(45) Date of Patent: Apr. 16, 2019

(54) MULTIFUNCTION WAFER AND FILM FRAME HANDLING SYSTEM

(71) Applicant: SEMICONDUCTOR TECHNOLOGIES & INSTRUMENTS PTE LTD, Singapore (SG)

(72) Inventors: Jian Ping Jin, Singapore (SG); Leng Kheam Lee, Singapore (SG)

(73) Assignee: SEMICONDUCTOR TECHNOLOGIES & INSTRUMENTS PTE LTD, Singapore (SG)

(*) Notice: Subject to any disclaimer, the term of this patent is extended or adjusted under 35 U.S.C. 154(b) by 914 days.

(21) Appl. No.: 14/424,415

(22) PCT Filed: Sep. 2, 2013

(86) PCT No.: PCT/SG2013/000383
§ 371 (c)(1),
(2) Date: Feb. 26, 2015

(87) PCT Pub. No.: WO2014/035348
PCT Pub. Date: Mar. 6, 2014

(65) Prior Publication Data
US 2015/0214085 A1 Jul. 30, 2015

Related U.S. Application Data

(60) Provisional application No. 61/696,051, filed on Aug. 31, 2012.

(51) Int. Cl.
*H01L 21/30* (2006.01)
*H01L 21/68* (2006.01)
(Continued)

(52) U.S. Cl.
CPC ......... *H01L 21/681* (2013.01); *B25J 11/0095* (2013.01); *B25J 15/0616* (2013.01);
(Continued)

(58) Field of Classification Search
None
See application file for complete search history.

(56) References Cited

U.S. PATENT DOCUMENTS

| 5,770,095 A | 6/1998 | Sasaki et al. |
| 6,120,360 A | 9/2000 | Ball et al. |

(Continued)

FOREIGN PATENT DOCUMENTS

| EP | 2485244 A1 | 8/2012 |
| JP | 2000-124298 A | 4/2000 |

(Continued)

OTHER PUBLICATIONS

International Search Report dated Nov. 25, 2013 on related Application No. PCT/SG2013/000383, filed Sep. 2, 2013.

*Primary Examiner* — Cory W Eskridge
(74) *Attorney, Agent, or Firm* — Horizon IP Pte Ltd.

(57) ABSTRACT

A multifunction wafer and film frame handling system includes a wafer table assembly having a wafer table providing an ultra-planar wafer table surface configured for carrying a wafer or a film frame, and at least one of: a flattening apparatus configured for automatically applying a downward force to portions of a warped or non-planar wafer in a direction normal to the wafer table surface; a displacement limitation apparatus configured for automatically constraining or preventing uncontrolled lateral motion of a wafer relative to the wafer table surface after cessation of an applied negative pressure and application of a positive pressure to the underside of the wafer via the wafer table; and a rotational misalignment compensation apparatus con- (Continued)

figured for automatically compensating for a rotational misalignment of a wafer mounted on a film frame.

18 Claims, 38 Drawing Sheets

(51) Int. Cl.
*H01L 21/683* (2006.01)
*B25J 11/00* (2006.01)
*B25J 15/06* (2006.01)
*H01L 21/677* (2006.01)
*G01B 11/27* (2006.01)
*G01N 21/95* (2006.01)
*H01L 21/687* (2006.01)
*H01L 21/67* (2006.01)

(52) U.S. Cl.
CPC ....... *B25J 15/0658* (2013.01); *B25J 15/0666* (2013.01); *G01B 11/27* (2013.01); *G01N 21/9501* (2013.01); *H01L 21/67144* (2013.01); *H01L 21/67706* (2013.01); *H01L 21/6838* (2013.01); *H01L 21/68757* (2013.01); *G01N 2201/025* (2013.01); *Y10T 29/49826* (2015.01)

(56) References Cited

U.S. PATENT DOCUMENTS

| | | |
|---|---|---|
| 2001/0024878 A1 | 9/2001 | Nakamura |
| 2002/0157246 A1* | 10/2002 | Ogimoto ............ H05K 13/0069 29/832 |
| 2002/0192059 A1 | 12/2002 | Foster, Jr. et al. |
| 2003/0211813 A1 | 11/2003 | Kassir |
| 2006/0222481 A1 | 10/2006 | Foree |
| 2007/0118246 A1 | 5/2007 | Suzuki |
| 2009/0175705 A1 | 7/2009 | Nakao |
| 2010/0013169 A1* | 1/2010 | Monteen ............. H01L 21/6838 279/3 |
| 2011/0076118 A1 | 3/2011 | Kurita et al. |
| 2011/0241298 A1 | 10/2011 | Vodanovic et al. |

FOREIGN PATENT DOCUMENTS

| | | |
|---|---|---|
| JP | 2001-313326 A | 11/2001 |
| JP | 2007-142267 A | 6/2007 |
| JP | 2009-107097 A | 5/2009 |
| WO | 2004/073029 A2 | 8/2004 |
| WO | 2005/092564 A1 | 10/2005 |
| WO | 2011/120174 A1 | 10/2011 |

* cited by examiner

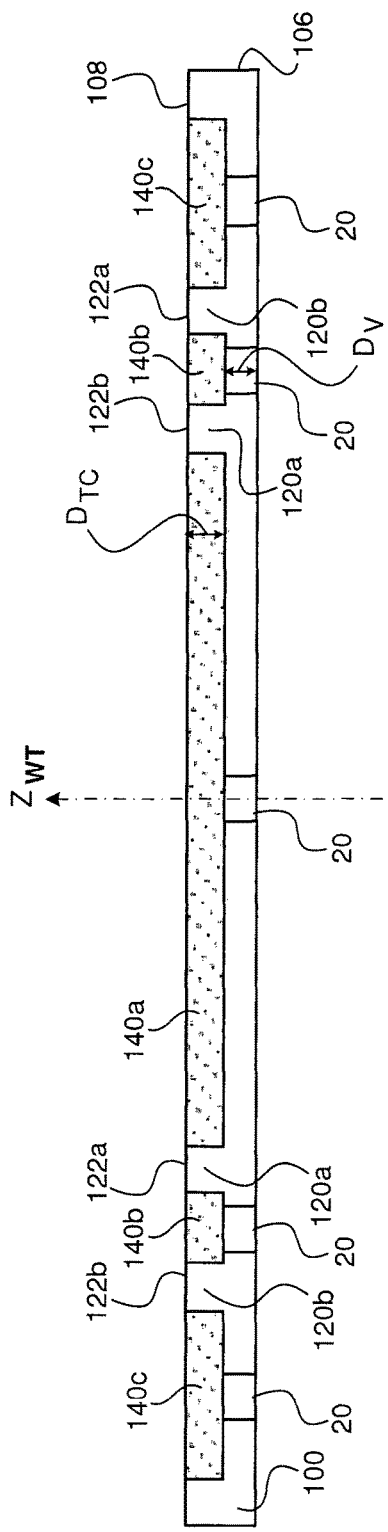
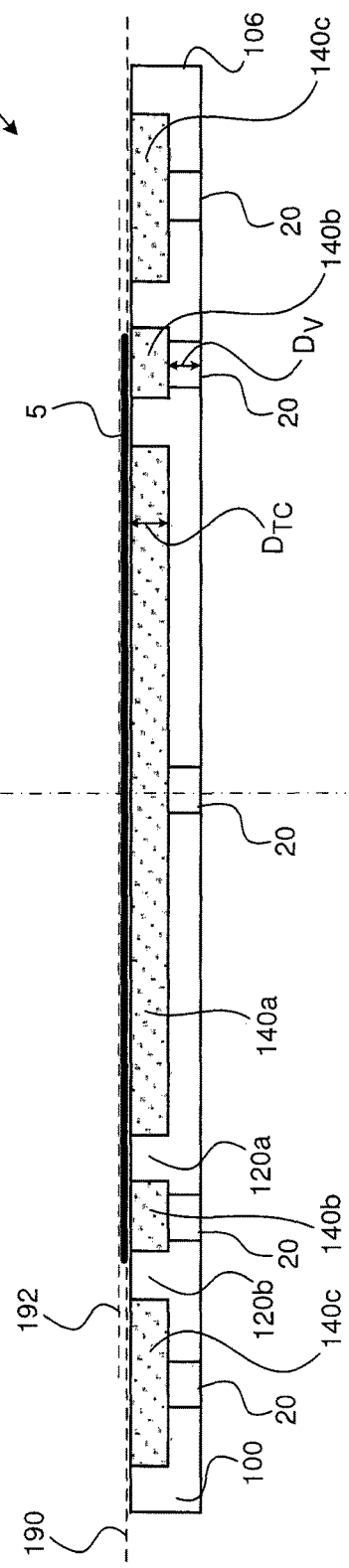
FIG. 5C
FIG. 5D

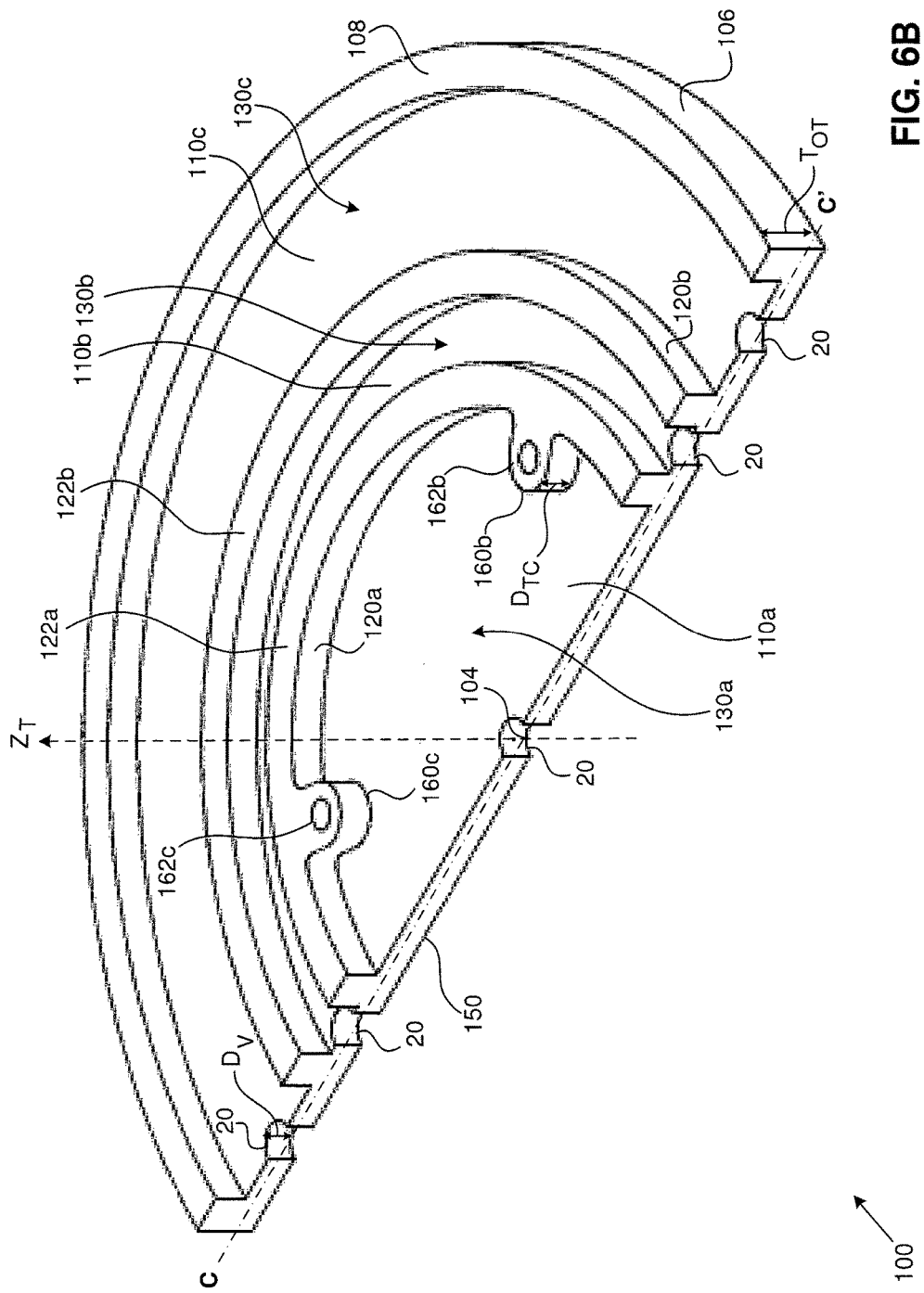

MULTIFUNCTION WAFER AND FILM FRAME HANDLING SYSTEM

CROSS-REFERENCE TO RELATED APPLICATIONS

This application is a U.S. national stage entry under 35 U.S.C. § 371 of PCT International Patent Application No. PCT/SG2013/000383, filed Sep. 2, 2013, which claims the benefit of U.S. Provisional Patent Application No. 61/696,051, filed Aug. 31, 2012, the contents of which are incorporated herein by reference in their entirety.

TECHNICAL FIELD

Aspects of the present disclosure are directed to a system and method capable of handling both wafers and wafers mounted on film frames in a manner that facilitates accurate, high throughput inspection processes. Particular embodiments are configured for automatically (a) remediating insufficient vacuum retention of wafers upon a wafer table surface due to wafer warpage or non-planarity; (b) preventing uncontrolled lateral displacement of wafers along the wafer table surface due to vacuum force cessation and/or air purge application; and/or (c) correcting or compensating for rotational misalignment of wafers carried by film frames. Embodiments can also provide a single ultra-planar porous wafer table configured for handling both wafers and film frames.

BACKGROUND

Semiconductor wafer processing operations involve the performance of various types of processing steps or sequences upon a semiconductor wafer upon which a number of die (e.g., a large or very large number of die) reside. The geometrical dimensions, linewidths, or feature sizes of devices, circuits, or structures on each die are typically very small, for example, micron, submicron, or nanometer scale. Any given die includes a large number of integrated circuits or circuit structures that are fabricated, processed, and/or patterned on a layer-by-layer basis, for instance, by way of processing steps performed upon wafers sitting on planar wafer surfaces, such that the dies carried by the wafer are collectively subjected to the processing steps.

A wide variety of semiconductor device processing operations involve a number of handling systems that perform wafer or film frame handling operations which involve securely and selectively carrying (e.g., transporting, moving, displacing, or conveying) wafers or wafers mounted on film frames (hereafter referred to as "film frame" for brevity) from one position, location, or destination to another, and/or maintaining wafers or film frames in particular positions during wafer or film frame processing operations. For instance, prior to the initiation of an optical inspection process, a handling system must retrieve a wafer or a film frame from a wafer or film frame source such as a wafer cassette, and transfer the wafer or film frame to the wafer table. The wafer table must establish secure retention of the wafer or film frame to its surface prior to the initiation of the inspection process, and must release the wafer or film frame from its surface after the inspection process is complete. Once the inspection process is complete, a handling system must retrieve the wafer or film frame from the wafer table, and transfer the wafer or film frame to a next destination, such as a wafer or film frame cassette or another processing system.

Various types of wafer handling systems and film frame handling systems are known in the art. Such handling systems can include one or more mechanical or robotic arms configured for performing wafer handling operations which involve the transfer of wafers to and the retrieval of wafers from a wafer table; or performing film frame handling operations which involve the transfer of film frames to and the retrieval of film frames from a wafer table. Each robotic arm includes an associated end effector which is configured for retrieving, picking up, holding, transferring, and releasing a wafer or a film frame by way of the application and cessation of vacuum force relative to portions of the wafer or film frame, in a manner understood by one of ordinary skill in the relevant art.

A wafer table itself can be viewed or defined as a type of handling system, which must reliably, securely, and selectively position and hold a wafer or film frame on a wafer table surface while displacing the wafer or film frame relative to elements of a processing system, such as one or more light sources and one or more image capture devices corresponding to an optical inspection system. The structure of a wafer table can significantly impact whether an inspection system can achieve a high average inspection throughput, as further detailed below. Furthermore, the structure of a wafer table, in association with the physical characteristics wafers and the physical characteristics of film frames, greatly impacts the likelihood that an optical inspection process can reliably generate accurate inspection results.

With respect to the generation of accurate inspection results, during an optical inspection process, a wafer or a film frame must be securely retained upon the wafer table. Additionally, the wafer table must dispose and maintain the upper or top surface of the wafer or film frame in a common inspection plane, such that the surface areas of all wafer die, or as many wafer die as possible, collectively reside in this common plane, with minimum or negligible deviation therefrom. More particularly, the proper or accurate optical inspection of die at very high magnification requires a wafer table to be very flat, preferably with a planarity having a margin of error of less than ⅓ of the depth of focus of the image capture device. If the depth of focus of an image capture device is, for instance, 20 µm, a corresponding wafer table planarity error cannot exceed 6 µm.

For handling die of very small size (eg. 0.5×0.5 mm or smaller) and/or thickness (50 µm or less—e.g., carried by a very thin and/or flexible wafer or substrate), this planarity requirement becomes even more critical. For wafers that are very thin, it is important for the wafer table to be ultra-planar, otherwise it is easy for one or more die on the wafer or film frame to become positioned out of the depth of focus. One of ordinary skill in the art will recognize that the smaller the die, the higher the magnification required, and hence the narrower the band of depth of focus in which the inspection plane must lie.

With such planarity outlined aforesaid, a wafer placed on the wafer table will lie flatly on the wafer table surface, the wafer squeezing out substantially all the air beneath it. The difference in atmospheric pressure between the top and bottom surface of the wafer when the wafer is disposed upon the wafer table results in a large force applied against the top surface of the wafer due to atmospheric pressure, holding the wafer down strongly or reasonably strongly upon the wafer table. As pressure is a function of surface area, the larger the size of the wafer, the greater the force applied downwards on the wafer. This is commonly referred to as the "inherent suction force" or "natural suction force" on the wafer. The flatter the wafer table surface, the greater the natural suction force, up to the limit defined by the finite surface of the wafer. However, the strength of such suction force depends on how flat the wafer table surface is. Some wafer tables are not that flat and may have other grooves or holes on its surface resulting in reduced suction force. As the wafer table will be repeatedly accelerated over short distances during inspection of each die, and a high vacuum force is often applied through the wafer table to the wafer table surface to the underside of the wafer to ensure that the wafer remains as planar as possible and does not move during inspection; this is notwithstanding the presence of such natural suction force.

Various types of wafer table structures have been developed in attempts to securely hold wafers or film frames during wafer or film frame inspection operations, and reliably maintain a maximum number of die in a common plane during inspection operations. However not one design exists that will allow the wafer handling system to handle both wafers and sawn wafers mounted on film frames without one or more of the problems described below. A brief description will be made of each type of existing design and their associated problems.

Several types of wafer chucks have been or are currently in use. In the past, wafers were smaller (e.g., 4, 6, or 8 inches) and significantly thicker (particularly in relation to their overall surface areas, e.g., on a wafer thickness normalized to wafer surface area basis), and each die size was larger. Present-day wafer sizes are typically 12 or 16 inches, yet the thickness of these processed wafers have been decreasing in relation to their increasing size (for instance, thicknesses of 0.70-1.0 mm for 12-inch wafers prior to thinning/backgrinding/backlapping, and 50-150 µm following thinning/backlapping are common), and die sizes (e.g., 0.5-1.0 mm square), respectively. Standard wafer sizes can be expected to further increase over time. Additionally, thinner and thinner wafers can be expected to be processed each year in response to the increasing demands and requirements of electronics and mobile phone manufacturers for thinner die/thinner components to fit into slim-built electronic devices (e.g., flat screen televisions, mobile phones, notebook computers, tablet computers, etc.). As will be explained, these factors contribute to the increasing deficiencies of current designs of wafer table to handle both wafers and film frames.

Historically, and even presently, many wafer chucks have been made of a metal such as steel. Such metal wafer chucks are inlaid with a network of grooves, usually circular grooves that are intersected by grooves radiating linearly from a central location. Through such grooves, vacuum force can be applied to the underside of the wafer, which interfaces with the wafer table surface, in order to facilitate secure retention of the wafer against the wafer table surface. In many wafer table designs, such grooves are arranged in concentric circles of increasing size. Depending on the size of the wafer, one or more grooves would be covered by a wafer when the wafer is disposed upon the wafer table surface. Vacuum can be activated through the grooves covered by the wafer to hold the wafer down during processing operations, such as wafer inspection operations. After inspection, the vacuum is deactivated and ejector pins are deployed to lift the wafer off of the wafer table surface, such that the wafer can be retrieved or removed by an end effector. As there are linear grooves radiating from the centre of the metal wafer table surface, once the vacuum is deactivated, the residual suction force associated with application of the vacuum force to the underside of the wafer is quickly dissipated. Thicker wafers are more amenable to application of significant force applied through the ejector pins to lift the wafer (against any residual suction force, if any) without breaking.

As indicated above, increasingly wafers manufactured today are thinner or much thinner than before (e.g., present wafer thicknesses can be as thin as 50 µm), and each die thereon is also increasingly smaller in size (e.g., 0.5 mm square) than in the past. Technological progression results in smaller die sizes and thinner die, which pose a problem for handling wafers by way of existing wafer table designs. Very often, backlapped/thinned or sawn wafers (hereafter simply "sawn wafers") having die that are very small in size and/or which are very thin are mounted on film frames for processing. Conventional metal wafer tables are not suitable for use with film frames having sawn wafers mounted thereto for a number of reasons.

Bearing in mind that inspection of die involves very high magnification, the higher the magnification, the narrower an acceptable depth of focus band, range, variance, or tolerance will be for accurate inspection. Die that are not in the same plane are likely to be out of the depth of focus of an image capture device. As indicated above, the depth of focus of a modern image capture device for wafer inspection typically ranges from 20-70 µm or smaller, depending on the magnification. The presence of grooves on the wafer table surface presents problems particularly during the inspection of sawn wafers mounted on film frames (with small die sizes) on such systems.

The presence of grooves results in the sawn wafers with small die sizes not sitting properly or uniformly on the wafer table surface. More particularly, in regions where there are grooves (and there can be many), the film frame's film can slightly sag into the grooves, resulting in the whole wafer surface lacking collective or common planarity across all die, which is critical for optical inspection operations. This lack of planarity becomes more pronounced for small or very small die of sawn wafers. Furthermore, the presence of a groove can cause die to be displaced at an angle relative to a common die inspection plane, or cause the die to sag and sit at one or more different and lower planes. Furthermore, light shining on tilted die which have sagged into grooves will reflect light away from the image capture device, such that the capture of an image corresponding to a tilted die will not contain or convey precise details and/or features of one or more regions of interest on the die. This will adversely affect the quality of images captured during inspection, which can lead to inaccurate inspection results.

Several prior approaches have attempted to address the aforementioned problems. For instance, in one approach a metal wafer table support includes a network of grooves. A flat metal plate is placed on top of the network of grooves. The metal plate includes many small or very small vacuum holes that allow vacuum to be applied through the perforations against a wafer or sawn wafer. Depending on the size of wafer under consideration, an appropriate pattern or number of corresponding grooves will be activated. While multiple small or very small vacuum holes can increase the likelihood that die can be collectively maintained in the same inspection plane, collective die planarity problems are still not effectively or completely eliminated due to continuing technological evolution that results in smaller and smaller die sizes and decreasing die thicknesses over time Such designs also include multiple sets of ejector pin triplets corresponding to different wafer sizes, i.e., multiple distinct sets of three ejector pins corresponding to multiple standard wafer sizes that the wafer table is capable of carrying. The presence of numerous holes for ejector pins can also present, and quite possibly worsen, collective die planarity problems when inspecting die carried on film frames, for reasons analogous to those set forth above.

Some manufacturers use wafer table conversion kits, in which a metal wafer table with grooves is used for handling whole wafers, and a metal wafer table cover with many very small openings is used for film frame handling. Unfortunately, conversion kits require inspection system downtime due to the fact that conversion from one type of wafer table to another, and post-conversion wafer table calibration, is time consuming and done manually. Such downtime adversely affects average system throughput (e.g., overall or average throughput with respect to both wafer and film frame inspection operations considered in sequence or together), and hence inspection systems that require wafer table conversion kits are undesirable.

Other wafer table designs, such as described in U.S. Pat. No. 6,513,796, involve a wafer table receptacle that allows for different central wafer table inserts depending on whether wafers or film frames are being processed. For wafer inspection, the insert is typically a metal plate with annular rings having vacuum holes for activation of vacuum. For film frames, the insert is a metal plate having many fine holes for vacuum activation, which can still give rise to collective die nonplanarity as described above.

Still other wafer table designs, such as disclosed in U.S. Patent Application Publication 2007/0063453, utilize a wafer table receptacle having a plate type insert consisting of a porous material in which distinct regions are defined by annular rings made of a thin film material. Typically, such wafer table designs are complex in construct and involves a delicate and complex manufacturing process, and hence difficult, time consuming, or costly to manufacture. Moreover, such designs can utilize metal annular rings to facilitate regional vacuum force control across the wafer table surface in accordance with wafer size. Metal annular rings can require undesirably long planarization times, or damage a polishing device that is used to polish the wafer table surface when planarizing the wafer table surface. Furthermore, metal rings can give rise to nonplanarity due to differential material polishing characteristics across the wafer table surface, and therefore metal annular rings are unsuitable for modern optical inspection processes (e.g., particularly involving sawn wafers mounted on film frames).

Unfortunately, prior wafer table designs are (a) unnecessarily structurally complex; (b) difficult, expensive, or time consuming to fabricate; and/or (c) unsuitable for various types of wafer processing operations (e.g., die inspection operations, particularly when die are carried by a film frame) as a result of insufficient wafer table surface planar uniformity in view of technological evolution that continues to give rise to smaller and smaller wafer die sizes and/or progressively decreasing wafer thicknesses. A need clearly exists for a wafer table structure and an associated wafer table manufacturing technique that that will enable the wafer table to handle both wafers and sawn wafers and which overcomes one or more of the foregoing problems or drawbacks.

In addition to the above aspects of wafer table design that can impact the accuracy of wafer and film frame inspection as well as average inspection throughput, multiple other types of wafer or film frame handling problems can exist, which can adversely affect wafer or film frame inspection operations. Such problems and prior art solutions thereto are detailed hereafter.

Wafer—Wafer Table Retention Failure Due to Wafer Non-Planarity

One type of wafer handling problem arises as a result of wafer non-planarity or warpage. This problem arises from a number of factors, including (a) the increasing size of wafers being manufactured; (b) the decreasing thickness of wafers being handled; and (c) the manner in which wafers are handled or stored prior to and after processing. Prior to and after processing such as optical inspection, wafers are held at their edges in a cassette. Given the increasing diameter and thinness of wafers, and the manner in which wafers are held in the cassette, sagging of a wafer near its center, or wafer warpage, is not uncommon. In addition, during backlapping processes to thin the wafer to required dimensions, the backlapping process can cause the wafer to have a reverse warp, although this problem is less common.

When a non-planar wafer rests upon a wafer table surface, a vacuum force applied through the wafer table surface which is intended to securely hold the entire bottom surface of the wafer against the wafer table surface will only weakly hold a portion of the bottom wafer surface. As the other portions of the wafer will reside above the wafer table surface and vacuum that is applied through the wafer table will leak and any residual vacuum force applied would be very weak. In such a situation, the wafer will not be held down securely and furthermore such a warped wafer 10 cannot, typically, be reliably inspected or tested.

Prior approaches directed to ensuring that the entire surface area of a wafer is securely held upon a wafer table surface involve automatically halting inspection system operation when an insufficient vacuum retention force (or vacuum leakage that is below a minimum vacuum retention threshold value) is detected, until an inspection system operator or user manually intervenes. To solve the problem, the inspection system operator manually presses the wafer against the wafer table surface, until vacuum force applied through the wafer table surface engages the wafer's entire surface area and securely retains the wafer against the wafer table surface. Such automatic halting of inspection system operation as a result of insufficient vacuum retention of the wafer upon the wafer table surface can only be resumed after user intervention to manually correct the problem. Such downtime adversely impacts system throughput.

Unpredictable/Uncontrollable Lateral Wafer Displacement Following Vacuum Force Cessation Typically, for inspection of wafers, the following steps occur to place a wafer on a wafer table: (a) the wafer is retrieved from a cassette and sent to a wafer (pre)aligner; (b) the wafer aligner serves to properly orientate the wafer for inspection; (c) after wafer alignment is completed, an end effector conveys the wafer to a predetermined position where its center coincides with the center of the wafer table; (d) ejector pins are activated to receive the wafer; (e) the end effector lowers the wafer onto the ejector pins before retracting; and (f) the ejector pins then lower the wafer onto the wafer table for inspection while vacuum is applied to hold the wafer down for inspection.

When inspection is completed, (a) vacuum is deactivated; (b) the wafer is lifted up by the ejector pins; (c) the end effector slides beneath the wafer and lifts up the wafer; and (d) the end effector transfers the inspected wafer back to a cassette, and puts the wafer into the cassette.

It is pertinent to note that to enable the effector to place the wafer into the cassette, it is important that the wafer remains in a predetermined position, and has not changed its position, relative to the end effector from the time it was placed on the wafer table. This means that the wafer must not move from the moment it is placed on the table. If the wafer is significantly or seriously out of position relative to the end effector, there is a risk that the wafer can drop during conveyance, or be damaged when the end effector tries to push the off-positioned wafer into the cassette. To prevent these mishaps, when the wafer is finally picked up by the effector after inspection, the wafer should, relative to the end effector, be in the same position as it was when the wafer was placed on the wafer table prior to the start of inspection. To hold the wafer in its position upon placement by the end effector, vacuum through the grooves is activated in addition to the natural suction that results when the whole or parts of the wafer sits flatly on the wafer table.

In certain situations, after the application of vacuum force or negative pressure to the underside of a wafer has ceased, the wafer can slide laterally along the wafer table surface as a consequence of subsequent events or process steps. Unpredictable lateral motion of the wafer causes the wafer to move or translate to a different position from the position at which the wafer was originally placed upon the wafer table prior to or at the start of inspection (i.e., the wafer laterally slides away from a reference wafer table position relative to which the effector deposits and retrieves the wafer). Consequently, when the effector retrieves a wafer that is unreliably or unpredictably mispositioned as a result of such lateral motion, there is a risk that the wafer will be dropped or damaged when the effector attempts to load the out-of-position wafer 10 back into a wafer cassette.

Prior approaches for managing unintended lateral wafer displacement relative to a wafer table surface following vacuum force cessation involve manual intervention, which again results in the interruption of inspection or test system operations, adversely impacting production throughput.

Wafer—Film Frame Rotational Misalignment

At a particular stage of wafer manufacturing, wafers may be mounted on film frames. For instance, when wafers are to be sawn, they are usually mounted on film frames. After being sawn, the sawn wafers on film frame are further inspected for cosmetic and/or other types of defects. FIG. 1A is a schematic illustration of a wafer 10 mounted on a film frame 30, which carries the wafer 10 by way of a thin material layer or film 32 that typically includes an adhesive or tacky side to which the wafer 10 is mounted, in a manner readily understood by one of ordinary skill in the art. The wafer 10 includes a number of die 12, which are separated or delineated from each other by horizontal gridlines 6 and vertical gridlines 8 that are produced or which become evident during manufacture. Such horizontal and vertical gridlines 6, 8 correspond to or delineate horizontal and vertical sides 11, 16 of the die, respectively. One of ordinary skill in the art will understand that a wafer 10 typically includes at least one reference feature 11, for instance, a notch or a straight portion or "flat" segment on an otherwise circular periphery, to facilitate wafer alignment operations. One or ordinary skill in the relevant art will further understand that the film frame 30 includes a number of registration or alignment features 34a-b to facilitate film frame alignment operations. The film frame 30 can also include a number of other reference features, such as "flats" 35a-d.

With respect to optical inspection, die 12 on the wafer 10 are automatically inspected or examined in accordance with inspection criteria that facilitate the identification of cosmetic or other (e.g., structural) defects on the die 12. Die 12 which meet the inspection criteria, as well as die which fail to meet the inspection criteria, can be tracked or categorized in accordance with "pass" or "fail" designations, respectively. Die 12 that successfully meet all inspection criteria are suitable for further processing or incorporation into an integrated circuit package, whereas die 12 that fail to meet all inspection criteria can be (a) discarded; (b) analyzed for determining failure cause(s) and preventing future failures; or (c) in certain situations, reworked/reprocessed.

Optical inspection involves directing illumination at individual die 12 or an array of die 12; capturing illumination reflected from the die 12 using an image capture device and generating image data corresponding to the die 12; and performing image processing operations upon the image data to determine whether one or more types of defects are present on the die 12. Optical inspection is typically performed "on-the-fly" while the wafer 12 is in motion, such that the die 12 carried by the wafer 12 are continuously moving relative to the image capture device during image capture operations.

Inspection of an entire wafer 10 requires the generation of an inspection result (e.g., a pass/fail result) corresponding to each die 12 on the wafer 10. Before an inspection result corresponding to any given die 12 can be generated, the entire surface area of the die 12 must first be completely captured. In other words, complete inspection of any given die 12 requires that the die's entire surface area must first be completely captured by the image capture device, and image data corresponding to the entire surface area of each of the die 12 must be generated and processed. If image data corresponding to the die's entire surface area has not been generated, image processing operations corresponding to the die 12 cannot be completed, and an inspection result cannot be generated, until the capture of a set of images encompassing the entire surface area of the die 12, or an "entire-die image," has occurred. Therefore, if image data corresponding to the entire surface area of a die 12, or entire-die image data, has not been generated, the generation of an inspection result for the die 12 is unnecessarily delayed, which adversely affects inspection process throughput.

The greater the number of image capture operations required to completely capture the entire die image for image processing, the lower the throughput for inspection. It stands to reason that in order to maximize inspection process throughput, every die's entire surface area should preferably be captured in as few images as possible.

Error in the orientation of the wafer 10 can arise during the mounting of the wafer 10 on a film frame 30. In general, the error in wafer mounting relates to a wafer flat or notch 11 not aligning properly with respect to a given film frame reference feature, such as a film frame flat 35a. FIG. 1B is a schematic illustration of a wafer 10 that is rotationally misaligned relative to a film frame 30 that carries the wafer 10. It can be clearly seen that the wafer 10 shown in FIG. 1B bears a significantly different rotational orientation relative to its film frame 30 than the wafer 10 shown in FIG. 1A bears in relation to its film frame 30. More particularly, it can be seen from FIG. 1B that with respect to a horizontal reference axis 36 and/or a vertical axis 38 defined parallel to and perpendicular to a first film frame flat 35a, respectively, a pair of reference horizontal and vertical wafer gridlines 6, 8 are rotated, angularly offset, or misaligned by an angle θ compared to the wafer 10 shown in FIG. 1A.

In other words, for the wafer 10 shown in FIG. 1A, the angle θ, which indicates an angular extent to which a wafer gridline 6, 8 has been rotated away from a reference axis 36, 38 having a predetermined orientation relative to the first film frame flat 35a, is approximately zero. For the wafer 10 shown in FIG. 1B, the wafer-to-film frame misalignment angle is θ non-zero. As wafer size increases, and particularly for larger wafer sizes (e.g., 12 inches or greater), the rotational misalignment of a mounted wafer 10 vis-à-vis the film frame 30 typically creates problems during inspection of the wafer 10 mounted thereon, as further detailed hereafter.

During the capture of a given image of a die 12, an inspection system's image capture device can capture illumination reflected from only those portions of the die's surface area which are disposed within the image capture device field of view (FOV). Portions of the die's surface area which fall outside of the image capture device FOV cannot be captured as part of this image, and must be captured as part of another image. As indicated above, the maximization of inspection process throughput requires that the entire surface area of every die 12 on the wafer 10 be captured in as few images as possible. When multiple image capture operations are required to generate image data corresponding to a die's entire surface area, the generation of an inspection result for the die 12 is delayed, which adversely affects throughput. Each die 12 on the wafer 10 must therefore be properly aligned relative to the image capture device FOV in order minimize the number of image capture operations required to generate entire-die image data for all die 12 on the wafer 10, in order to maximize inspection process throughput.

Proper alignment of the die 12 relative to the image capture device FOV can be defined as a situation in which any rotational or angular misalignment of the die 12 relative to the image capture device FOV is sufficiently small, minimal, or negligible that the die's entire surface area will fall within the FOV. FIG. 2A is a schematic illustration of a die 12 that is properly positioned or aligned relative to an image capture device field of view (FOV) 50. As clearly indicated in FIG. 2A, under conditions of proper die alignment relative to the FOV 50, a horizontal border or side 14 of the die 12 is aligned substantially parallel to an FOV horizontal axis $X_I$, and a vertical border or side 16 of the die 12 is aligned substantially parallel to an FOV vertical axis $Y_I$. Consequently, the entire surface area of such a die 12 falls within the FOV 50, and the entire surface area of the die 12 can be captured by the image capture device in a single image capture event, operation, or "snap."

FIG. 2B is a schematic illustration of a die 12 that is improperly positioned or which is misaligned relative to an image capture device FOV 50. FIG. 2B clearly indicates that the horizontal and vertical sides of the die 14, 16 are rotated or angularly offset from the FOV horizontal axis $X_I$ and the FOV vertical axis $Y_I$, respectively, and portions of the die's surface area fall outside of the FOV 50. Because of such misalignment of the die 12 relative to the FOV 50, the generation of image data corresponding to the entire surface area of the die 12 requires the capture of multiple images that capture different portions of the die 12, resulting in reduced inspection process throughput. More particularly, as shown in FIG. 2C, up to four images may be required to capture the entire surface area of such a rotationally misaligned die 12, depending upon the extent of the die's misalignment relative to the FOV.

When film frames are handled, typically a mechanical film frame registration procedure must take place. Usually, the film frame registration procedure occurs when the film frame is placed on the wafer table. In some systems, such as that described in Singapore Patent Application No. 201103524-3, entitled "System and Method for Handling and Aligning Component Panes such as Wafers and Film Frames," filed on 12 May 2011, a mechanical film frame registration can take place before placement of the film frame on the wafer table, such as when an end effector that carries the film frame causes a set of film frame alignment features 34a-b to engage with film frame registration elements or structures prior to placement of the film frame on the wafer table.

A mechanical film frame registration procedure involves a certain amount of handling time. However, the film frame registration procedure typically ensures that the film frame 30 is properly aligned or registered with respect to the image capture device FOV. However this assumes that the wafer was properly mounted on the film frame in the first place, which is not always the case. Where the wafer mounted on the film frame has a rotational misalignment, it can give rise to problems and delays in inspection, adversely affecting throughput as elaborated upon below.

The film frame registration procedure occurs by way of mating engagement between film frame registration features 34a-b and one or more film frame registration elements, which are conventionally carried by a wafer table assembly. After a film frame 30 has been registered, die 12 on the wafer 10 mounted to the film frame 30 are expected to be properly aligned with respect to the image capture device FOV. However, if more than a slight or minimal amount of rotational or angular misorientation of the wafer 10 mounted to the film frame 30 exists, the die 12 will not be properly aligned relative to the image capture device FOV. It therefore stands to reason that the extent of any rotational misalignment of a wafer 10 that occurs during the mounting of the wafer 10 to a film frame 30 can adversely affect the number of images required to capture the entire surface area of each die 12 on the wafer 12, and hence the extent of any rotational misalignment of the wafer 10 relative to the film frame 30 can adversely affect inspection throughput.

Proper alignment of the wafer 10 relative to its film frame 30 ensures proper alignment of the die 12 relative to the image capture device FOV 50. Proper alignment of the wafer 10 relative to its film frame 30 can be defined as a situation in which one or more wafer gridlines 6, 8 have a standard predetermined alignment relative to one or more film frame structural features such as film frame flats 35a-d and/or the image capture device FOV, such that the each die 12 is positioned relative to the image capture device FOV in the manner shown in FIG. 2A (i.e., each die's horizontal and vertical sides 14, 16, with the FOV horizontal and vertical axes $X_I$ and $Y_I$). Such alignment of the wafer 10 relative to the film frame 30 minimizes the number of image capture operations required to capture each die's entire surface area, thereby maximizing inspection process throughput.

To further illustrate, FIG. 2D is a schematic illustration of a wafer 10 that is properly mounted on and aligned relative to a film frame 30, and an inspection process wafer travel path along which an image capture device captures an image of the entire surface area of each die 12 within successive rows of die 12 on the wafer 10. Two representative rows of die 12 are identified in FIG. 2D, namely, row "A" die 12 and row "B" die. Because this wafer 10 is properly aligned relative to its film frame 30, during the inspection process the entire surface area of each die 12 within row "A" can be captured in a single corresponding image (e.g., while the wafer 10 is in motion, or "on-the-fly"). Following the capture of the images corresponding to the row "A" die, the wafer 10 is immediately positioned such that the surface area of a row "B" die 12 that is closest to the last considered row "A" die 12 can be captured by the image capture device, and inspection continues along an opposite direction of travel. Thus, the inspection travel path is "serpentine." Once again, because this wafer 10 is properly aligned with respect to its film frame 30, during the inspection process the entire surface area of each die 12 within row "B" can be captured in a single corresponding image. Inspection of the entire wafer 10 in this manner, when the wafer 10 is properly aligned relative to its film frame 30, results in maximum inspection process throughput.

FIG. 2E is a schematic illustration of a wafer 10 that is rotationally misaligned relative to a film frame 30 that carries the wafer, and an inspection process wafer travel path along which an image capture device captures less than the entire surface area of each die 12 within successive rows of die 12 on the wafer 10 during any single image capture event. During an optical inspection process, as a result of such wafer-to-film frame rotational misalignment, the horizontal and vertical sides 14, 16 of the die 12 carried by the wafer 10 will be rotationally offset from the FOV horizontal and vertical axes $X_I$ and $Y_I$, respectively, even when the film frame 30 itself is properly registered with respect to the image capture device. Consequently, the entire surface area of a given die 12 may not fall within the image capture device FOV 50, and multiple individual images will be required to capture a given die's entire surface area. Because an inspection result cannot be generated for the die 12 until after multiple images have captured the die's entire surface area, the generation of an inspection result corresponding to the die 12 is undesirably delayed.

Analogous considerations to those described above apply when inspection involves a group of die 12. FIG. 2F is a schematic illustration of a die array 18 in which the collective surface area of all die 12 within the die array 18 is smaller than an image capture device FOV 50, and the die array 18 is properly aligned relative to the image capture device FOV 50 because the horizontal and vertical sides 14, 16 of each die 12 within the die array 18 are substantially parallel to the FOV horizontal axis $X_I$ and the FOV vertical axis $Y_I$, respectively. As a result, the entire die array 18 can be captured as a single image by the image capture device, thereby maximizing inspection process throughput. FIG. 2G is a schematic illustration of a die array 18 for which the horizontal and vertical sides 14, 16 of the die 12 within the die array 18 are not properly aligned with respect to the FOV horizontal and vertical axes $X_I$ and $Y_I$. Thus, portions of the die array 18 fall outside of the FOV 50. As a result, multiple images of the die array 18 must be captured before an inspection result can be generated for the die array 18, thereby lowering throughput.

Moreover, analogous considerations to those described above also apply when inspection involves a single (e.g., large) die 12 that, when properly aligned relative to the image capture device FOV 50, has a surface area that is larger than the FOV 50. FIG. 2H is a schematic illustration of a die 12 having a surface area that is larger than the FOV 50 of an image capture device. This die 12 is also properly aligned relative to the FOV 50, because the die's horizontal and vertical sides 14, 16 are substantially parallel to the FOV horizontal and vertical axes $X_I$ and $Y_I$, respectively. As a result, the overall surface area of the die 12 can be captured in a minimum number of image capture operations. In this example, the image capture device must capture a total of 9 images for inspection of the entire surface area of the die 12, which occurs by way of successively positioning different portions of the die's surface area relative to the image capture device, and capturing an image of each portion of the die's surface area that falls within the image capture device FOV 50 during each such relative positioning.

FIG. 2I is a schematic illustration of a single die 12 such as that shown in FIG. 2H, which under proper FOV alignment conditions would be completely inspected through the capture of 9 images, but for which horizontal and vertical die side misalignment relative to FOV horizontal and vertical axes $X_I$ and $Y_I$ results in portions of the die 12 remaining outside of the image capture device FOV 50 even after 9 images have been captured.

Prior systems and methods rely upon either manual intervention or a rotatable wafer table to compensate or correct for rotational misalignment between a wafer 10 and a film frame 30. As before, manual intervention adversely affects system throughput. With respect to a rotatable wafer table, such a wafer table is configured for selectively providing an amount of rotational displacement that is sufficient to compensate or substantially compensate for wafer—film frame rotational misalignment. The magnitude of misalignment between a wafer 10 and a film frame 30 can span a significant number of degrees, for instance, 10-15 degrees or more, in a positive or negative direction. Unfortunately, a wafer table configured for providing such rotation is undesirably complex from a mechanical standpoint, and correspondingly expensive (e.g., prohibitively expensive). Furthermore, the additional structural complexity of a wafer table assembly that provides such rotational wafer table displacement can make it significantly more difficult to consistently maintain the wafer table surface in a single plane perpendicular to the optical axis of the image capture device during inspection.

A need exists for a wafer and film frame handling system that provides a single wafer table structure for handling both wafers and film frames, and which can automatically overcome at least some of the aforementioned problems arising from wafer warpage, unpredictable lateral wafer motion, and wafer—film frame rotational misalignment, and which can enhance or maximize inspection process throughput.

SUMMARY

In accordance with an aspect of the present disclosure, a system for handling wafers and film frames on which wafers or portions thereof are mounted includes a wafer table assembly comprising a wafer table providing an ultra-planar wafer table surface (which can include a porous material) configured for carrying a wafer or a film frame, the wafer table assembly configured for applying a negative pressure or a positive pressure to an underside of a wafer or an underside of a film of a film frame on which the wafer is mounted; and at least one of: (i) a flattening apparatus configured for automatically applying a downward force to portions of a warped or non-planar wafer in a direction normal to the wafer table surface in response to a detection of insufficient wafer retention upon the wafer table surface; (ii) a displacement limitation apparatus configured for automatically constraining or preventing uncontrolled lateral motion of a wafer relative to the wafer table surface after cessation of an applied negative pressure and application of a positive pressure to the underside of the wafer via the wafer table; and (iii) a rotational misalignment compensation apparatus configured for automatically compensating for a rotational misalignment of a wafer mounted on a film frame. The wafer table assembly can exclude film frame registration elements configured for facilitating film frame alignment by way of mating engagement with a set of film frame reference features.

The rotational misalignment apparatus can include a first image capture device configured for capturing an image of portions of the wafer mounted on the film frame; and a processing unit configured for determining an angular extent of rotational misalignment and a direction of rotational misalignment of the wafer mounted on the film frame with respect to (i) a field of view of the first image capture device and/or (ii) the film frame.

The flattening apparatus eliminates a need for manual intervention when the warped or non-planar wafer cannot be reliably retained on the wafer table surface as a result of its warpage or non-planarity. The displacement limitation apparatus eliminates a need for manual intervention in response to uncontrolled lateral displacement of the wafer relative to the wafer table surface after cessation of an application of negative pressure to the underside of the wafer. The displacement limitation apparatus can facilitate release of the very thin or ultra-thin wafer from the wafer table surface after an application of positive air pressure in a manner that reliably avoids damaging a very thin or ultra-thin wafer by preventing uncontrolled lateral displacements of the ultra-thin wafer.

In an embodiment, the system includes a multi-function handling apparatus having: a main body positionable over the wafer table surface and displaceable along a vertical axis that is perpendicular to the wafer table surface; a plurality of capture arms coupled to the main body, each capture arm within the plurality of capture arms controllably displaceable to multiple distinct positions transverse to and towards or away from the vertical axis; a set of vacuum elements coupled to the plurality of capture arms and configured for controllably applying vacuum forces to portions of a periphery of a film frame to facilitate secure capture of the film frame by the plurality of capture arms; and a vertical displacement driver configured for controllably displacing the main body and consequently simultaneously displacing the plurality of capture arms along a vertical direction parallel to the vertical axis to transport the film frame to the wafer table surface by directly placing the film frame thereon. The multi-function handling apparatus can further include a rotational misalignment compensation driver configured for precisely and simultaneously rotating the plurality of capture arms about the vertical axis to compensate for a rotational misalignment of a wafer mounted on the film frame relative to the film frame and/or a field of view of an image capture device, while the film frame is transported to the wafer table surface.

In an embodiment, the system includes a handling subsystem having: a main body positionable over the wafer table surface and displaceable along a vertical axis that is perpendicular to the wafer table surface; a plurality of capture arms coupled to the main body, each capture arm within the plurality of capture arms controllably displaceable to multiple distinct positions transverse to and towards or away from the vertical axis; and a capture arm tip coupled to each capture arm within the plurality of capture arms, each capture arm tip comprising a soft and resiliently deformable material, wherein the handling subsystem implements at least one of the flatting apparatus and the displacement limitation apparatus; or each of the film frame transport apparatus, the flattening apparatus, the displacement limitation apparatus, and the rotational misalignment compensation apparatus.

The plurality of tip elements is displaceable to at least one of: (i) a plurality of engagement assistance positions, each engagement assistance position disposing the plurality of tip elements away from each other across an area that is slightly less than a standard wafer diameter at the periphery of a wafer on the wafer table surface; and (ii) a plurality of confinement positions, each confinement position disposing a each tip element within the plurality of tip elements beside and just beyond the periphery of a wafer on the wafer table surface, wherein each engagement assistance position corresponds to a different standard wafer dimension and each confinement position corresponds to a different standard wafer dimension.

The wafer table assembly includes a set of ejector pins displaceable along a vertical direction perpendicular to the wafer table surface, and the displacement limitation apparatus can include: a control unit configured for controlling: (a) an application of an air puff to the underside of the wafer essentially immediately after interruption or cessation of the application of the suction force to the underside of the wafer, the air puff applied from an air puff onset time to an air puff cessation time; and (b) activation of the set of ejector pins to displace the set of ejector pins in an upward direction after a very brief ejector pin activation delay time following the air puff onset time to thereby lift the wafer off of the wafer table surface with minimal or negligible lateral displacement as a result of the very brief ejector pin activation delay time relative to the air puff onset time, wherein the ejector pin activation delay time is precisely controlled relative to the air puff onset time such that the wafer is vertically raised away from the wafer table surface synchronous with the release of the wafer from the wafer table surface in response to the air puff. The ejector pin activation delay time is experimentally determined, and/or can be between 5-50 msec.

In accordance with an aspect of the present disclosure, a process for handling wafers and film frames on which wafers or portions thereof are mounted, each wafer having a periphery and a surface area, each film frame including a corresponding film on which a wafer or a portion thereof is mounted and which is supported by the film frame, includes: transporting a wafer to an ultra planar wafer table surface corresponding to a wafer table assembly comprising a wafer table configured for applying a negative pressure or a positive pressure to an underside of a wafer or an underside of a film of a film frame on which the wafer is mounted; and at least one of, and possibly each of: (i) automatically remediating a rotational misalignment of a wafer relative to a film frame on which the wafer is mounted; (ii) automatically remediating insufficient retention of the wafer upon the wafer table surface due to wafer warpage or non-planarity; and (iii) automatically preventing uncontrolled lateral displacement of the wafer relative to the wafer table surface following interruption or cessation of the suction force to the underside of the wafer.

The process can further include removing the wafer from the wafer table by way of elevating a set of ejector pins and an end effector configured to capture the wafer from the elevated set of ejector pins; and directly placing a film frame on the wafer table surface without the use of ejector pins following removal of the wafer from the wafer table without converting the wafer table for film frame handling by way of a conversion kit.

Directly placing the film frame on the wafer table surface can include: positioning a film frame transport apparatus over the film frame, the film frame transport apparatus comprising a housing coupled to a plurality of displaceable capture arms, each capture arm coupled to a soft and resiliently deformable tip element, each capture arm fluidly coupled to a vacuum or negative pressure source; positioning the plurality of capture arms at a film frame capture position corresponding to a standard dimension of the film frame, such that the tip elements engage with portions of a film frame border; applying a vacuum force or negative pressure to portions of the film frame border by way of the plurality of capture arms to securely capture the film frame;

positioning the captured film frame over the wafer table surface; displacing the captured film frame downward toward the wafer table surface until the film frame contacts the wafer table surface; applying a suction force to an underside of the film corresponding to the film frame by way of the wafer table; and terminating the application of vacuum force or negative pressure to portions of the film frame border.

Automatically remediating a rotational misalignment of a wafer relative to a film frame on which the wafer is mounted can include: capturing an image of portions of the wafer mounted on the film frame using an image capture device; determining a rotational misalignment angle and a rotational misalignment direction of the wafer relative to the film frame and/or the image capture device; rotating the film frame across the rotational misalignment angle in a direction opposite to the rotational misalignment direction by way of a rotational compensation apparatus separate from the wafer table; and placing the film frame on the wafer table.

Capturing an image of portions of the wafer can include capturing an image of portions of the wafer using a first image capture device prior to placement of the film frame on the wafer table. Capturing such an image can occur by way of a second image capture device that forms a portion of an inspection system after placement of the film frame on the wafer table.

Automatically remediating insufficient retention of the wafer upon the wafer table surface can include: automatically detecting insufficient retention of the wafer upon the wafer table surface; and responsively applying a set of downward forces to portions of an exposed upper surface of the wafer concurrent with the application of the suction force to the underside of the wafer to facilitate secure retention of the wafer upon the wafer table surface. Applying the set of downward forces can include: positioning a flattening apparatus above the wafer, the flattening apparatus comprising a housing coupled to a plurality of displaceable arms, each arm within the plurality of arms coupled to a tip element comprising a soft and resiliently deformable material; positioning the tip elements in accordance with an engagement assistance position corresponding to a dimension of the wafer upon the wafer table, such that a portion of each tip element is disposed directly over the exposed upper surface of the wafer for engaging with or contacting a portion of the exposed surface of the wafer; and displacing the tip elements disposed over the exposed upper surface of the wafer downward toward the wafer table surface.

Such automatic remediation of insufficient wafer retention upon the wafer table surface can further include: detecting secure retention of the wafer upon the wafer table surface by way of the vacuum gauge; and terminating the application of the set of downward forces to portions of the exposed upper surface of the wafer in response to secure retention of the wafer on the wafer table surface.

Automatically preventing uncontrolled lateral displacement of the wafer relative to the wafer table surface can include positioning a confinement apparatus above the wafer, the confinement apparatus comprising a housing coupled to a plurality of displaceable arms, each arm within the plurality of arms coupled to a tip element comprising a soft and resiliently deformable material; positioning the tip elements in accordance with a confinement position corresponding to a dimension of the wafer upon the wafer table, such that a portion of each tip element is disposed just beyond the periphery of the wafer; interrupting or terminating the application of suction force to the underside of the wafer; and activating a set of ejector pins corresponding to the wafer table in an upward direction to elevate the wafer away from the wafer table surface.

Alternatively, automatically preventing uncontrolled lateral displacement of the wafer relative to the wafer table surface can include: interrupting or terminating the application of suction force to the underside of the wafer; applying an air puff to the underside of the wafer essentially immediately after interruption or cessation of the application of the suction force to the underside of the wafer, the air puff applied from an air puff onset time to an air puff cessation time; and activating a set of ejector pins corresponding to the vacuum table to displace the set of ejector pins in an upward direction after a very brief ejector pin activation delay time following the air puff onset time to thereby lift the wafer off of the wafer table surface with minimal or negligible lateral displacement as a result of the very brief ejector pin activation delay time relative to the air puff onset time, wherein the ejector pin activation delay time is precisely controlled relative to the air puff onset time such that the wafer is vertically raised away from the wafer table surface synchronous with the release of the wafer from the wafer table surface in response to the air puff.

In accordance with an aspect of the present disclosure, a process for handling a wafer in association with an inspection process performable by an inspection system includes: retrieving the wafer from a wafer source; transporting the wafer to a wafer prealigner; disposing the wafer on a wafer table surface provided by a wafer table following prealignment of the wafer; applying a negative pressure to an underside of the wafer; and at least one of: (i) automatically remediating insufficient retention of the wafer upon the wafer table surface due to wafer warpage or non-planarity by way of: detecting whether the wafer is securely retained upon the wafer table surface prior to the initiation of the inspection process, and automatically applying a downward force to portions of the wafer until secure retention of the wafer upon the wafer table surface is detected; (ii) automatically preventing uncontrolled lateral displacement of the wafer along the wafer table surface following the inspection process as a result of cessation of the application of the negative pressure to the wafer by way of: automatically confining the wafer to reside within a confinement position on the wafer table, or coordinating the cessation of the application of the negative pressure to the underside of the wafer with an application of an air puff to the underside of the wafer and an activation of a set of ejector pins that is vertically displaceable relative to the wafer table surface, such that the wafer is vertically raised away from the wafer table surface synchronous with the release of the wafer from the wafer table surface in response to the air puff; and retrieving the wafer from the wafer table and transferring the wafer to a wafer destination.

In accordance with an aspect of the present disclosure, a process for handling a film frame in association with an inspection process performable by an inspection system includes: retrieving the film frame from a film frame source; capturing an image of portions of the wafer mounted to the film frame using a first image capture device; determining by way of image processing operations an angular misalignment magnitude and an angular misalignment direction of rotational misalignment of the wafer relative to the film frame and/or the first image capture device; transferring the film frame to a multi-function handling apparatus configured for (i) automatically rotating the film frame on which the wafer is mounted to compensate for rotational misalignment of the wafer relative to the film frame and/or the first image capture device, and (ii) directly placing the film frame on a wafer table surface of a wafer table corresponding to the inspection system, wherein the multi-function handling apparatus is separate from the inspection system; initiating the inspection process using a second image capture device corresponding to the inspection system following compensation for the rotational misalignment of the wafer relative to the film frame and/or the first image capture device by the multi-function handling apparatus; and transferring the film frame to a film frame destination following completion of the inspection process. The process further includes rotating the film frame across the angular misalignment magnitude in a direction opposite to the angular misalignment direction while the multi-function handling apparatus transfers the film frame to the wafer table surface.

Capturing an image of portions of the wafer mounted on the film frame using the first image capture device can occur (a) while the film frame is being carried by an end effector of a robotic arm toward the multi-function handling apparatus, (b) after the film frame has been transferred to the multi-function handling apparatus and prior to placement of the film frame on the wafer table surface, or (c) after the film frame has been placed on the wafer table surface.

Transferring the film frame to the film frame destination can include directly removing the film frame from the wafer table surface by way of the multi-function handling apparatus.

BRIEF DESCRIPTION OF THE DRAWINGS

FIG. 5C is a cross sectional view of a post-planarization process vacuum chuck structure corresponding to the base tray carrying hardened porous ceramic material corresponding to FIGS. 5A and 5B.

FIG. 5D is a cross sectional view of a vacuum chuck structure produced or manufactured in accordance with an embodiment of the present disclosure, which corresponds to FIG. 5C, and which carries a wafer or film frame upon a planar vacuum chuck surface.

disposed upon a vacuum chuck structure in accordance with an embodiment of the present disclosure.

Figure 6A:
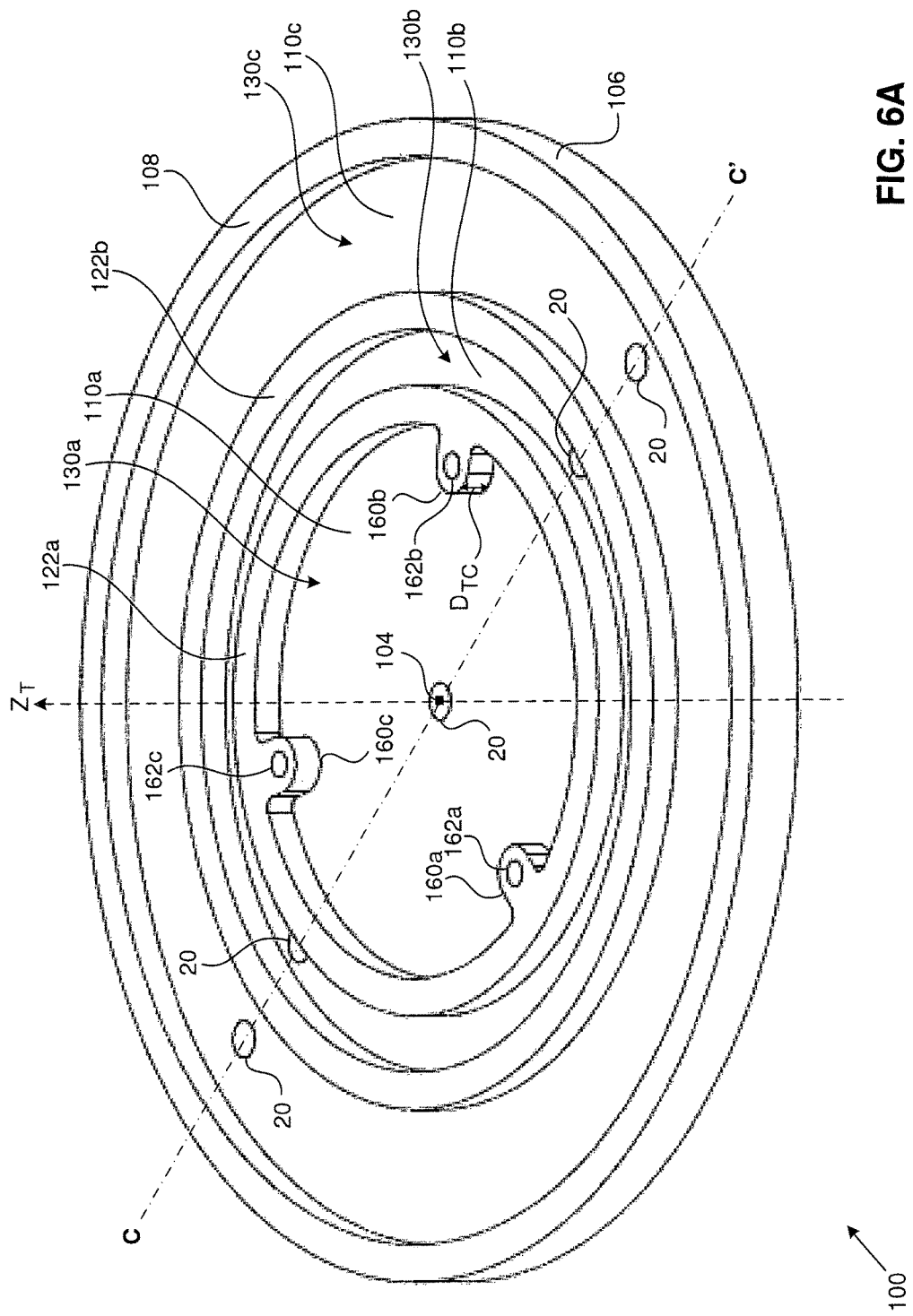

FIG. 6A is a perspective view of a ceramic based vacuum chuck base tray in accordance with another embodiment of the present disclosure, which includes a set of ejector pin guide members.

FIG. 6B is a cross-sectional view of the ceramic based vacuum chuck base tray of FIG. 6A, taken thorough a line C-C'.

Figure 4A:
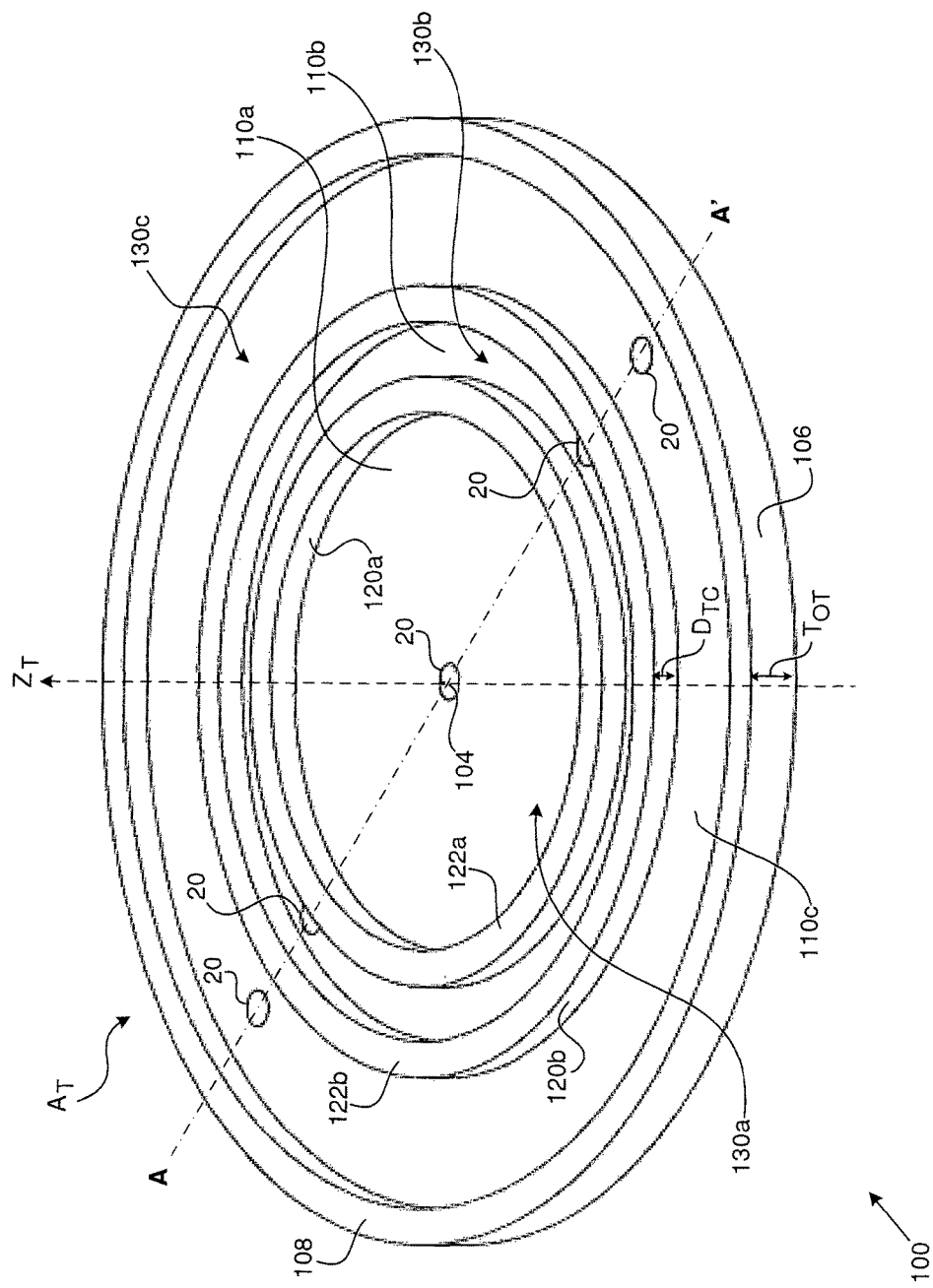
FIG. 4A is a perspective view of a wafer table base tray that includes a non-porous material, such as a ceramic based non-porous material, in accordance with an embodiment of the present disclosure.
Figure 4B:
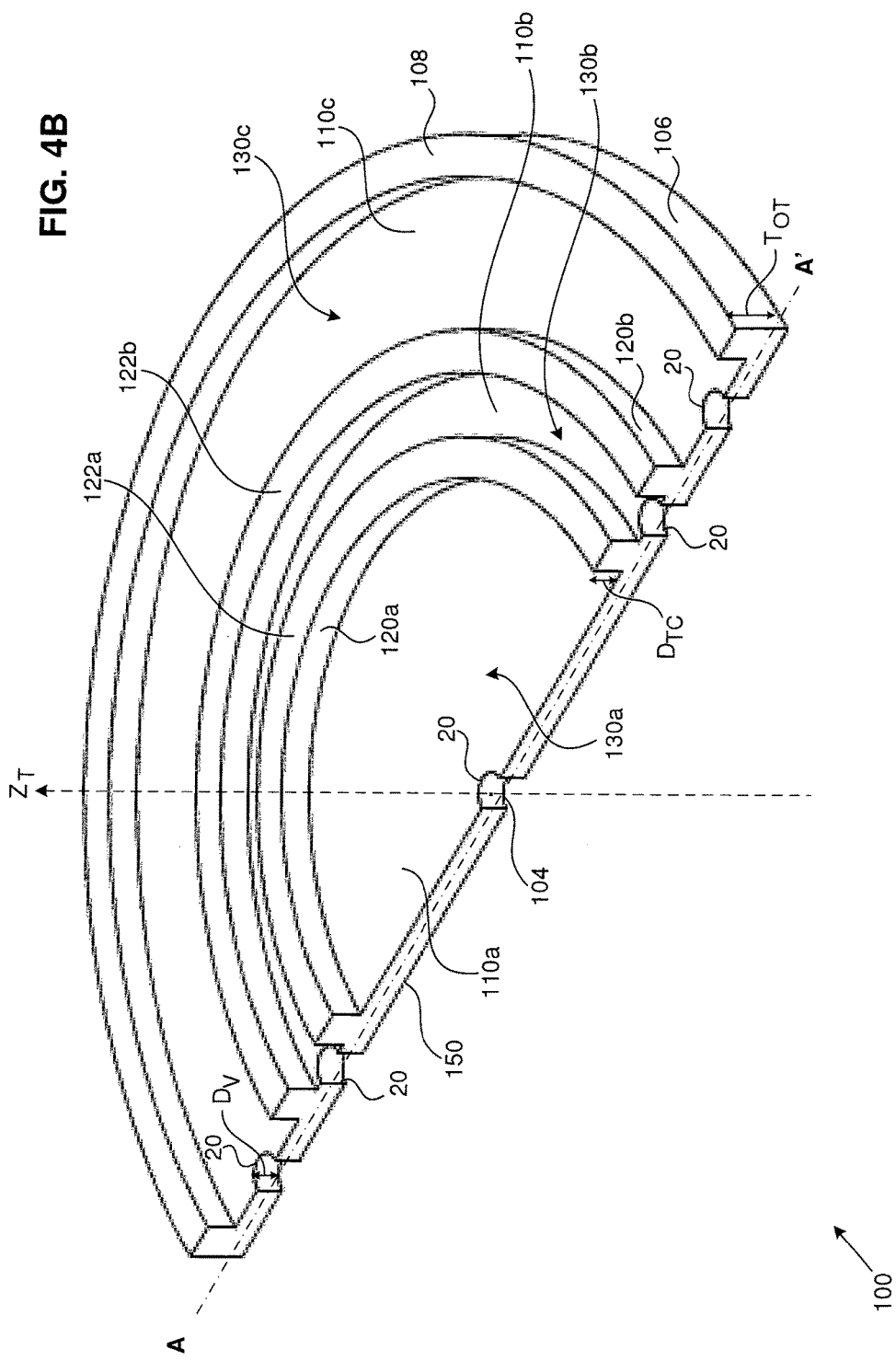
FIG. 4B is a perspective cross sectional view of the base tray of FIG. 4A, taken through a line A-A'.
Figure 7A:
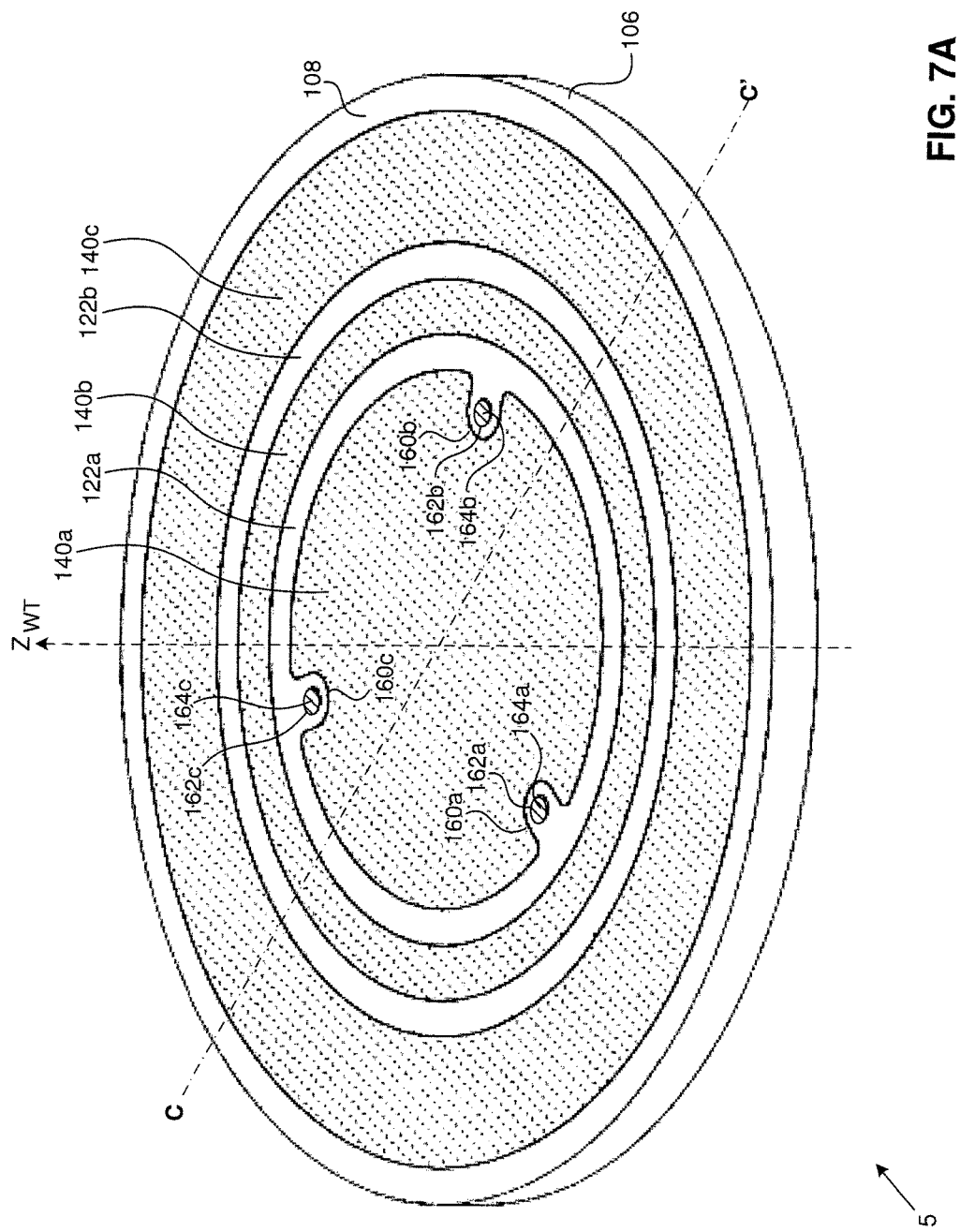

FIG. 7A is a perspective view of the base tray of FIGS. 4A and 4B, into which a moldable, formable, conformable, or flowable porous ceramic based material has been disposed.

Figure 7B:
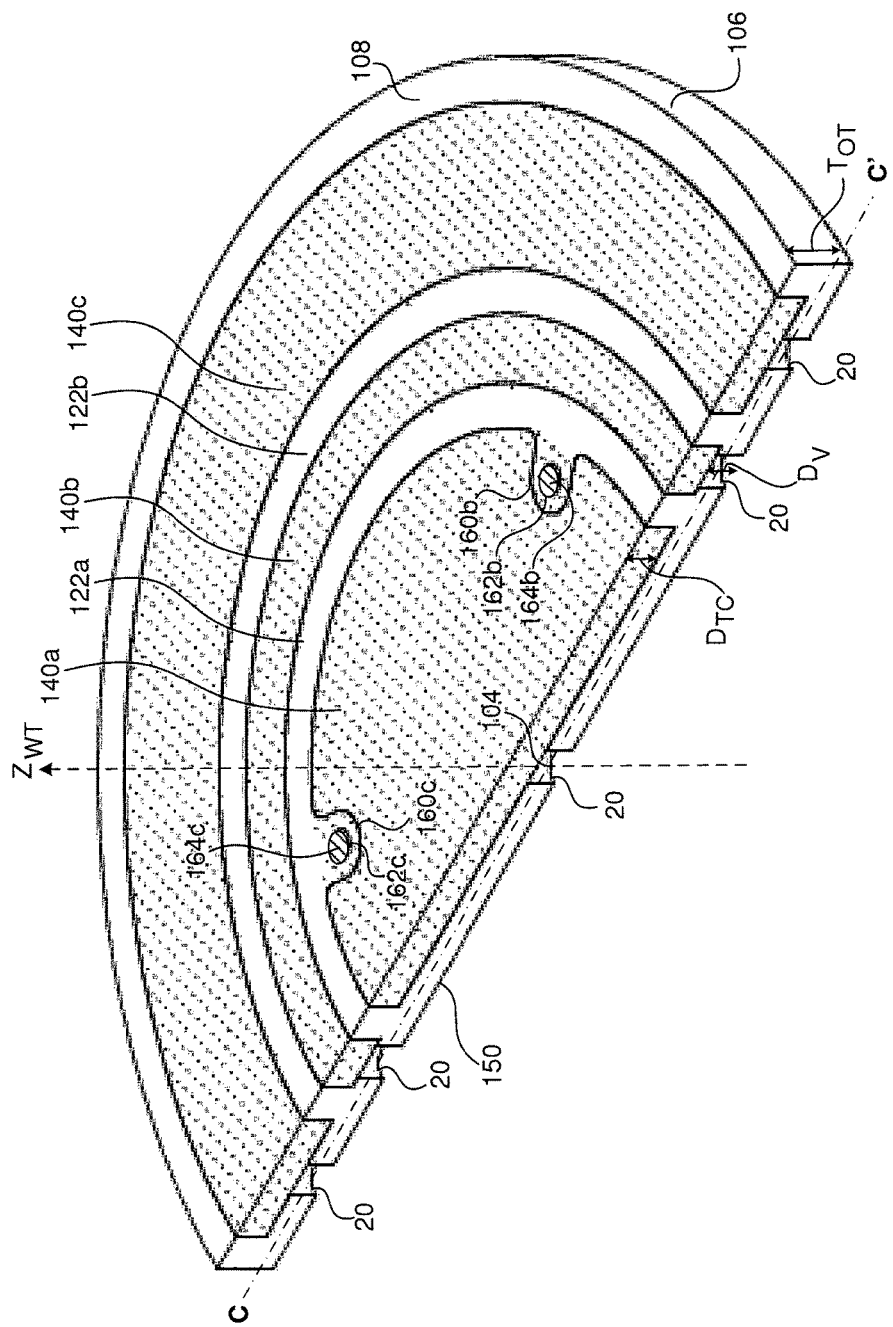

FIG. 7B is a perspective cross sectional view of the base tray carrying the moldable, formable, or flowable porous ceramic based material corresponding to FIG. 7A, taken through a line D-D'.

Figure 8:
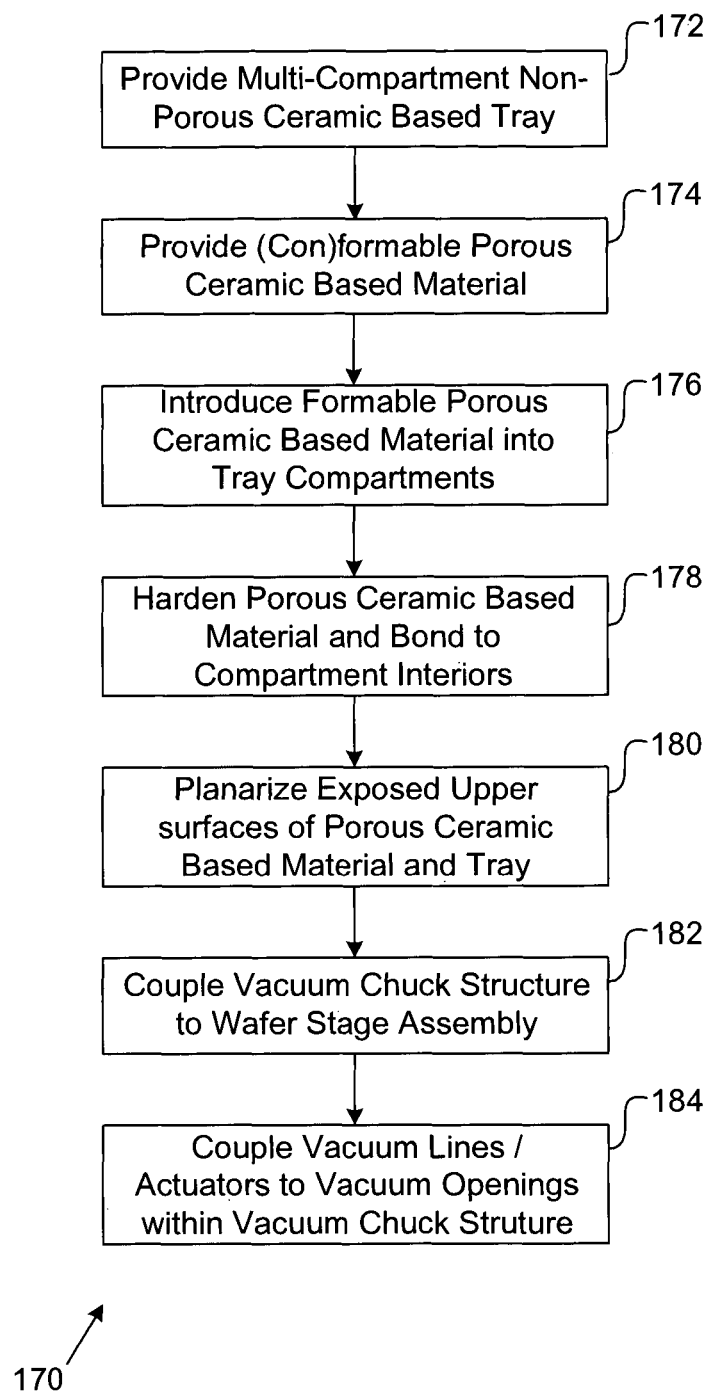

FIG. 8 is a flow diagram of a representative process for manufacturing a vacuum chuck structure in accordance with an embodiment of the present disclosure.

Figure 9:
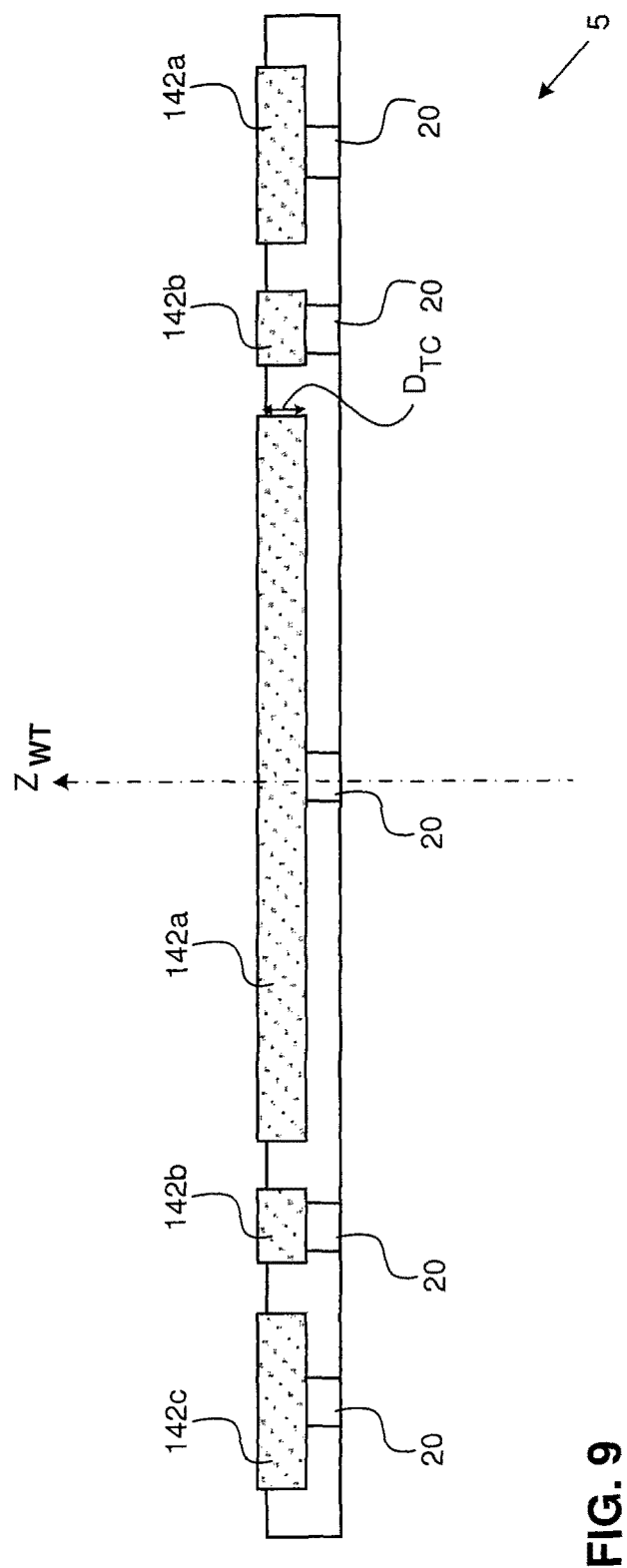

FIG. 9 is a cross sectional view of a vacuum chuck structure in accordance with an embodiment of the present disclosure, which illustrates initial volumes of moldable porous ceramic based material slightly exceeding base tray compartment volumes before completion of a planarization process.

Figure 10A:
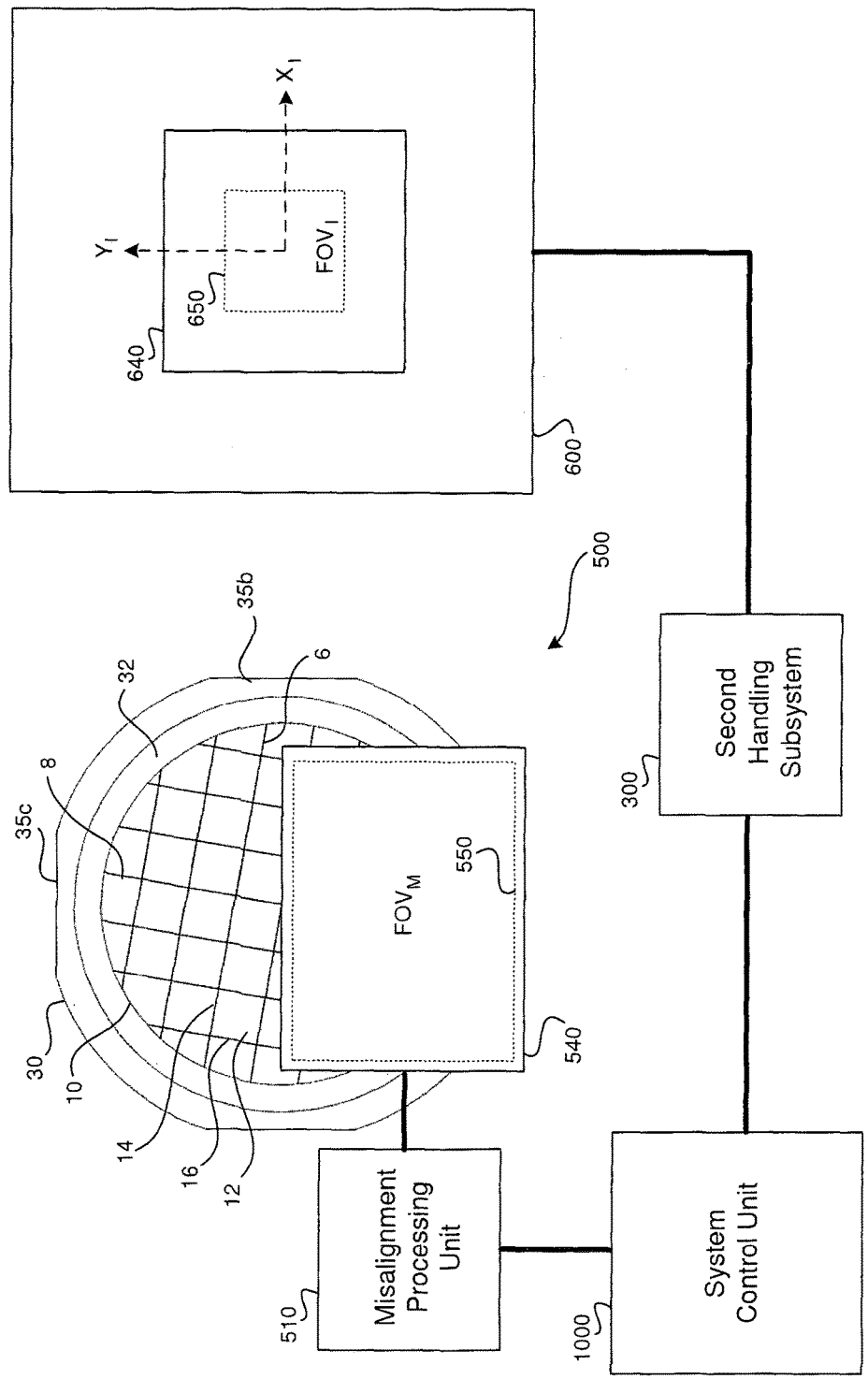

FIG. 10A is a schematic illustration showing an embodiment of a misalignment inspection system configured for determining an extent of rotational or angular wafer misalignment relative to a film frame in accordance with an embodiment of the present disclosure.

Figure 10B:
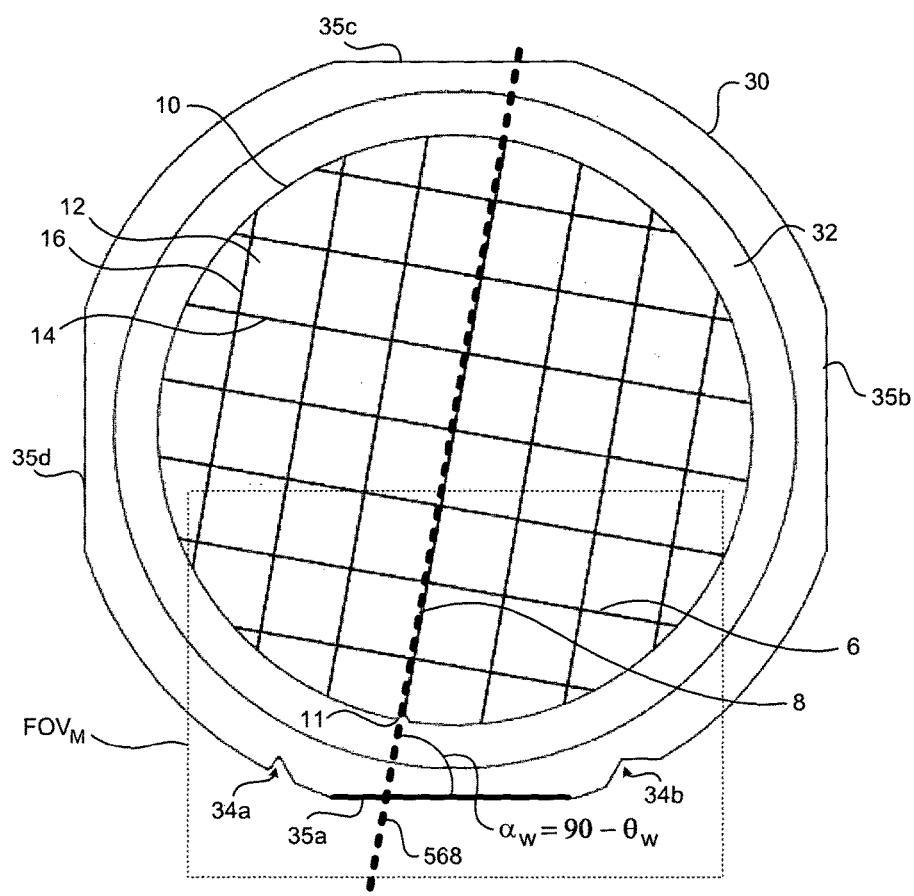

FIG. 10B is a schematic illustration showing aspects of determining an extent of rotational or angular wafer misalignment relative to a film frame by a misalignment inspection system such as that shown in FIG. 10A in accordance with an embodiment of the present disclosure.

Figure 10C:
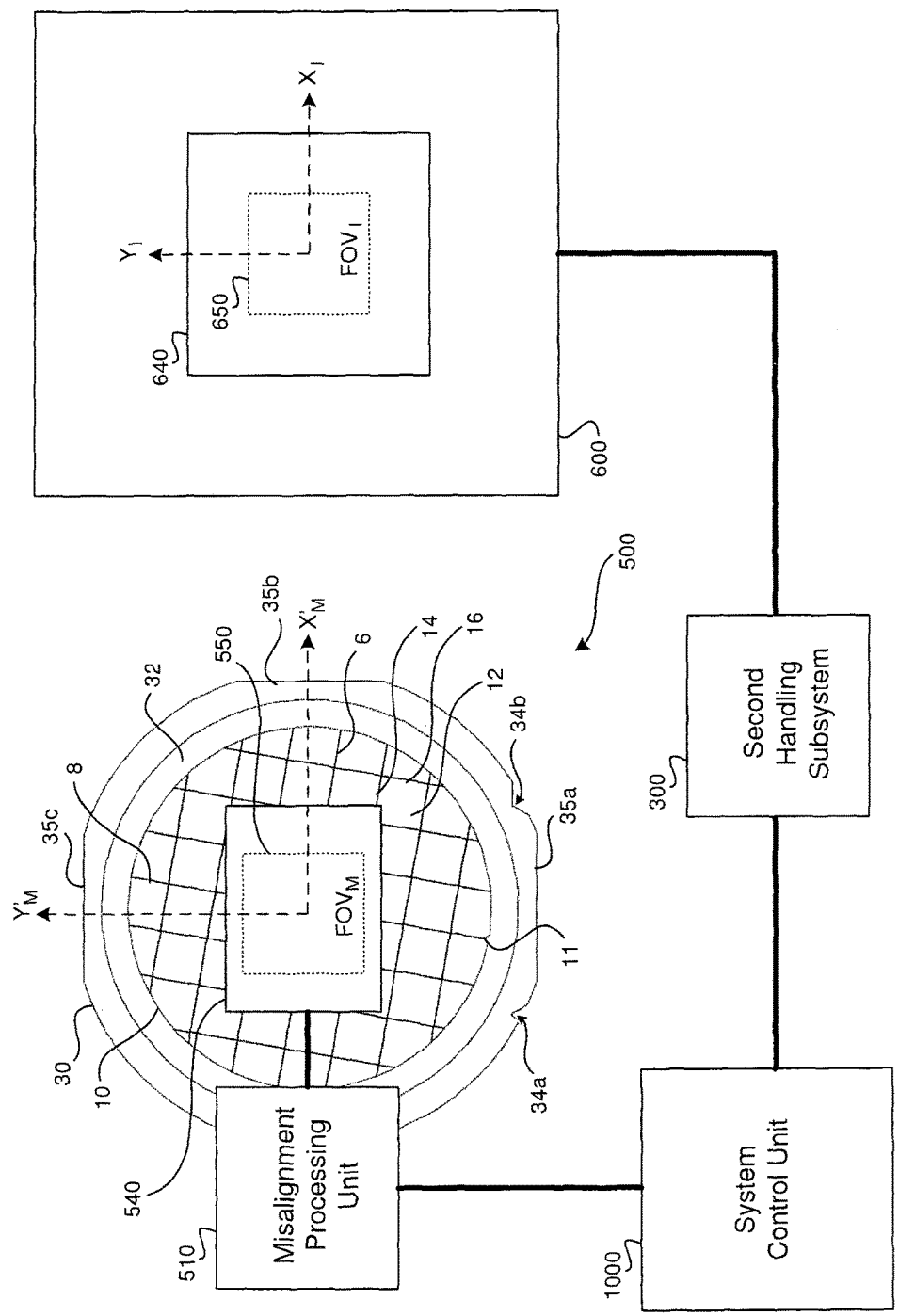

FIG. 10C is a schematic illustration showing an embodiment of a misalignment inspection system configured for determining an extent of rotational or angular wafer misalignment relative to a film frame in accordance with another embodiment of the present disclosure.

Figure 10D:
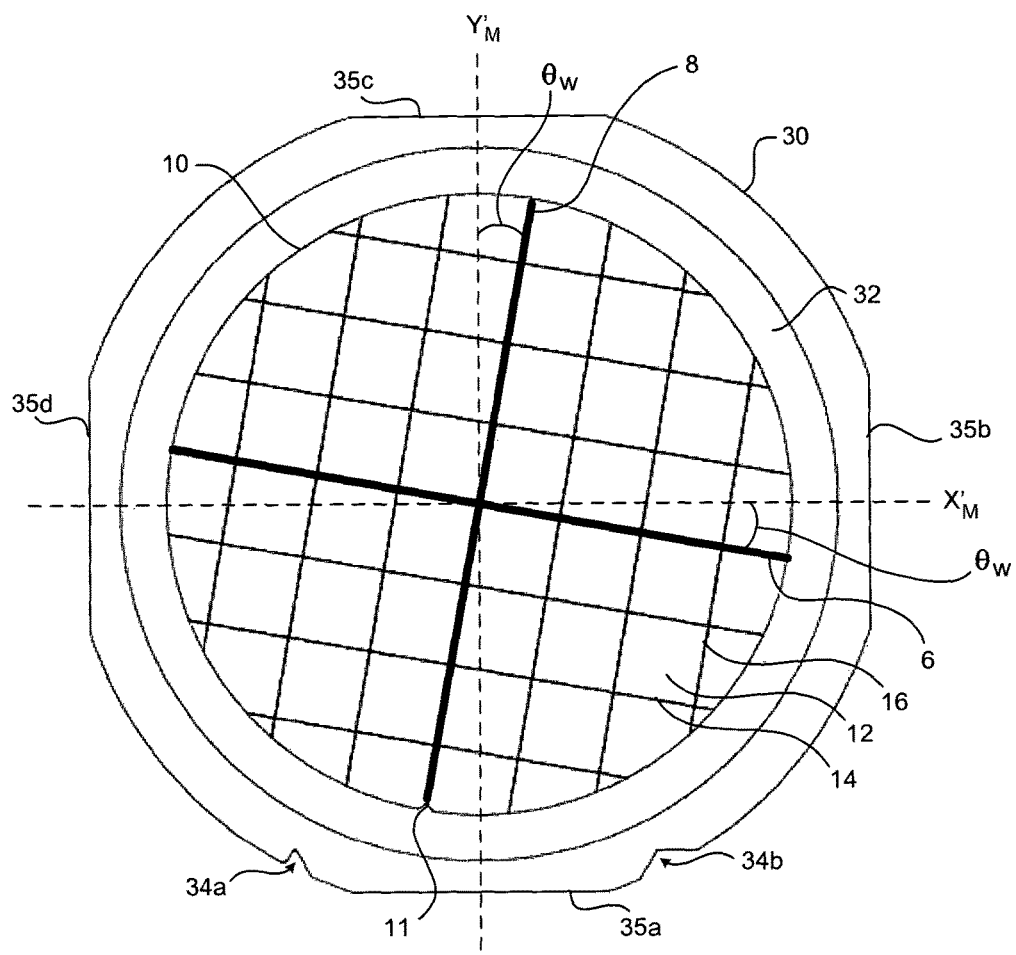

FIG. 10D is a schematic illustration showing aspects of determining an extent of rotational or angular wafer misalignment relative to a film frame by a misalignment inspection system such as that shown in FIG. 10C in accordance with an embodiment of the present disclosure.

Figure 11:
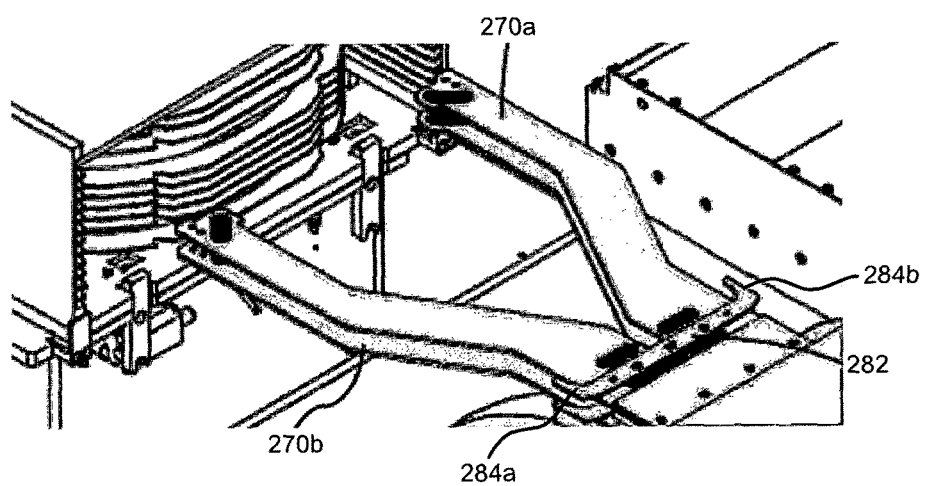

FIG. 11 is a schematic illustration of a set of end effectors that includes at least one end effector which carries a first handling subsystem registration element.

Figure 12A:
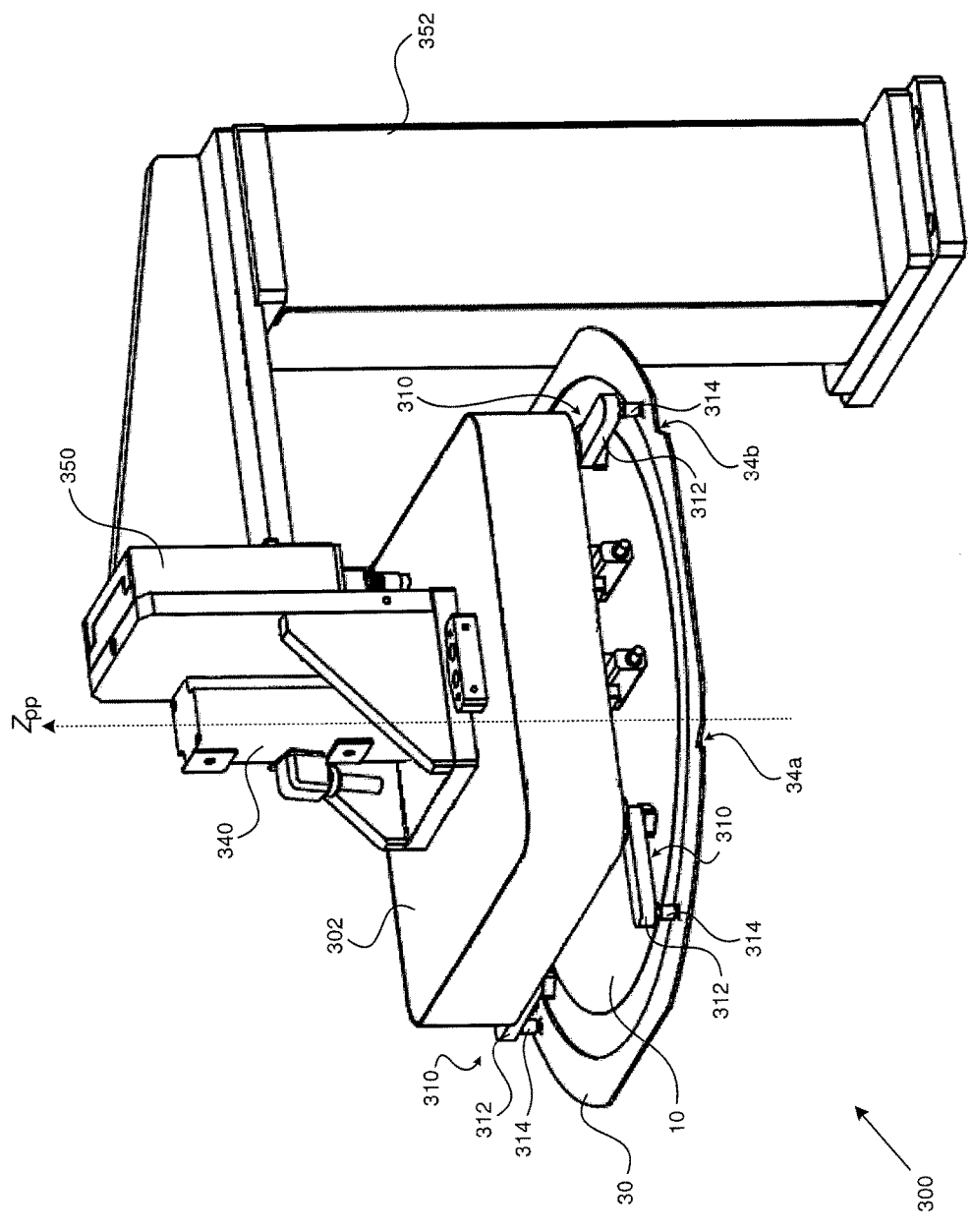

FIG. 12A is a schematic illustration showing aspects of a representative multifunction handling apparatus configured as each of a rotation compensation apparatus, a flattening apparatus, and a confinement apparatus in a combined, integrated, or unified manner for performing wafer and film frame handling operations in accordance with an embodiment of the present disclosure.

Figure 12B:
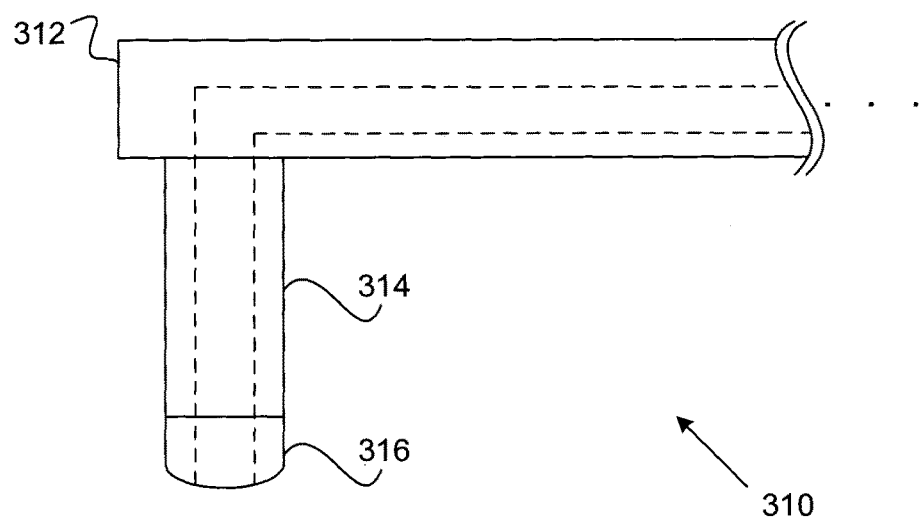

FIG. 12B is a schematic illustration showing portions of a capture arm in accordance with an embodiment of the present disclosure.

Figure 12C:
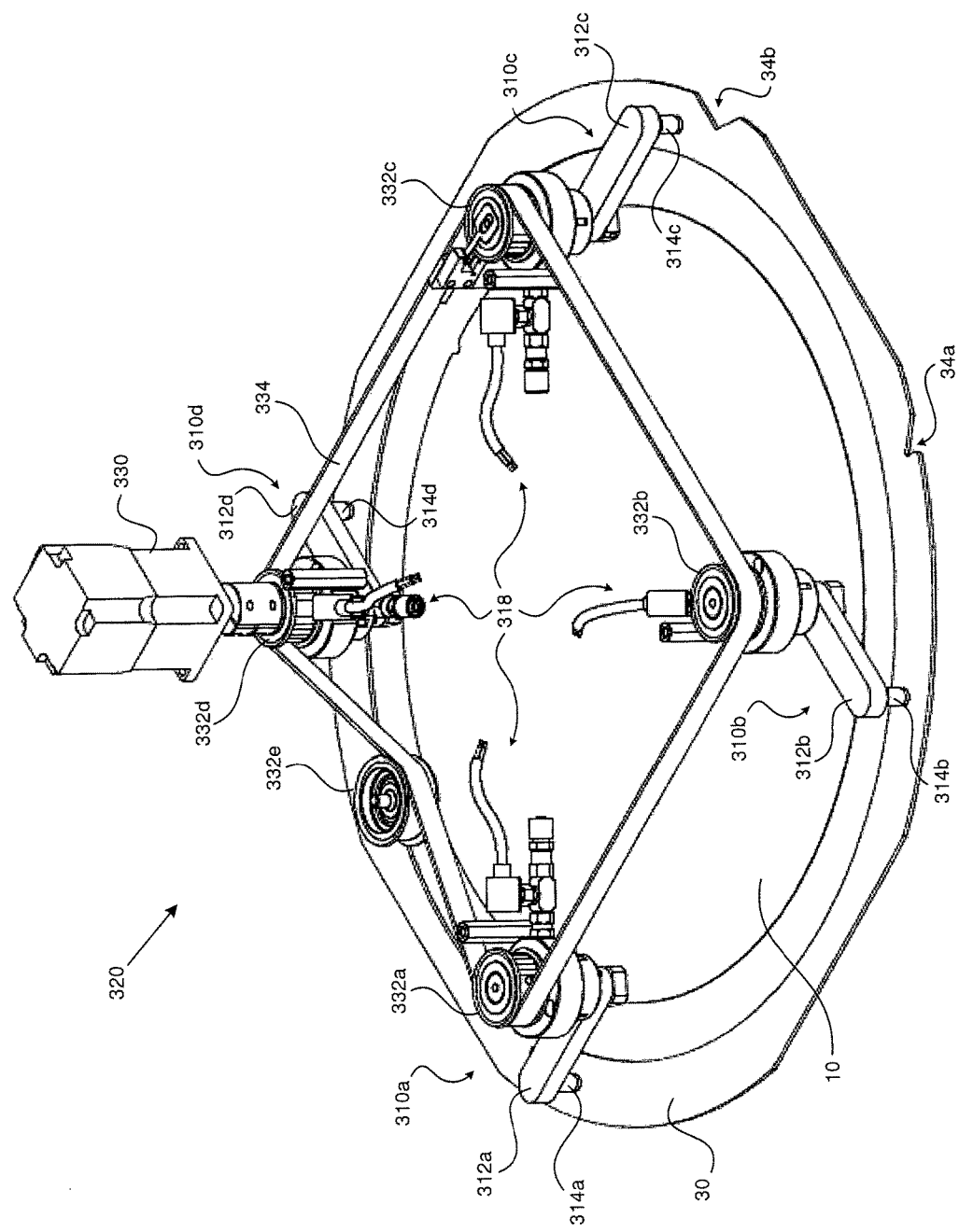

FIG. 12C is a schematic illustration showing portions of a capture positioning assembly in accordance with an embodiment of the present disclosure, and a representative first positioning of a plurality of capture arms at a first position corresponding to a first film frame diameter or cross sectional area.

Figure 12D:
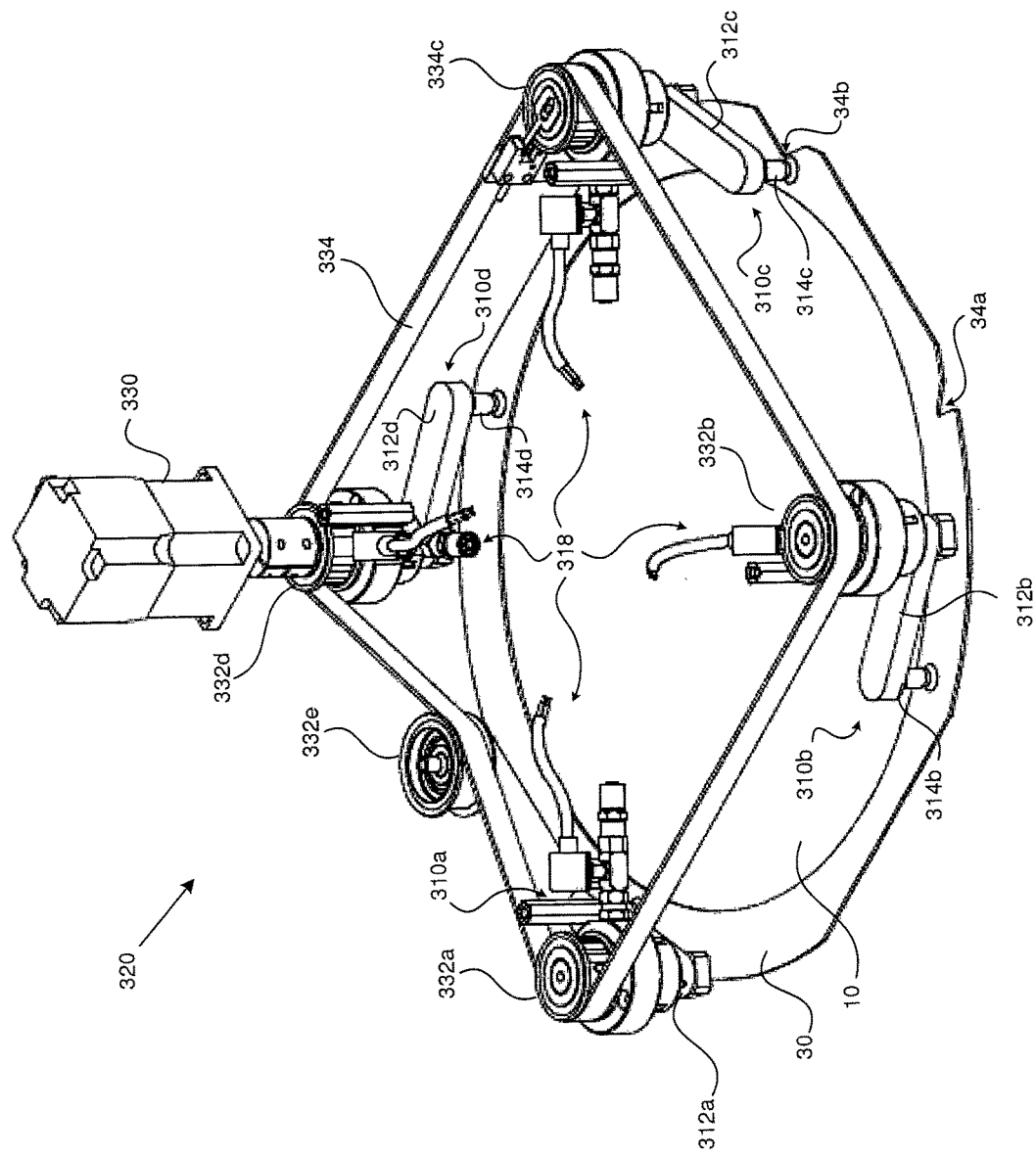

FIG. 12D is a schematic illustration showing portions of the capture positioning assembly, and a representative second positioning of the plurality of capture arms at a second position corresponding to a second film frame diameter or cross sectional area, which is smaller than the first film frame diameter or cross sectional area.

Figure 13A:
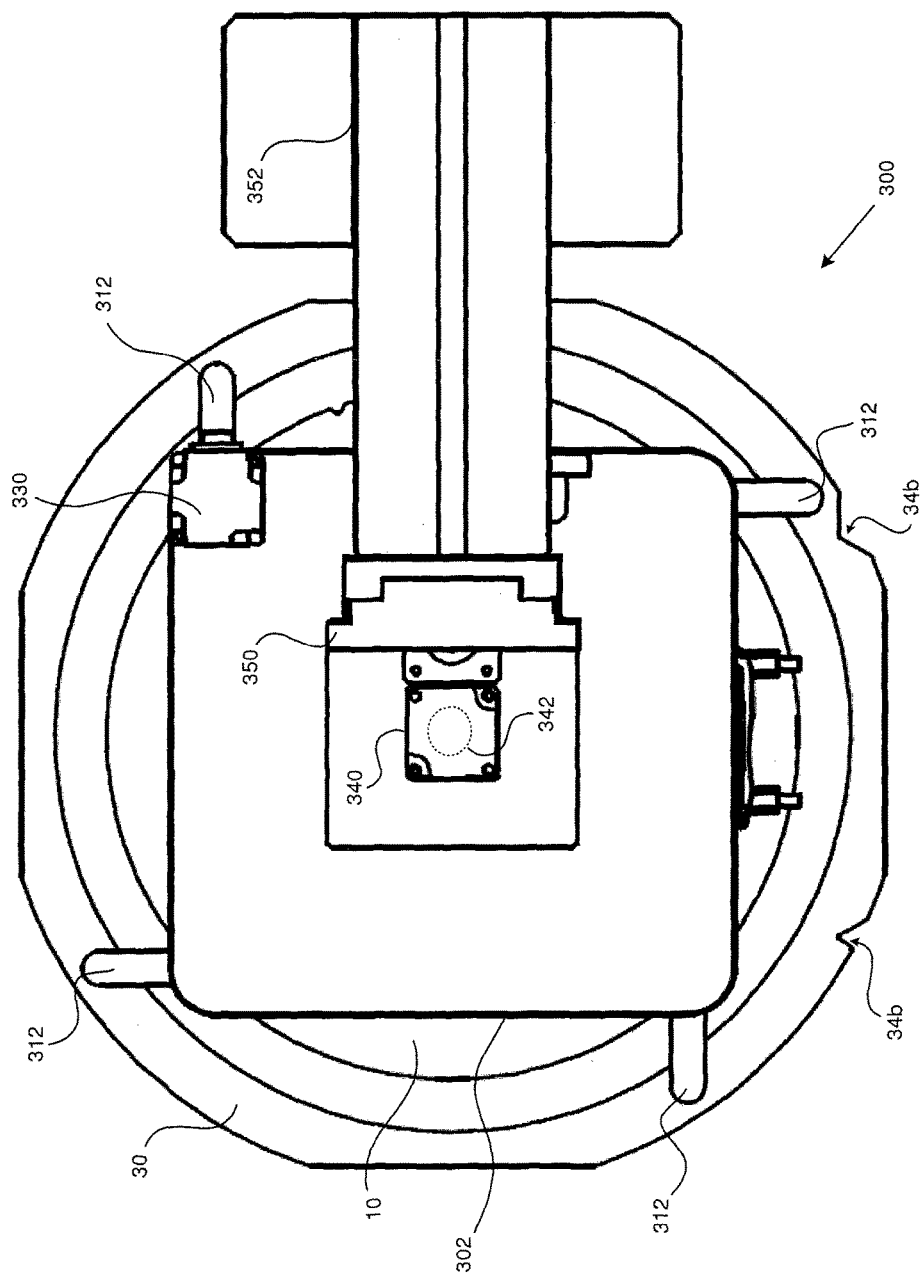

FIG. 13A is a schematic illustration of a film frame carried by a multifunction handling apparatus in accordance with an embodiment of the present disclosure.

Figure 13B:
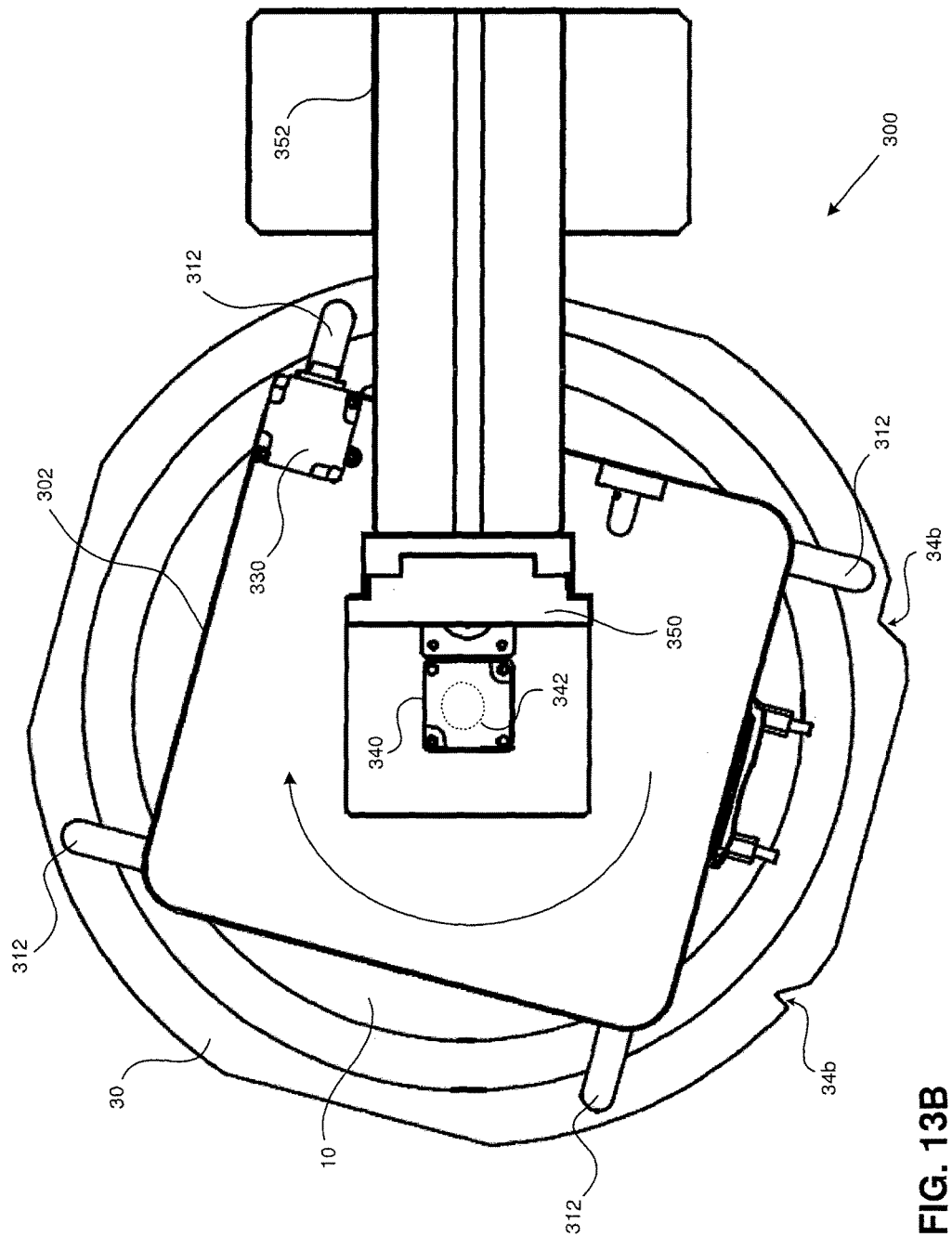

FIG. 13B is a schematic illustration showing portions of the multifunction handling apparatus rotated about a pick and place z axis $Z_{pp}$ to compensate for a first angular misalignment of a first wafer relative to a film frame.

Figure 13C:
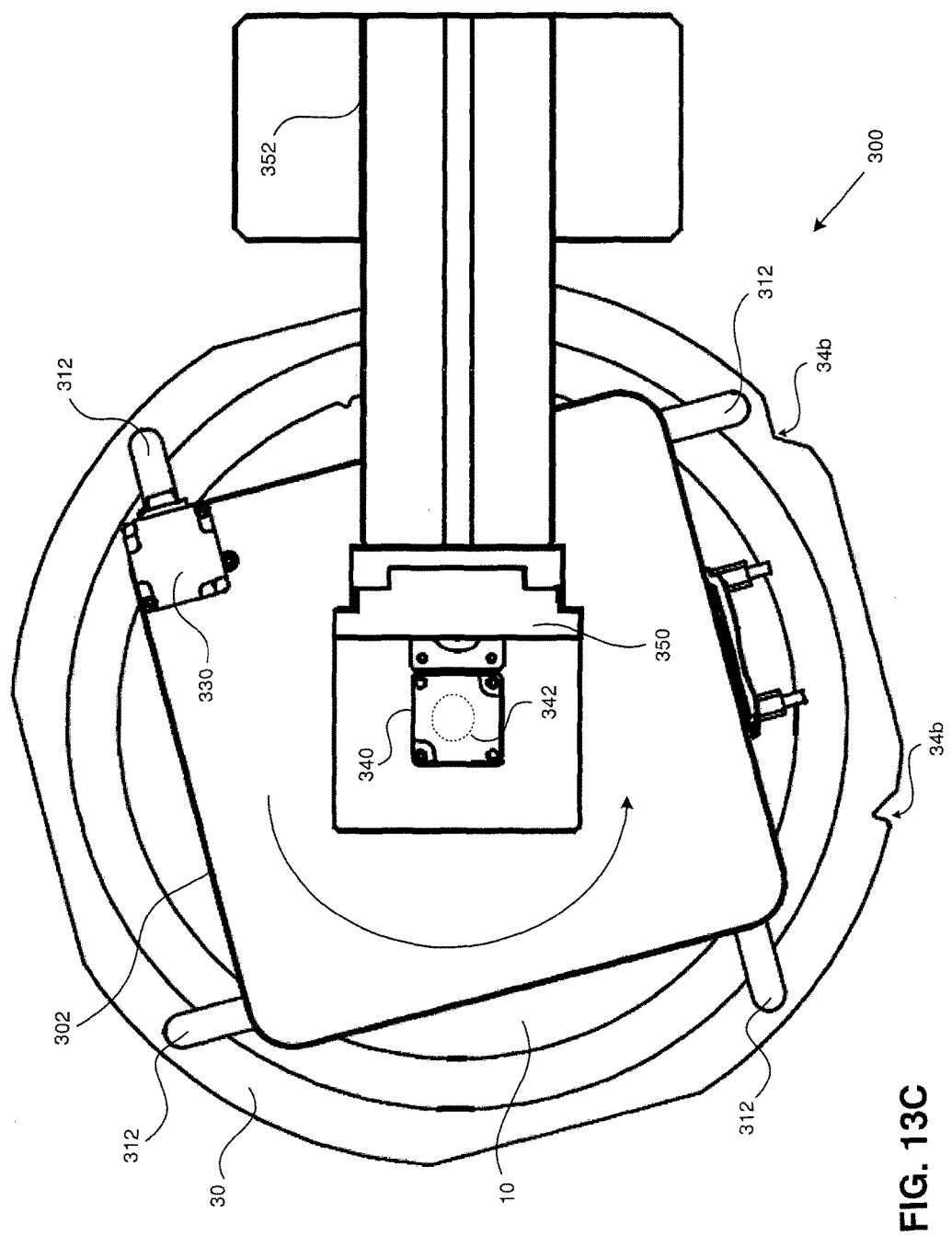

FIG. 13C is a schematic illustration showing portions of the multifunction handling apparatus rotated about the pick and place z axis $Z_{pp}$ to compensate for a second angular misalignment of a second wafer relative to a film frame.

Figure 14A:
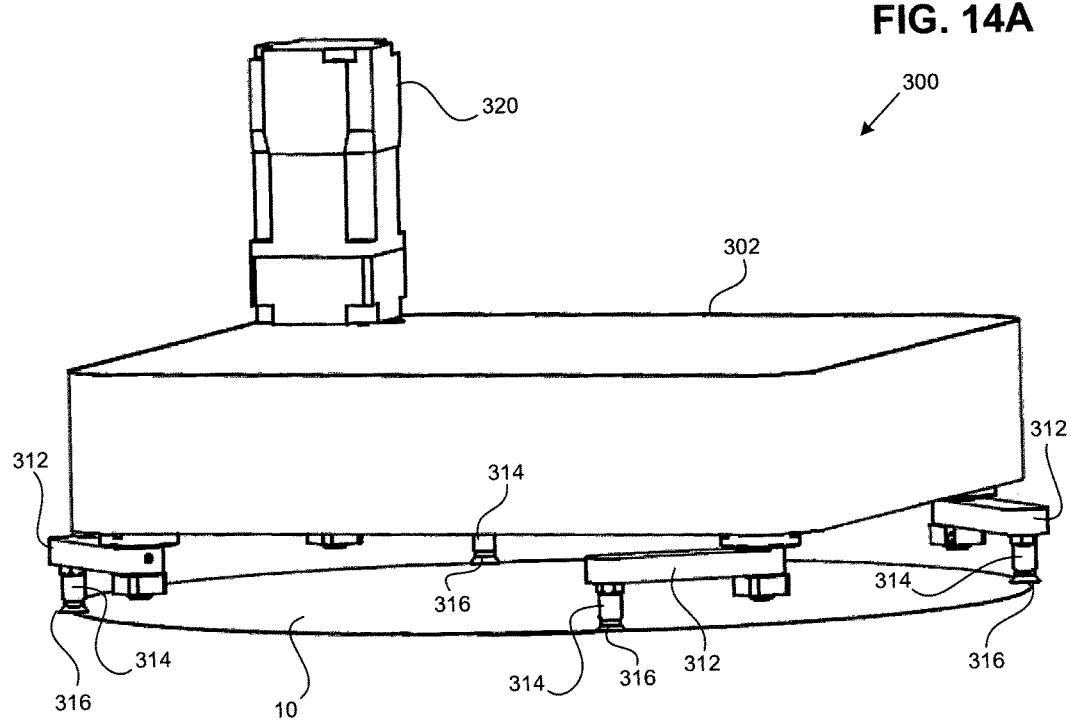
Figure 14B:
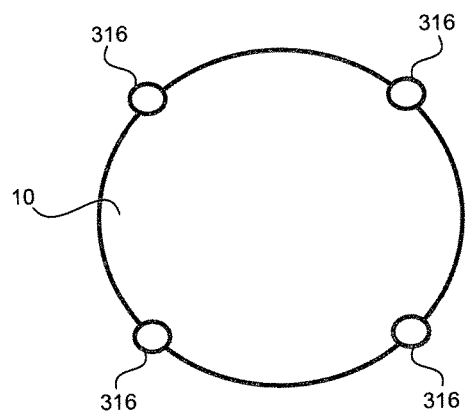

FIGS. 14A-14B are schematic illustrations of multifunction handling apparatus positioning of capture arm tip elements over portions of a wafer to facilitate secure capture of the wafer upon a wafer table surface in accordance with an embodiment of the present disclosure.

Figure 15A:
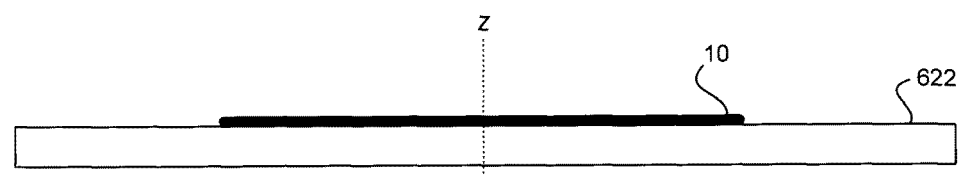

FIG. 15A is a schematic illustration of a representative wafer that is held uniformly upon a wafer table surface by way of natural suction force and a vacuum force applied to the underside of the wafer.

Figure 15B:
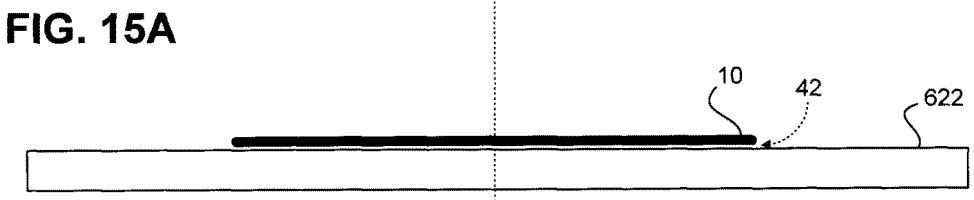

FIG. 15B is a schematic illustration of the wafer of FIG. 15A following vacuum force cessation, and the creation of an air cushion between the wafer and the wafer table surface following application of an air puff to the underside of the wafer.

Figure 15C:
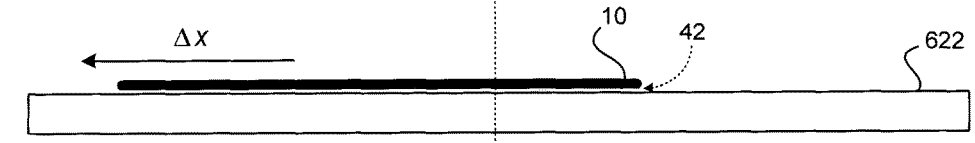

FIG. 15C is a schematic illustration of wafer displacement relative to the wafer table surface as a result of the air cushion shown in FIG. 15B.

Figure 15D:
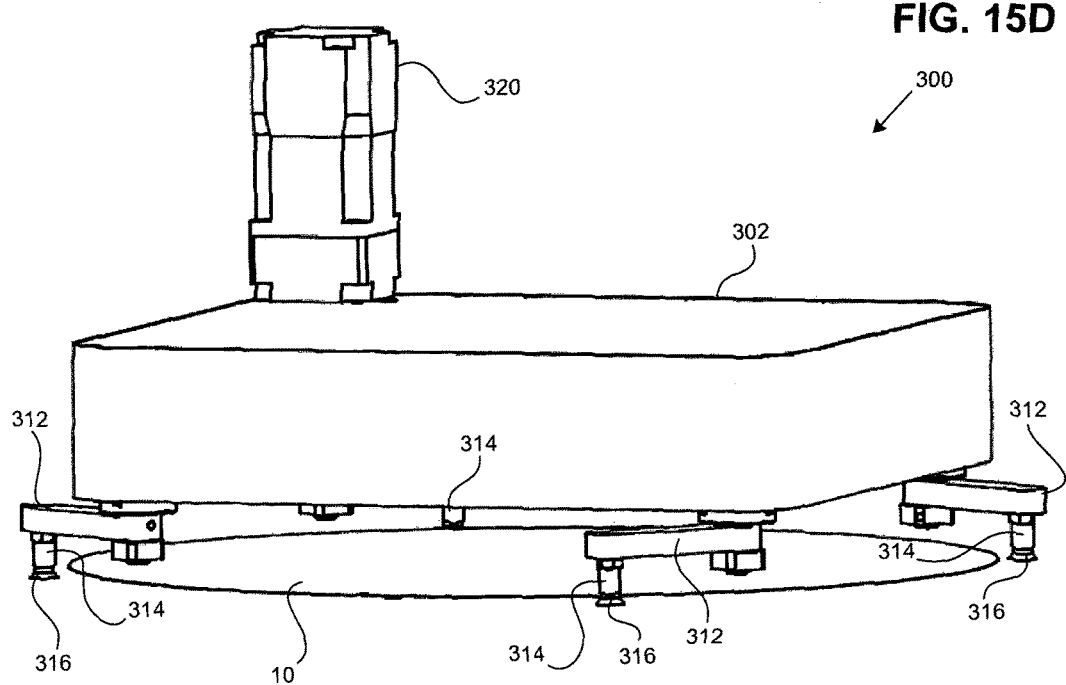
Figure 15E:
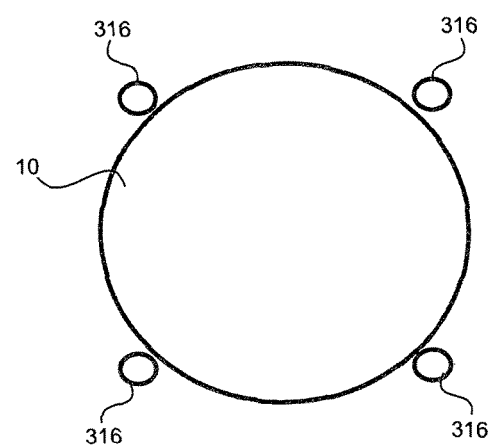

FIGS. 15D-15E are schematic illustrations of multifunction handling apparatus positioning of capture arms and capture arm tip elements relative to a wafer in a manner that limits or constrains lateral wafer displacement along a wafer table surface in accordance with an embodiment of the present disclosure.

Figure 16:
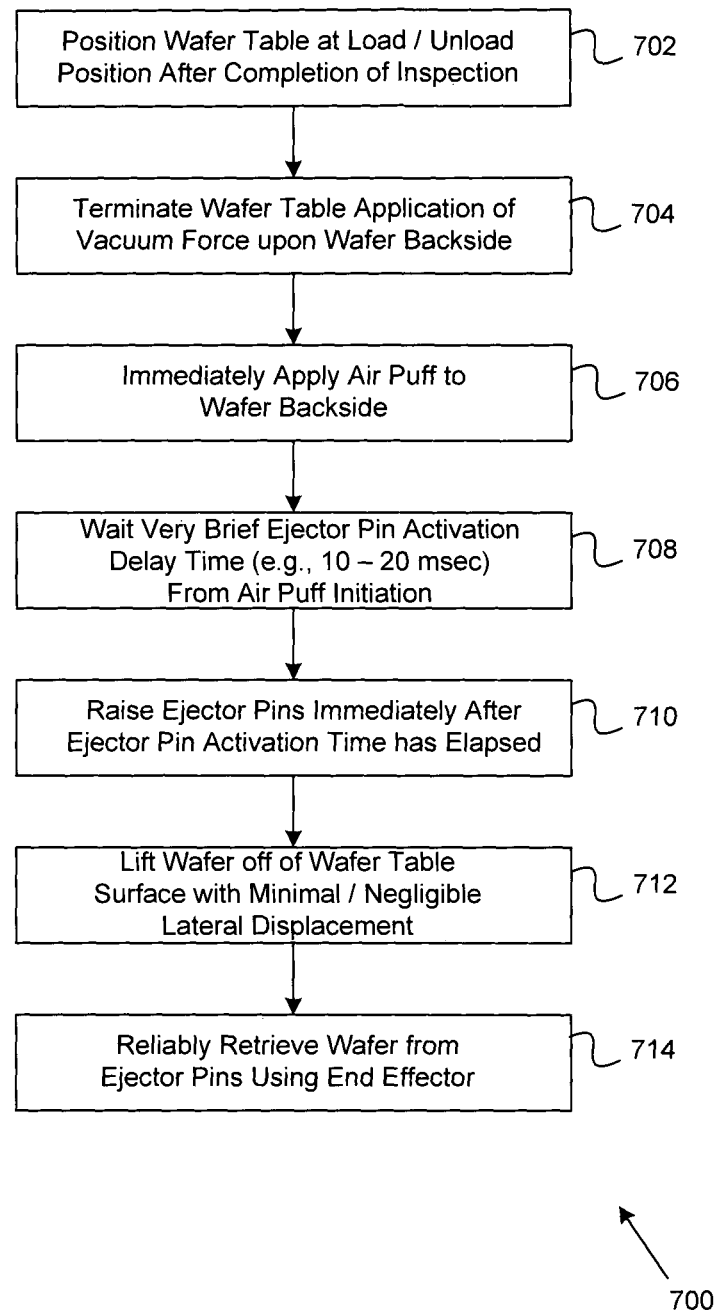

FIG. 16 is a flow diagram of a representative process for limiting, controlling, or preventing lateral wafer displacement along a wafer table surface in accordance with an embodiment of the present disclosure.

Figure 17:
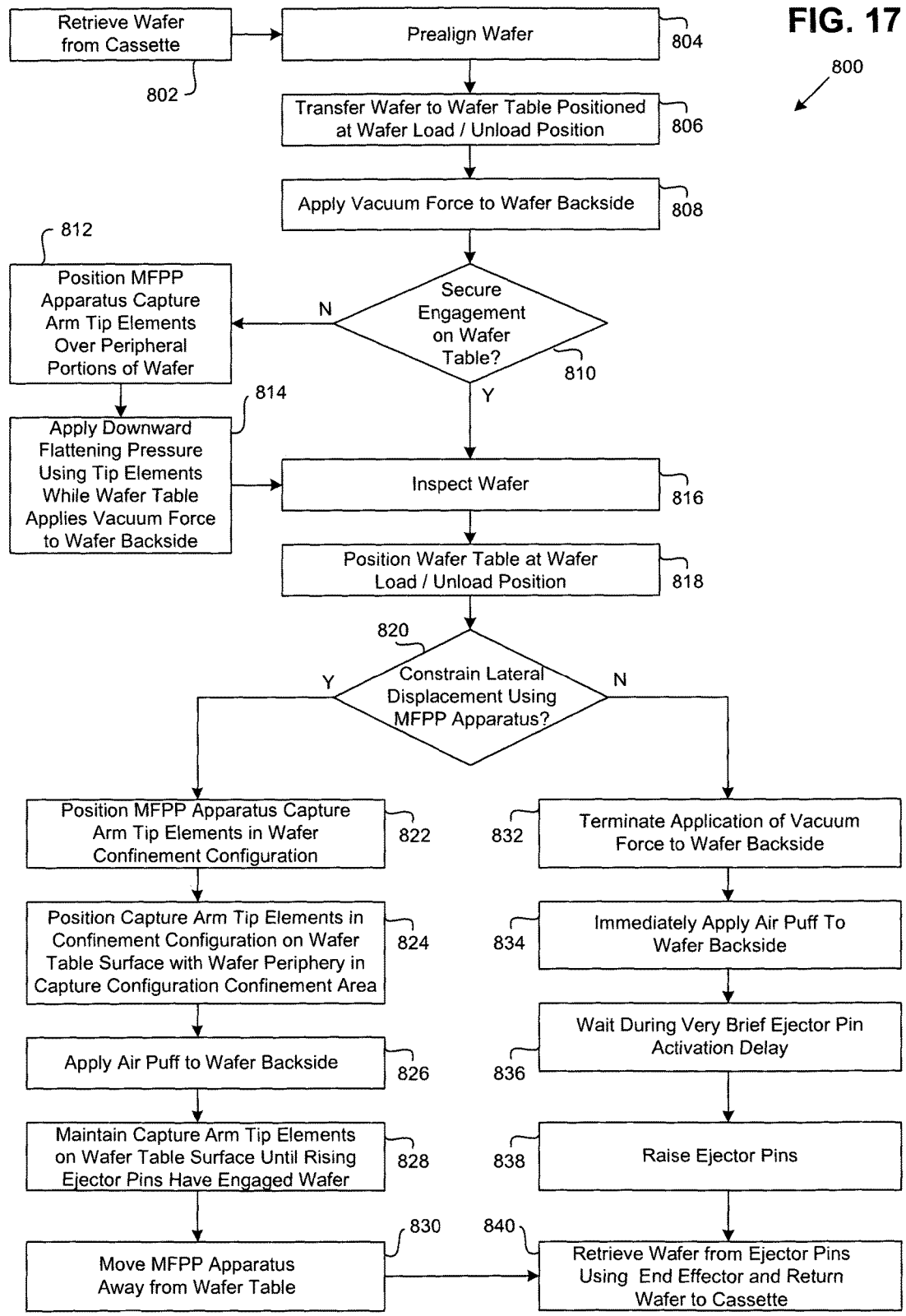

FIG. 17 is a flow diagram of a representative wafer handling process in accordance with an embodiment of the present disclosure.

Figure 18:
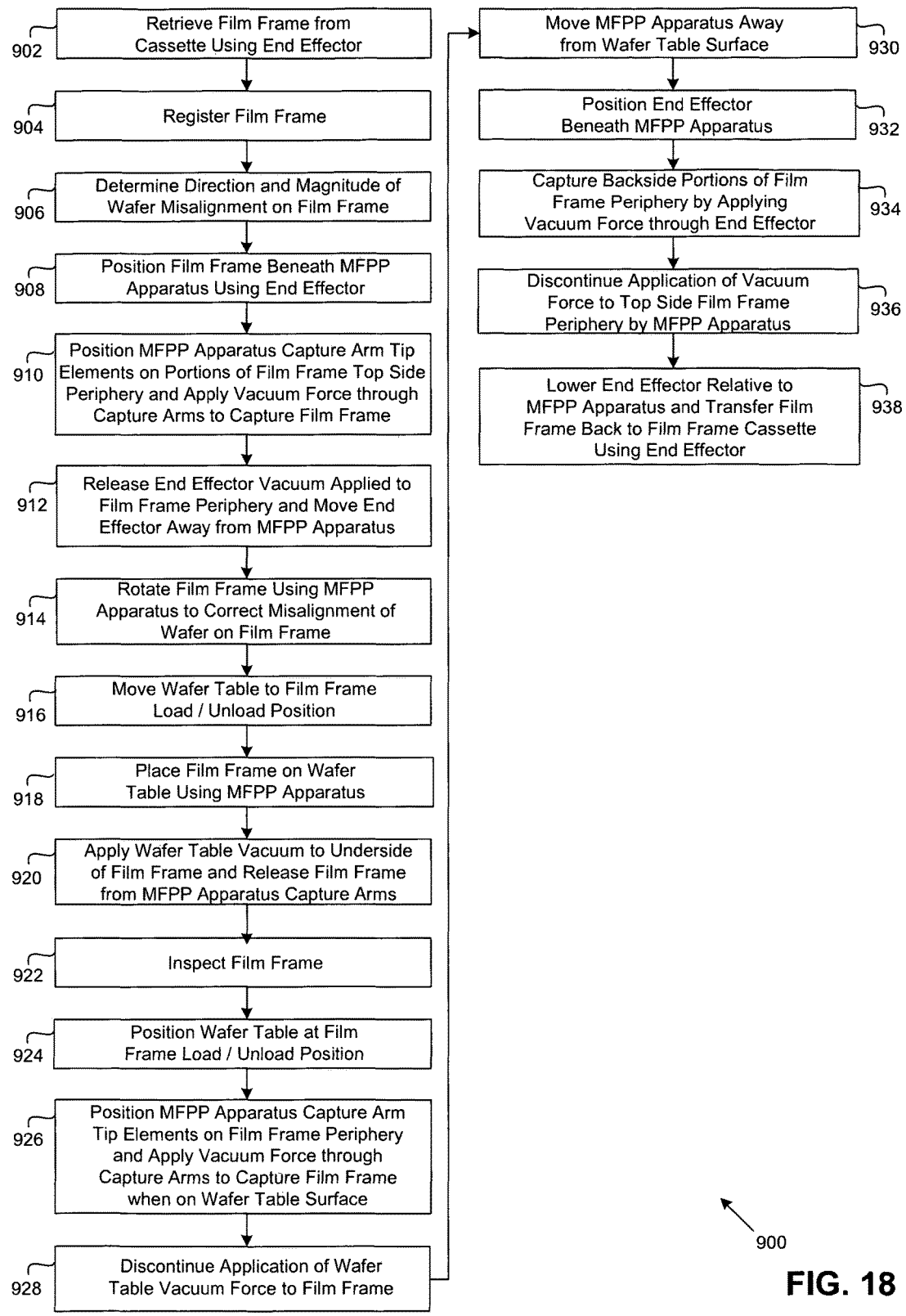

FIG. 18 is a flow diagram of a representative film frame handling process in accordance with an embodiment of the present disclosure.

DETAILED DESCRIPTION

In the present disclosure, depiction of a given element or consideration or use of a particular element number in a particular FIG. or a reference thereto in corresponding descriptive material can encompass the same, an equivalent, or an analogous element or element number identified in another FIG. or descriptive material associated therewith. The use of "/" in a FIG. or associated text is understood to mean "and/or" unless otherwise indicated. The recitation of a particular numerical value or value range herein is understood to include or be a recitation of an approximate numerical value or value range.

As used herein, the term "set" corresponds to or is defined as a non-empty finite organization of elements that mathematically exhibits a cardinality of at least 1 (i.e., a set as defined herein can correspond to a unit, singlet, or single element set, or a multiple element set), in accordance with known mathematical definitions (for instance, in a manner corresponding to that described in *An Introduction to Mathematical Reasoning: Numbers, Sets, and Functions*, "Chapter 11: Properties of Finite Sets" (e.g., as indicated on p. 140), by Peter J. Eccles, Cambridge University Press (1998)). In general, an element of a set can include or be a system, an apparatus, a device, a structure, an object, a process, a physical parameter, or a value depending upon the type of set under consideration.

For purpose of brevity and to aid understanding, the term the term "wafer" as used herein can encompass whole wafers, partial wafers, or other types of whole or partial objects or components (e.g., solar cells) having one or more planar surface areas upon which a set of optical inspection processes and/or other processing operations are desired or required. The term "film frame" in the description that follows generally refers to a support member or frame configured for carrying or supporting a wafer, a thinned or backlapped wafer, or a sawn wafer, for instance, by way of a thin layer or film of material that is disposed or stretched across a film frame surface area, and to which a wafer is mounted or adhered, in a manner understood by one of ordinary skill in the relevant art. Additionally, the term "wafer table" as used herein includes an apparatus for holding a wafer or a film frame during a wafer inspection process or a film frame inspection process, respectively, where the term "wafer table" will be understood by one of ordinary skill in the relevant art to be equivalent, substantially equivalent, or analogous to a wafer chuck, a vacuum table, or a vacuum chuck. The term "non-porous material" as used herein is intended to mean a material that is at least substantially or essentially impermeable to the flow or transfer of a fluid such as air or a liquid therethrough, and which is correspondingly at least substantially or essentially impermeable with respect to the communication or transfer of a vacuum force therethrough (e.g., relative to a given thickness or depth of the non-porous material, such as a depth greater than approximately 0.50-1.0 mm). Analogously, the term "porous material" is intended to mean a material that is at least moderately/substantially or essentially permeable to the flow or transfer of a fluid such as air or a liquid therethrough, and which is correspondingly at least moderately/substantially or essentially permeable with respect to the communication or transfer of a vacuum force therethrough (e.g., relative to a given thickness or depth of the porous material, such as a depth greater than approximately 0.50-1.0 mm). Finally, the terms "ceramic based" and "ceramic based material" in the context of the present disclosure are intended to mean a material that is entirely or substantially ceramic in its material structure and properties.

Embodiments in accordance with the present disclosure are directed to systems and processes for handling wafers and film frames, which provide (a) a single or unified porous wafer table configured for handling both wafers and film frames in a manner that facilitates or enables accurate, high throughput inspection processes; and (b) subsystems, devices, or elements configured for automatically (i) remediating insufficient vacuum retention of wafers upon the wafer table due to wafer warpage or non-planarity; (ii) preventing lateral displacement of wafers due to vacuum force cessation and/or air purge application; and/or (iii) correcting or compensating for rotational misalignment of wafers carried by film frames. Several embodiments in accordance with the present disclosure are directed to systems and processes that can provide each of the foregoing.

While multiple embodiments in accordance with the present disclosure are directed to wafer and film frame inspection systems (e.g., optical inspection systems), several embodiments in accordance with the present disclosure can additionally or alternatively be configured for supporting or performing other types of wafer and/or film frame front end or back end processing operations, such as test operations. Aspects of representative embodiments in accordance with the present disclosure are described in detail hereafter with primary emphasis on inspection systems for purpose of brevity and to aid understanding.

By way of a single or unified wafer table configured for handling both wafers and film frames, embodiments in accordance with the present disclosure eliminate the need for or exclude a wafer table conversion kit, thus eliminating production downtime due to wafer-to-film frame and film frame-to-wafer conversion kit changeover and calibration operations, thereby enhancing average inspection process throughput. A single or unified wafer table in accordance with an embodiment of the present disclosure facilitates or enables high accuracy inspection operations by providing a wafer table surface having a high or very high degree of planarity that maintains wafer die surfaces in a common inspection plane with minimal or negligible deviation therefrom along a direction parallel to a normal axis of the highly planar wafer table surface.

Additionally, embodiments in accordance with the present disclosure can eliminate the need for manual intervention that in the past was needed to address (a) lack of wafer retention upon a wafer table surface due to wafer warpage or non-planarity, and (b) unpredictable lateral motion of a wafer along a wafer table surface following the interruption or cessation of a vacuum force that retained the wafer to the wafer table surface and/or the momentary application of a puff of positive air to the underside of the wafer by the wafer table to remove any residual vacuum suction. Furthermore, embodiments in accordance with the present disclosure can eliminate the need for manual intervention or mechanically complex and undesirably expensive rotatable wafer table assemblies which in the past were required to correct rotational misalignment of a wafer relative to a film frame on which the wafer resides (e.g., when wafer misalignment relative to the film frame exceeded a given threshold misalignment magnitude).

Aspects of a Representative System Configuration and System Elements

Figure 1A:
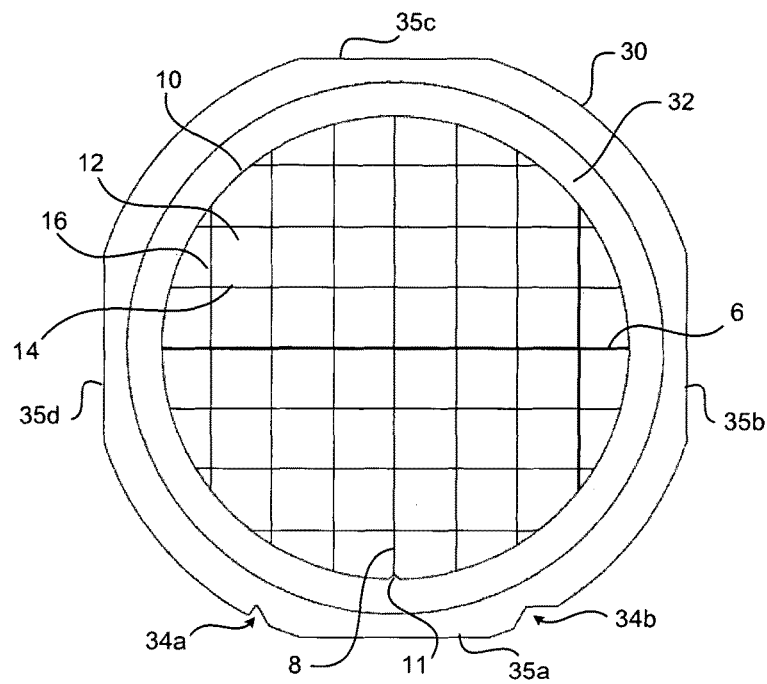
FIG. 1A is a schematic illustration of a wafer mounted on a film frame, which carries the wafer by way of a thin material layer or film that includes an adhesive or tacky side to which the wafer is mounted.
Figure 1B:
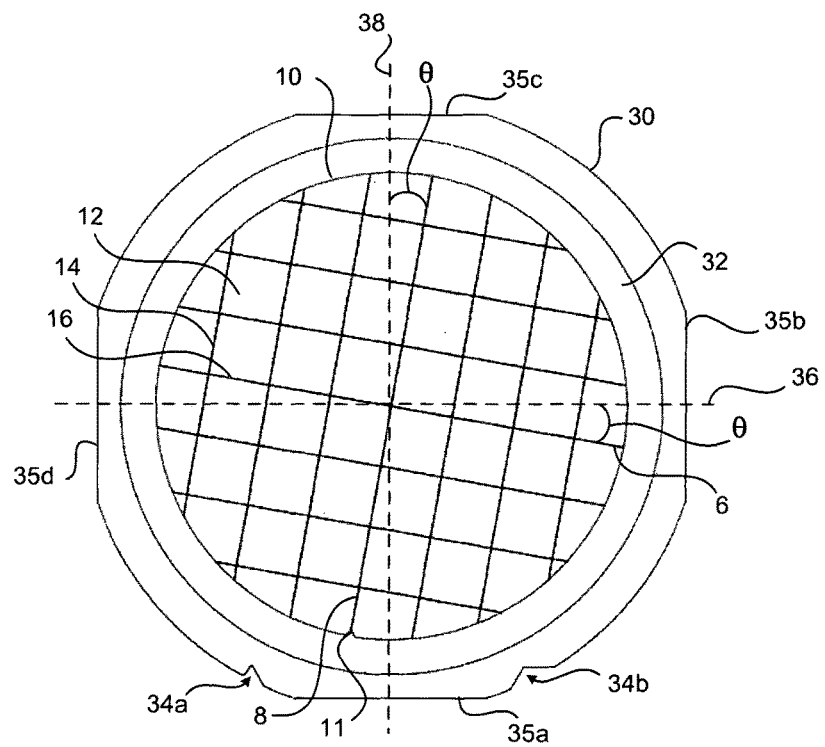
FIG. 1B is a schematic illustration of a wafer that is rotationally misaligned relative to a film frame that carries the wafer.
Figure 2A:
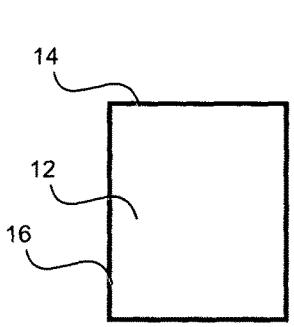
FIG. 2A is a schematic illustration of a die that is properly positioned or aligned relative to an image capture device field of view (FOV).
Figure 2A:
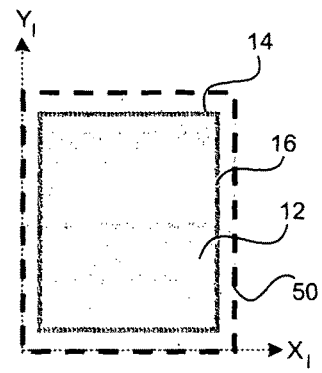
Figure 2B:
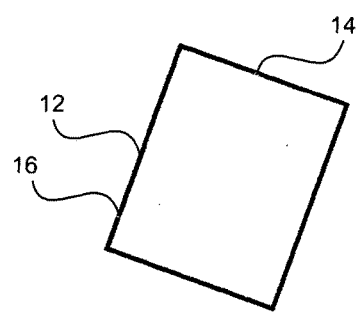
FIG. 2B is a schematic illustration of a die that is improperly positioned or misaligned relative to an image capture device FOV.
Figure 2B:
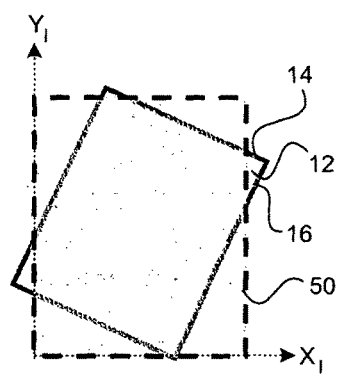
Figure 2C:
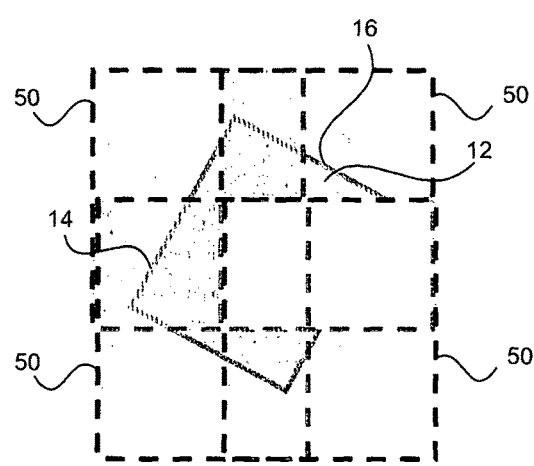
FIG. 2C is a schematic illustration indicating that up to four images may be required to capture the entire surface area of a rotationally misaligned die such as that shown in FIG. 2B, depending upon the extent of the die's misalignment relative to the FOV.
Figure 2D:
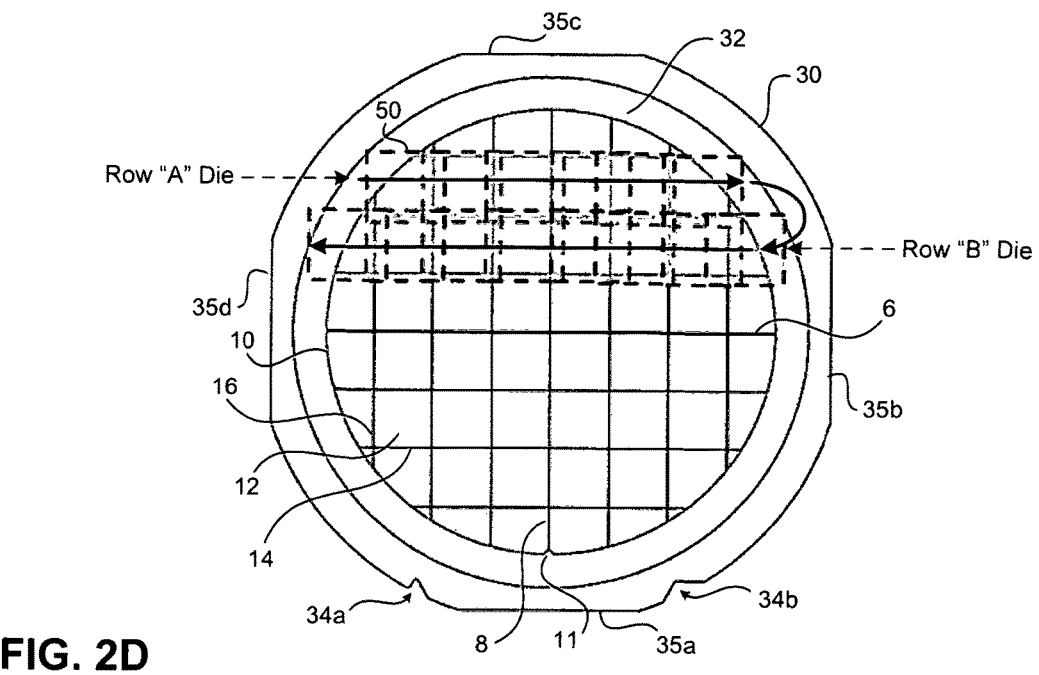
FIG. 2D is a schematic illustration of a wafer that is properly mounted on and aligned relative to a film frame, and an inspection process wafer travel path along which an image capture device captures an image of the entire surface area of each die within successive rows of die on the wafer.
Figure 2E:
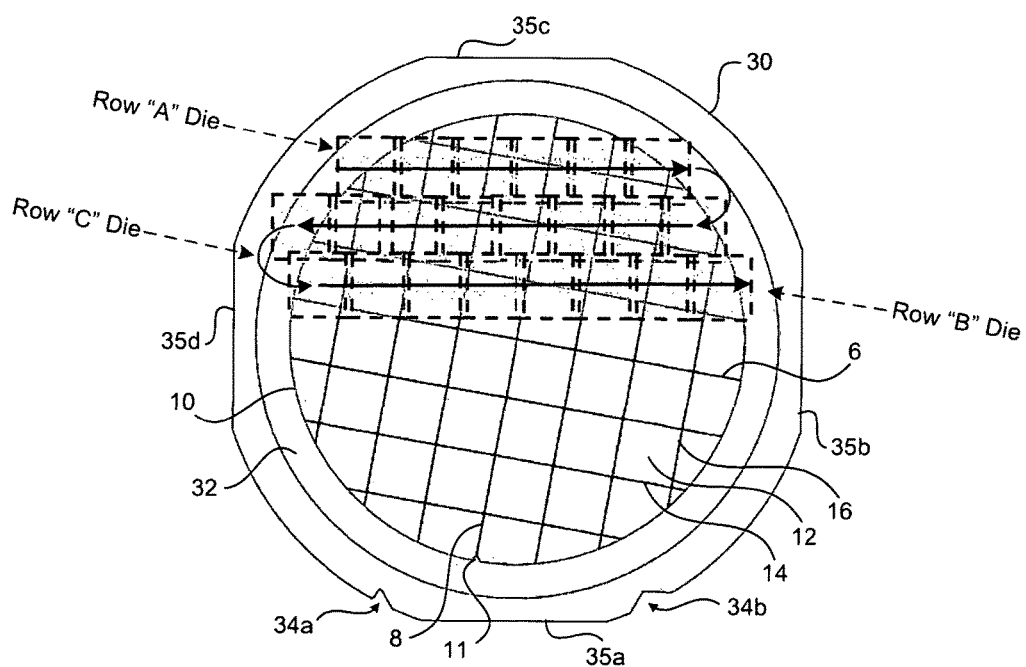
FIG. 2E is a schematic illustration of a wafer 10 that is rotationally misaligned relative to a film frame, and an inspection process wafer travel path along which an image capture device captures images of less than the entire surface area of each die within successive rows of die on the wafer.
Figure 2F:
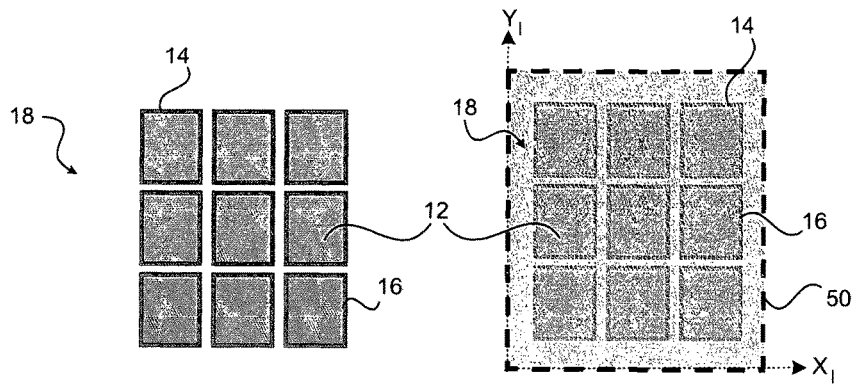
FIG. 2F is a schematic illustration of a die array in which the collective surface area of all die within the die array is smaller than an image capture device FOV, and the die array is properly aligned relative to the FOV because horizontal and vertical sides of each die within the die array are substantially parallel to FOV horizontal and vertical axes axis $X_I$ and $Y_I$, respectively.
Figure 2G:
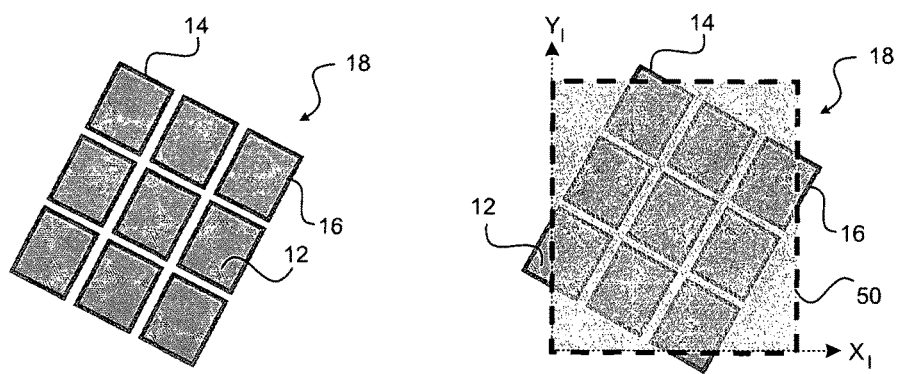
FIG. 2G is a schematic illustration of a die array for which the horizontal and vertical sides of the die within a die array are not properly aligned with respect to FOV horizontal and vertical axes $X_I$ and $Y_I$.
Figure 2H:
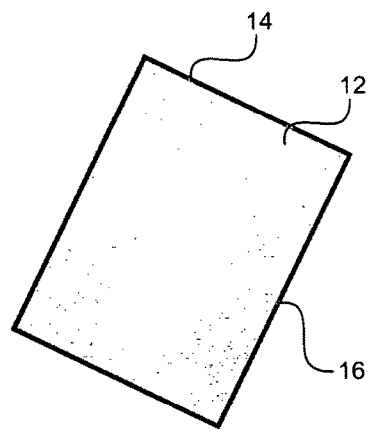
FIG. 2H is a schematic illustration of a single die having a surface area that is larger than an image capture device FOV, where the die is properly aligned relative to the FOV because the die's horizontal and vertical sides are substantially parallel to FOV horizontal and vertical axes $X_I$ and $Y_I$, respectively.
Figure 2H:
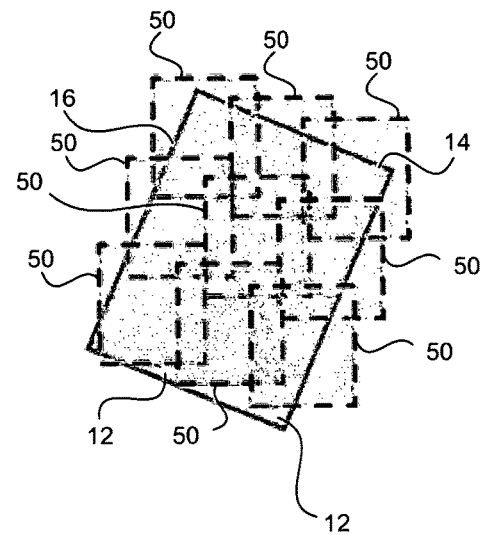
Figure 2I:
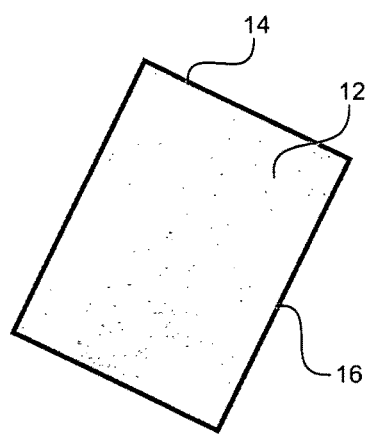
FIG. 2I is a schematic illustration of a single die such as that shown in FIG. 2H, for which die side misalignment relative to FOV horizontal and vertical axes $X_I$ and $Y_I$ results in portions of the die remaining outside of the image capture device FOV.
Figure 2I:
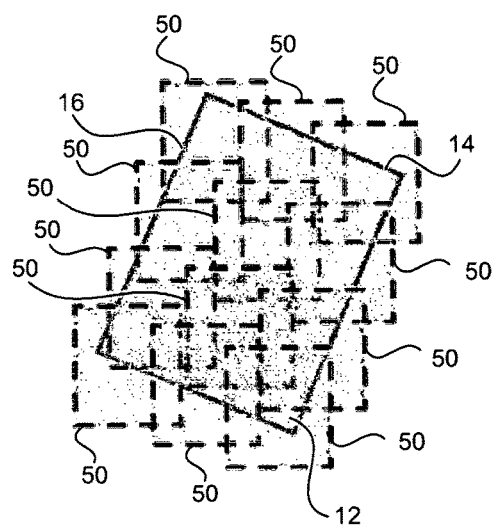
Figure 3A:
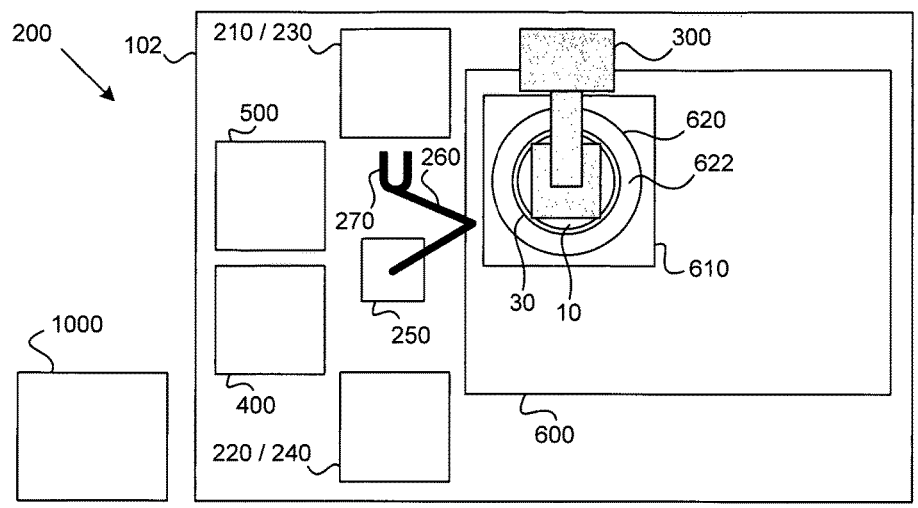
FIG. 3A is a schematic illustration showing portions of a wafer and/or film frame handling system providing a single porous wafer table structure for handling both wafers and film frames, and further providing rotational misalignment correction, non-planarity remediation, and/or lateral displacement prevention in accordance with an embodiment of the present disclosure.

FIG. 3A is a block diagram of a system 200 for handing wafers 10 and film frames 30 in accordance with an embodiment of the present disclosure, which includes a wafer table assembly 610 having a single or unified wafer table 620 which provides a high or very high planarity surface 622 configured for handling both wafers and film frames during inspection processes (e.g., wafer inspection processes and film frame inspection processes, respectively) by an inspection system 600. The system 200 further includes a first handling subsystem 250 and a second handling subsystem 300 which are configured for (a) conveying wafers 10 and film frames 30 to and from the inspection system 600, and (b) providing wafer-to-film frame rotational misalignment correction and wafer non-planarity remediation as part of pre-inspection handling operations, and lateral displacement prevention as part of post-inspection handling operations, as further detailed below.

Depending upon whether wafers 10 or film frames 30 are being inspected at a given time, the system 200 includes a wafer source 210 such as a wafer cassette, or a film frame source 230 such as a film frame cassette, respectively. Similarly, if wafers 10 are being inspected, the system 200 includes a wafer destination 220 such as a wafer cassette (or a portion of a processing station); and if film frames 30 are being inspected, the system 200 includes a film frame destination 240, which can be a film frame cassette (or a portion of a processing system). A wafer source 210 and a wafer destination 220 can correspond to or be an identical location or structure (e.g., the same wafer cassette). Similarly, a film frame source 220 and a film frame destination 240 can correspond to or be an identical location or structure (e.g., the same film frame cassette).

The system 200 also includes a wafer pre-alignment or alignment station 400 configured for establishing an initial or pre-inspection alignment of wafers 10 such that wafers 10 are properly aligned relative to the inspection system 600; a rotational misalignment inspection system 500 configured for receiving, retrieving, determining, or measuring a rotational misalignment direction and a rotational misalignment magnitude (e.g., which can be indicated by a rotational misalignment angle) corresponding to wafers 10 mounted upon film frames 30; and a control unit 1000 configured for managing or controlling aspects of system operation (e.g., by way of the execution of stored program instructions), as further detailed below. The control unit 1000 can include or be a computer system or computing device, which includes a processing unit (e.g., a microprocessor or microcontroller), a memory (e.g., which includes fixed and/or removable random access memory (RAM) and read-only memory (ROM)), communication resources (e.g., standard signal transfer and/or network interfaces), data storage resources (e.g., a hard disk drive, an optical disk drive, or the like), and a display device (e.g., a flat panel display screen).

In multiple embodiments, the system 200 additionally includes a support structure, base, underframe, or undercarriage 202 that is coupled to or configured for supporting or carrying at least the second handling subsystem 300 such that the second handling subsystem 300 can operatively interface with the first handling subsystem 250 and the processing system 600 to facilitate wafer or film frame handling operations. In some embodiments, the support structure 202 supports or carries each of the first handling subsystem 250, the second handling subsystem 300, the wafer alignment station 400, the misalignment inspection system 500, and the inspection system 600.

Figure 3B:
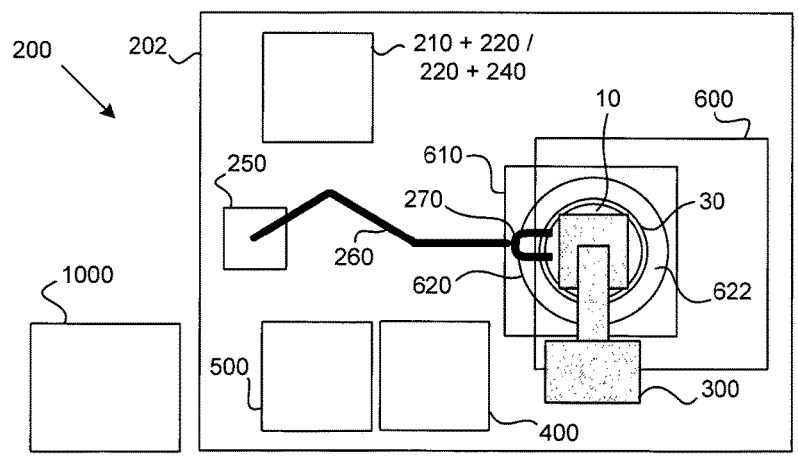
FIG. 3B is a schematic illustration showing portions of a wafer and/or film frame handling system providing a single porous wafer table structure for handling both wafers and film frames, and further providing rotational misalignment correction, non-planarity remediation, and/or lateral displacement prevention in accordance with an embodiment of the present disclosure.

FIG. 3B is a block diagram of a system 200 for handing wafers 10 and film frames 30 which provides a single or unified wafer table 620 configured for handling both wafers and film frames during inspection by an inspection system 600, and which further provides a first handling subsystem 250 and a second handling subsystem 300 in accordance with another embodiment of the present disclosure. In this embodiment, a wafer source 210 and a wafer destination 230 are identical, e.g., the same wafer cassette; and a film frame source 220 and a film frame destination 240 are identical, e.g., the same film frame cassette. Such an embodiment can provide a smaller or significantly reduced spatial footprint, resulting in a compact, space efficient system 200.

In a representative embodiment, the inspection system 600 is configured for performing 2D and/or 3D optical inspection operations upon wafers 10 and film frames 30. An optical inspection system 600 can include a number of illumination sources, image capture devices (e.g., cameras) configured for capturing images and generating image data sets corresponding thereto, and optical elements configured for some or each of directing illumination toward wafers 10, directing illumination reflected from wafer surfaces toward particular image capture devices, reflecting or optically affecting (e.g., filtering, focusing, or collimating) illumination incident upon and/or reflected from wafer surfaces, in a manner understood by one of ordinary skill in the relevant art. The optical inspection system 600 also includes or is configured for communication with a processing unit and a memory for analyzing image data sets by way of the execution of stored program instructions, and generating inspection results.

As previously indicated, the inspection system 600 can include or alternatively be another type of processing system at which one or more of the following are desired or required: (a) a wafer table 620 configured for handling wafers 10 and/or film frames 30, which provides a wafer table surface 622 having very high planarity for collectively maintaining wafer die 12 in a common plane during processing operations, with negligible planar deviation therefrom; (b) correct alignment of wafers 10 exhibiting an amount of misalignment relative to film frames 30 that exceeds a misalignment threshold magnitude (e.g., a maximum wafer-to-film frame rotational misalignment tolerance, which should or must be satisfied for maximum throughput inspection, such as further detailed below with reference to FIGS. 10A-10D); (c) uniform secure retention of wafers 10 or film frames 30, including non-planar or warped wafers 10, by the wafer table 620; and/or (d) prevention of unintended, unpredictable, or uncontrolled lateral wafer displacement along the wafer table surface 622.

Figure 3C:
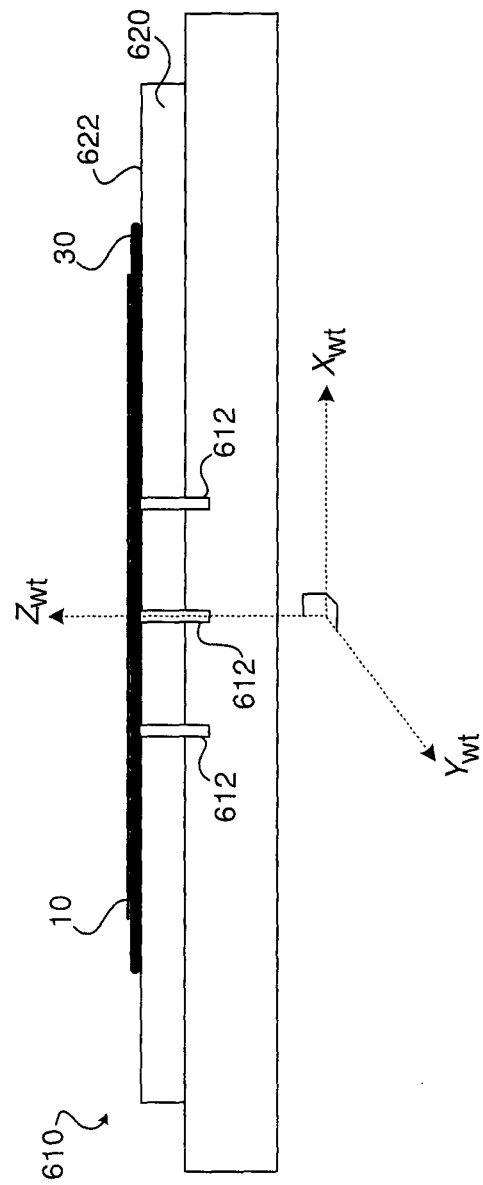
FIG. 3C illustrates a side view of the wafer table showing an axis Zwt defined normal to a midpoint of the wafer table surface and transverse axes Xwt and Ywt defining a plane, each of axes Xwt and Ywt being transverse to axis Zwt in accordance with an embodiment of the present disclosure.

With further reference to FIG. 3C, the wafer table 620 carried by the wafer table assembly 610 provides a highly planar external or exposed wafer table surface 622 upon which wafers 10 as well as film frames 30 can be positioned and securely held or retained, such that wafer die 12 are collectively maintained in a common inspection plane with minimum or negligible planar deviation therefrom, along a direction parallel to a normal axis $Z_{wt}$ of the highly planar wafer table surface 622 defined normal to a midpoint, center, centroid, or approximate midpoint, center, or centroid of the wafer table surface 622. The wafer table assembly 610 is configured for selectively and controllably displacing the wafer table 620, and hence any wafer 10 or film frame 30 carried or securely held thereby, along two transverse spatial axes corresponding to or defining a plane, for instance, wafer table x and y axes $X_{wt}$ and $Y_{wt}$, respectively, each of which is also transverse to axis $Z_{wt}$.

The wafer table 620 is configured for selectively and securely holding or retaining wafers 10 or film frames 30 upon or against the wafer table surface 622 by way of (a) an inherent or natural suction force that exists due to a pressure differential between atmospheric pressure acting upon the wafer's top, upper, or exposed surface and the wafer's bottom or underside, in combination with (b) the selectively controlled application of vacuum force or negative pressure to the underside of the wafer 10. The wafer table 620 can further be configured for applying or delivering a brief/momentary, e.g., approximately 0.50 second, or 0.25-0.75 second, spurt of positive air pressure, e.g., an air purge or air puff, to an interface between the wafer table surface 622 and the underside of wafers 10 or film frames 30 to facilitate the release of vacuum suction acting on the wafers 10 or film frames 30 from the wafer table surface 622 following the interruption or cessation of an applied vacuum force.

In various embodiments, the wafer table assembly 610 includes a set of ejector pins 612 that can be selectively and controllably displaced in a perpendicular or vertical direction relative to the wafer table surface 622, parallel to or along the wafer table z axis $Z_{wt}$ for vertically displacing wafers 10 or film frames 30 relative to the wafer table surface 622. In multiple embodiments, the wafer table 620 includes a single set of ejector pins 612 (e.g., three ejector pins) configured for handling wafers 10 of multiple standard sizes, such as 8, 12, and 16 inch wafers 10. The wafer table 620 need not include, and can omit or exclude, additional sets of ejector pins 612 (e.g., additional sets of three ejector pins), due to the positioning of the single set of ejector pins 612 upon the wafer table 620 (e.g., positioned to carry 8-inch wafers somewhat near, generally near, near, or proximate to their periphery) and the manner in which wafers and film frames are handled in accordance with embodiments of the present disclosure. As further detailed below, in several embodiments, while ejector pins 612 can be used in association with the transfer of wafers 10 to and from the wafer table 620, the transfer of film frames 30 to and/or from the wafer table 620 need not involve, and can omit or entirely exclude, the use of ejector pins 612.

In multiple embodiments, the wafer table 620 has a structure that is identical, essentially identical, substantially identical, or analogous to a wafer table structure described hereafter with reference to FIGS. 4A-FIG. 9.

Aspects of a Representative Unified Wafer Table Structure for Wafer and Film Frame Handling In embodiments in accordance with the present disclosure, a wafer table structure can include a base tray (or base receptacle, frame, form, repository, or reservoir structure) having a number of ridges (which can include or be protrusions, ridges, raised strips, partitions, corrugations, creases, or folds) formed integrally from or attached to an interior or base surface of the wafer table structure (e.g., the bottom of base tray). In various embodiments, the base tray can includes at least one type of non-porous material, such as a ceramic based material. The base tray is intended to be gas or fluid (e.g., air) impermeable, or essentially gas or fluid impermeable, in response to application of vacuum force(s). That is, the non-porous material is intended to be impervious or essentially impervious to the passage of gas, fluid, or vacuum force(s) therethrough in response to applied vacuum force(s). The non-porous material is further intended to be easily or readily machinable, grindable, or polishable by ordinary techniques and equipment, such as conventional polishing wheels. In multiple embodiments, the non-porous material can include or be porcelain.

The ridges define, delineate, divide, or separate the base tray into multiple compartments, chambers, cell structures, open regions, or recesses into which at least one type of moldable, formable, conformable, or flowable porous material can be introduced, provided, deposited, or poured and cured, solidified, or hardened. The porous material can further be securely bonded (e.g., chemically bonded, such as in association with a hardening, solidification, or curing process) or adhered to the base tray compartments, such that the hardened porous material is securely retained within or joined to the compartments. Additionally or alternatively, the ridges can be shaped in such a way such that the porous material when hardened or cured within the compartments is secured or retained therein by the structure of the ridges. The ridges can be structured to include curved and/or overhanging portions, or take other suitable shapes, as desirable or required.

The porous material in the compartments is intended to permit the passage of gas or fluid (e.g., air) in response to the application of vacuum force(s) thereto, such that gas, fluid, or vacuum force(s) can be communicated or transmitted therethrough (e.g., after it has been cured or hardened, and vacuum force(s) are applied thereto). Furthermore, the porous material is intended to be easily or readily machinable, grindable, or polishable by ordinary techniques and equipment, such as conventional polishing wheels.

The choice of non-porous base tray material(s), and/or porous material(s) for introduction into base tray compartments, for the wafer table structure depends upon the desired or required characteristics of the wafer table structure in relation to the application or process that is to be carried out on a wafer 10 or film frame 30 residing thereon. For instance, optical inspection of small or ultra-small die 12 on large diameter sawn wafers 10 carried by film frames 30 requires that the wafer table structure provide a wafer table surface having a very high or ultra-high degree of planarity. Moreover, the choice of non-porous base tray material(s) and/or porous compartment material(s) can depend upon the chemical, electrical/magnetic, thermal, or acoustic requirements that the wafer table structure should meet in view of the expected or intended types of wafer or film frame processing conditions to which the wafer table structure will be exposed.

In various embodiments, the non-porous base tray material(s) and the porous compartment material(s) are selected based on material characteristic(s) or quality(ies) that will facilitate or enable the grinding or polishing across multiple exposed surfaces of at least two distinguishable or different materials by a single grinding or polishing apparatus (e.g., substantially or essentially simultaneously). More particularly, exposed surfaces of the two (or more) distinguishable or different non-porous and porous materials can be simultaneously machined, grinded, or polished in the same or an identical manner, such as by way of a single, common, or shared process that involves standard machining, grinding, or polishing equipment operating or operated in accordance with standard machining, grinding, or polishing techniques. Such machining, grinding, or polishing of each of the non-porous and porous materials results in low, minimal, or negligible damage to machining, grinding, or polishing elements, devices, or tools such as polishing heads. Furthermore, in a number of embodiments, the non-porous base tray material(s) and porous compartment material(s) are selected such that a rate at which the non-porous base tray material(s) are affected (e.g., planarized) by such machining, grinding, or polishing and the rate at which the porous compartment material(s) is/are affected (e.g., planarized) by such machining, grinding, or polishing are substantially or essentially identical.

For purpose of brevity and ease of understanding, in the representative embodiments of wafer table structures described below, the non-porous base tray material includes or is a non-porous ceramic based material, and the porous compartment material includes or is a porous ceramic based material. One of ordinary skill in the relevant art will understand that a wafer table structure in accordance with an embodiment of the present disclosure is not limited to the material types provided in relation to the representative embodiments described below.

When the creation of a very flat, highly planar, or ultra-planar wafer table surface is desired or required, the porous material can include a moldable porous based ceramic material and/or other chemical compound which is suitable for forming, fabricating, or manufacturing a porous wafer table, wafer chuck, vacuum table, or vacuum chuck in accordance with standard/conventional processing techniques, processing sequences and processing parameters (e.g., hardening temperatures or temperature ranges, and corresponding hardening times or time intervals), in a manner understood by one of ordinary skill in the relevant art. In multiple embodiments, the porous material can include or be a commercially available material provided by CoorsTek (CoorsTek Inc., Hillsboro, Oreg. USA, 503-693-2193). Such a porous material can include or be one or more types of ceramic based materials, such as Aluminum Oxide (Al2O3) and Silicon Carbide (SiC), and can exhibit a post-hardened/post-cured pore size between approximately 5-100 µm (e.g., about 5, 10, 30, or 70 µm), and a porosity ranging between approximately 20-80% (e.g., about 30-60%). The pore sizes of the porous compartment material(s) can be selected based upon application requirements, such as an intended or desired level of vacuum force suitable for an application under consideration (e.g., the inspection of thin or very thin wafers 10 on film frames 30), as will be understood by one of ordinary skill in the art. Exposed, upper, or outer surfaces corresponding to portions of the ceramic base tray (e.g., the set of ridges, and possibly an outer base tray border) and hardened moldable porous ceramic material carried by base tray compartments can be machined (e.g., by way of a unified or single machining or polishing process) to provide a common wafer table surface exhibiting a very high or ultra-high degree of planarity or planar uniformity, which is suitable for securely retaining wafers or film frames in a manner that effectively disposes or maintains the wafer die surfaces along or within a common plane (perpendicular to the normal axis of the wafer table surface) with minimal or negligible deviation therefrom, e.g., during inspection.

FIG. 4A is a perspective view of a ceramic based base tray 100, and FIG. 4B is a perspective cross sectional view of the base tray of FIG. 4A, taken through line A-A', in accordance with an embodiment of the disclosure. As indicated above, in various embodiments the ceramic based base tray 100 is non-porous or, essentially non-porous, and hence is impervious or essentially impervious with respect to gas, fluid, or vacuum force transfer therethrough in response to applied vacuum force(s). That is, the ceramic based base tray 100 is typically intended to serve as a strong, very strong, or effectively impenetrable barrier relative to the communication or transfer of gas, fluid, or vacuum force(s) therethrough.

In an embodiment, the base tray 100 has a shape that defines a center or centroid 104, relative to or surrounding which a vacuum opening 20 can be disposed; a planar or transverse spatial extent or area $A_T$; an outer periphery or border 106; a plurality of inner bottom surfaces 110a-c, which can include a number of vacuum openings 20 disposed therein; and one or more ridges 120a-b disposed between the base tray's center and its outer border 106 (e.g., in an annular or concentric arrangement). As further detailed below, in various embodiments the ridges 120a-b, as well as the base tray's outer border 106, are sized, shaped, and/or dimensioned in a manner correlated with or corresponding to standard wafer and/or film frame sizes, shapes, and/or dimensions (e.g., 8-inch, 12-inch, and 16-inch wafers, and one or more film frame sizes corresponding to such wafer sizes). The base tray 100 further includes at least one underside surface 150, significant portions or the entirety of which in a number of embodiments are disposed or substantially disposed in a single base tray underside plane.

In several embodiments, a vertical base tray axis $Z_T$ can be defined perpendicular or substantially perpendicular to the base tray's underside surface 150 and the base tray's inner bottom surfaces 110a-c, and extending through the base tray's center or centroid 104. As will be understood by one of ordinary skill in the relevant art, the vertical base tray axis $Z_T$ is defined perpendicular to an intended wafer table planar surface upon or against which a wafer or film frame can be securely held or retained. In FIGS. 4A and 4B, $Z_T$ can be perpendicular to the line A-A', which bisects each vacuum opening 20.

Each ridge 120a-b borders inner bottom surfaces 110a-c of the base tray 100, and each ridge 120a-b delineates, separates, or partitions portions of different base tray inner bottom surfaces 110a-c from each other to define a set of base tray compartments or receptacles 130a-b that can receive or carry the aforementioned moldable, formable, conformable, or flowable porous material. More particularly, in the embodiment shown in FIG. 4A, a first ridge 120a extends above and surrounds (e.g., concentrically surrounds) a first inner bottom surface 110a of the base tray 100. A contiguous or generally contiguous structural recess defined by the first ridge 120a surrounding or encircling the first inner bottom surface 110a thereby defines a first base tray compartment or receptacle 130a, which has as its bottom surface the first inner bottom surface 110a. In an analogous manner, the first ridge 120a and the second ridge 120b extend above a second inner bottom surface 110b of the base tray 100. The second ridge 120b encloses the first ridge 120a (e.g., the first and second ridges 120a-b are concentric relative to each other), such that the first and second ridges 120a-b define a second contiguous or generally contiguous base tray compartment or receptacle 130b having as its bottom surface the second inner bottom surface 110b. Also analogously, the base tray's outer border 106 encloses the second ridge 120b (e.g., the second ridge 120b and the outer border 106 are concentric relative to each other), such that they define a third contiguous or generally contiguous base tray compartment or receptacle 130c having as its bottom surface the third inner bottom base tray surface 110c. Any given ridge 120 has a transverse ridge width, for instance, approximately 1-4 mm (e.g., approximately 3 mm); and a corresponding ridge depth, for instance, approximately 3-6 mm (e.g., approximately 4 mm) which defines the depth of a compartment or receptacle 130. As further described below, in various embodiments, any given base tray compartment or receptacle 130a-c has a spatial extent, planar surface area, or diameter that is correlated with or corresponds to the spatial extent, planar surface area, or diameter of standard wafer and/or film frame sizes, shapes, and/or dimensions.

Similar or analogous considerations to the foregoing apply to the definition of additional or other types of base tray compartments or receptacles 130 in alternate embodiments, including embodiments having a single ridge 120; embodiments having more than two ridges 120a-b; and/or embodiments in which portions of one or more ridges 120 do not fully enclose one another, or are not annular/concentric with respect to one or more other ridges 120 (e.g., when portions of a particular ridge 120 are transversely, radially, or otherwise disposed with respect to another ridge 120). The manner in which ridges 120 exhibiting various shapes, sizes, dimensions, and/or segments (e.g., a ridge 120 can include multiple distinct or separate segments or sections disposed with respect to an elliptical, circular, or other type of geometric outline or pattern) can define different types of base tray compartments or receptacles 130 will be readily understood by one of ordinary skill in the relevant art.

In addition to the foregoing, the base tray's outer border 106 as well as each ridge 120a-b respectively includes an exposed outer border upper surface 108 and an exposed ridge upper surface 122a-b, corresponding to an upper surface or upper side of the base tray 100 that, relative to the base tray's underside surface 150, is intended to be closest to a wafer 10 or film frame 30 carried by a wafer table planar surface. In multiple embodiments, a vertical distance (e.g., parallel to the base tray's central transverse axis $Z_T$) between the base tray's outer border upper surface 108 and the base tray's inner bottom surfaces 110a-c, as well as between each ridge upper surface 122a-b and the base tray's inner bottom surfaces 110a-c, defines a base tray compartment depth $D_{TC}$. A vertical distance between the base tray's outer border upper surface 108 and the base tray's underside surface 150 defines an overall base tray thickness. $T_{OT}$. Finally, a vertical distance along which a vacuum opening 20 extends can define a vacuum passage depth $D_V$, which is equal to the difference between $T_{OT}$ and $D_{TC}$.

Figure 5A:
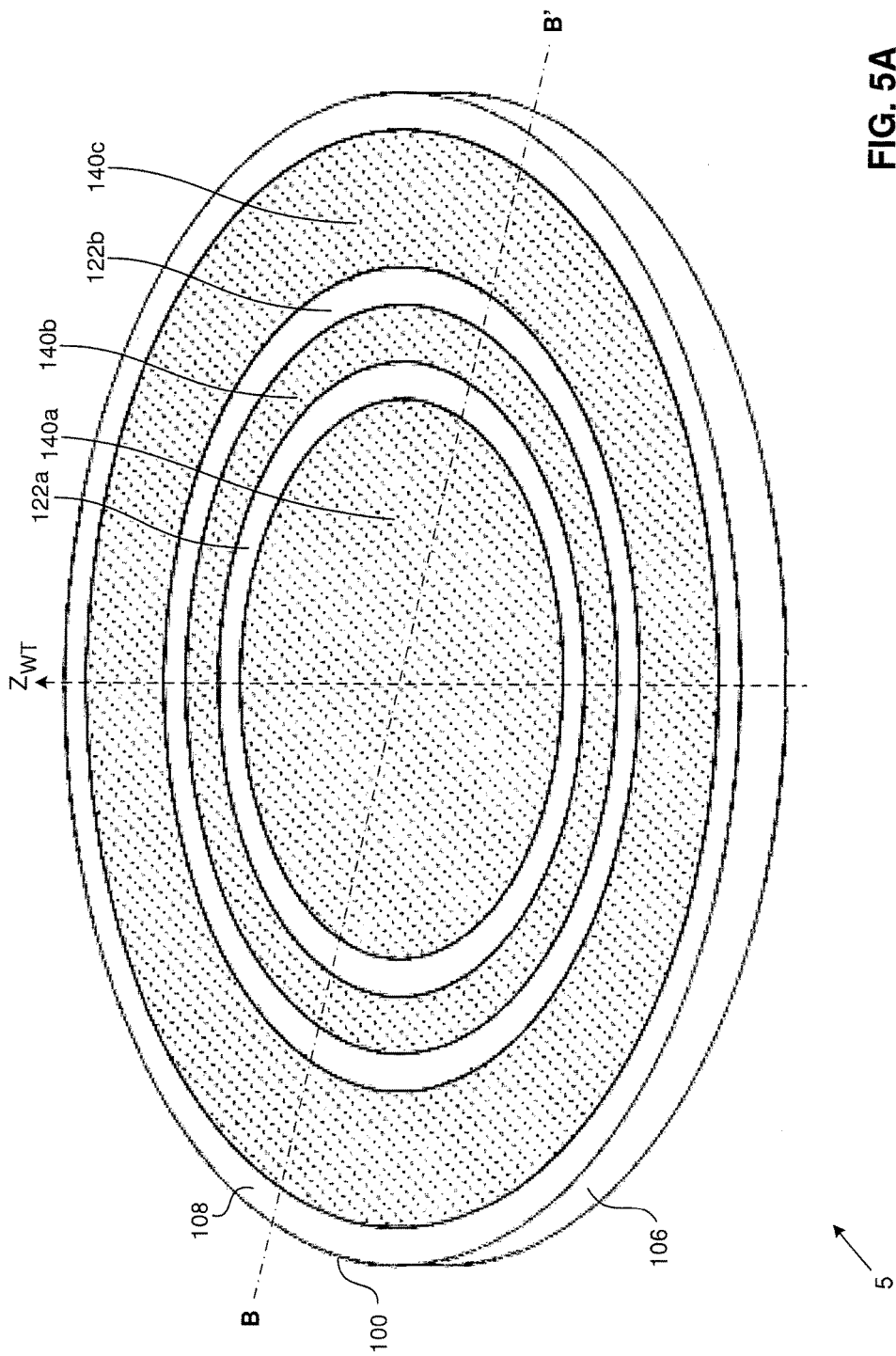
FIG. 5A is a perspective view of the base tray of FIG. 4A into which a moldable, formable, conformable or flowable porous material, such as a ceramic based porous material, has been disposed.
Figure 5B:
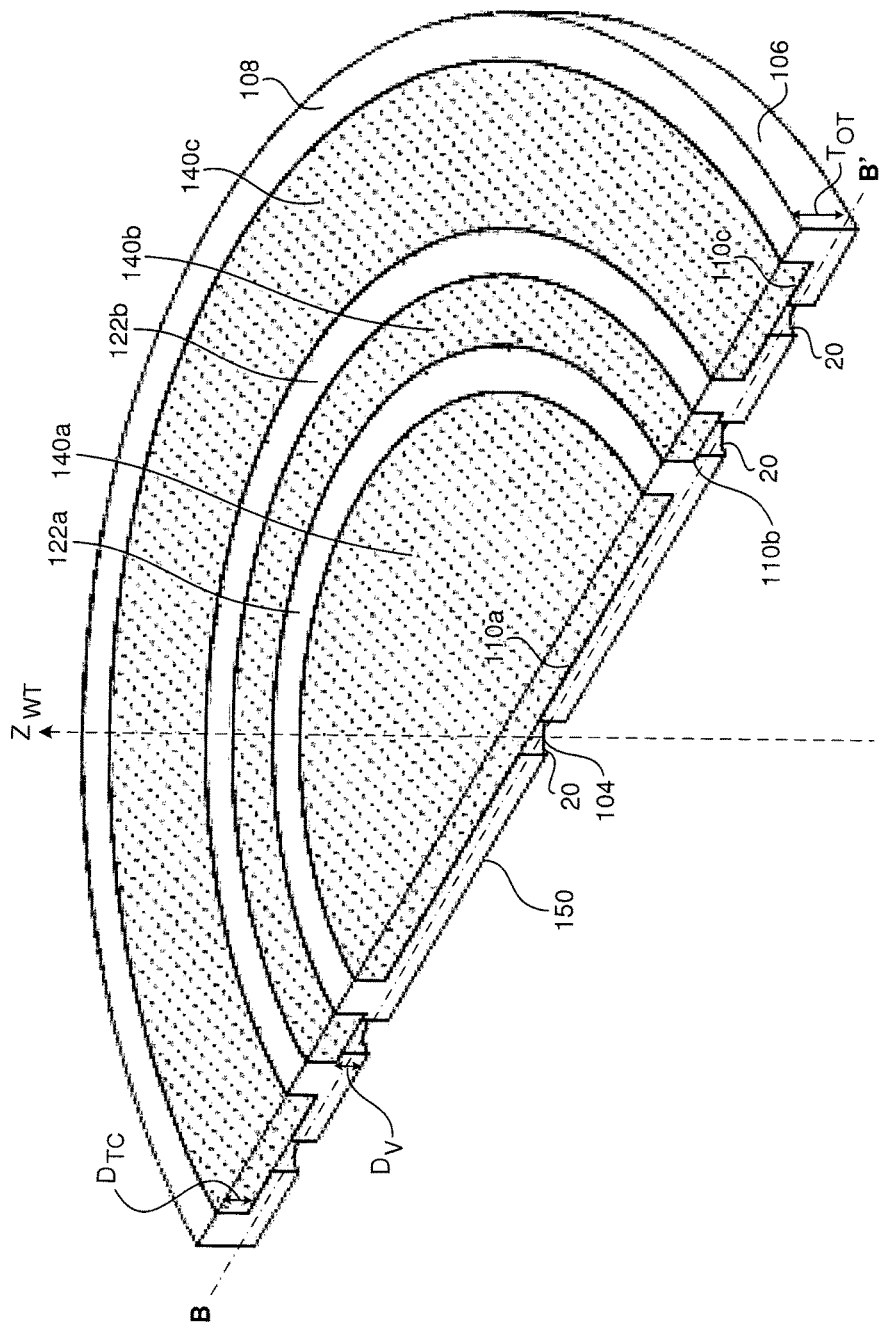
FIG. 5B is a perspective cross sectional view of the base tray carrying the moldable, formable, conformable, or flowable porous ceramic based material corresponding to FIG. 5A, taken through a line B-B'.

FIG. 5A is a perspective view of the base tray 100 of FIG. 4A into which a moldable, formable, conformable, or flowable porous material has been introduced, disposed, or provided to effectively provide the basis for, facilitate or effectuate the formation of, or form a wafer table structure 5 in accordance with an embodiment of the present disclosure. FIG. 5B is a perspective cross sectional view of the base tray 100 carrying the porous material corresponding to FIG. 5A, taken through the line B-B'. FIG. 5C is a cross sectional view of the base tray 100 carrying the porous material corresponding to FIGS. 5A and 5B.

In FIGS. 5A and 5B, the porous material can be considered to be resident within the base tray compartments 130a-c in a pre-hardened/pre-set or post-hardened/post-set state, depending upon a stage of wafer table structure fabrication under consideration. Furthermore, if considered in a post-hardened/post-set state, the porous material and the non-porous or vacuum impervious ceramic based base tray 100 can be considered in a pre-planarized/pre-machined or post planarized/post-machined state, once again depending upon a wafer table structure fabrication stage under consideration. Stages of a representative wafer table structure fabrication process in accordance with an embodiment of the present disclosure are described in detail below.

In view of FIGS. 5A-5C and relative to the base tray embodiment shown in FIGS. 4A and 4B, following the introduction, placement, deposition, or provision of the porous material into the base tray compartments 130a-c and the conformation of the porous material to the internal geometry of the base tray compartments 130a-c, the first base tray compartment 130a is filled by a first volume 140a of porous material; the second base tray compartment 130b is filled by a second volume 140b of porous material; and the third base tray compartment 130c is filled by a third volume 140c of porous material. Analogous or similar considerations apply to other base tray embodiments having different numbers and/or configurations of compartments 130. That is, after the porous material has been introduced into base tray compartments 130, each of such compartments 130 is filled with a given volume 140 of the porous material corresponding to the dimensions or volumetric capacity of any given compartment 130 under consideration. An initial volume 140 of porous material introduced into any given base tray compartment 130 should equal or exceed the compartment's volume, such that excess porous material can be machined or polished away in association with a planarization process, as further detailed below.

After the introduction of the porous material into a compartment 130, portions of any given volume 140 of porous material are exposed to a number of vacuum openings 20 within the compartment 130. More particularly, within a given volume 140 of porous material, porous material that interfaces with a base tray inner bottom surface 110 are selectively exposed to one or more vacuum openings 20 disposed or formed within a corresponding base tray inner bottom surface 110. For instance, as more particularly indicated in the embodiment shown in FIGS. 5B and 5C, the first volume 140a of porous material is exposed to the vacuum opening 20 disposed at the center of the base tray 100 within the first inner bottom surface 110a of the first base tray compartment 130a. Analogously, the second volume 140b of porous material is exposed to the vacuum openings 20 disposed within the second inner bottom surface 110b of the second base tray compartment 130b; and the third volume 140c of porous material is exposed to the vacuum openings 20 disposed within the third inner bottom surface 110c of the third base tray compartment 130c. Because each volume 140a-c of porous material is exposed to a corresponding set of vacuum openings 20, vacuum force(s) can be selectively communicated, distributed, or transferred through each volume 140a-c of porous material, to the upper surface of the porous material corresponding to the upper surface of the wafer table structure 5. Hence, when the wafer table structure 5 carries a wafer 10 or film frame 30 of a particular size or shape upon a planar wafer table surface, vacuum force(s) can be selectively communicated or transferred to the underside of a wafer 10 or film frame 30 through the corresponding base tray compartments covered by the wafer 10 or film frame 30 disposed upon a wafer table planar surface, as further elaborated upon below.

As indicated above and further elaborated upon below, after the porous material volumes 140 have been introduced into the base tray compartments 130, each such volume 140 can be hardened, solidified, or cured and bonded (e.g., collectively, in association or simultaneous with a hardening/bonding process) to an interior bottom surface 110 and associated side surfaces or sidewalls of one or more ridges 120 that define a compartment 130. Additionally, following a hardening/bonding process, exposed upper surfaces of the wafer table structure 5, which include exposed upper surfaces of the volumes 140 of porous material, exposed ridge upper surfaces 122, and the exposed outer border upper surface 108 can be simultaneously machined, polished, or planarized by way of one or more conventional, technologically simple, inexpensive, and robust machining or polishing techniques or processes using a single machining, grinding, or polishing apparatus across two distinguishable or different material surfaces. Furthermore, the use of single machining, grinding, or polishing apparatus gives rise to, provides, or defines a wafer table planar surface that exhibits a very high or ultra-high degree of planar uniformity. As a result, die 12 carried by a wafer 10 or film frame 30 disposed and securely held or retained upon the wafer table planar surface are maintained in a common plane in a manner that effectively maintains the upper or exposed die surfaces in said common plane with minimal or negligible deviation therefrom, even for very small die and/or very thin wafers. The upper surfaces of such die 12 therefore exhibit minimal or negligible positional deviation out of said common plane, along a direction parallel to a normal axis of the highly planar wafer table surface (e.g., a wafer table vertical axis $Z_{WT}$ corresponding to, overlapping with, or subsuming the base tray's vertical axis $Z_T$). The ultra-high planarity of the wafer table surface provided by multiple embodiments in accordance with present disclosure enables the die 12 on wafers 10 or film frames 12 residing on the wafer surface to sit substantially in/on one single plane (e.g., an inspection plane) to facilitate accurate inspection and/or other processing.

FIG. 5D is a cross sectional view of a wafer table structure 5 produced or manufactured in accordance with an embodiment of the present disclosure, which corresponds to FIG. 5C, and which and which carries a wafer or film frame upon a planar wafer table surface. The wafer table structure 5 provides a wafer table planar surface 190 having a very high or ultra-high degree of planar uniformity, such that die 12 (e.g., very small and/or very thin die 12), devices, or material layers carried by a wafer 10 or film frame 30 that is securely held or retained upon the wafer table planar surface by way of vacuum force(s) are collectively or commonly maintained, essentially maintained, or very substantially maintained in a wafer or film frame processing plane 192 (e.g., an optical inspection plane) with minimal or negligible positional deviation or displacement away from or out of the wafer or film frame processing plane 192 in a direction along a wafer table vertical axis $Z_{WT}$ (or equivalently, in a direction toward or away from the wafer table planar surface 190). In a representative embodiment, exposed or upper surfaces of die 12 having a planar surface area of between approximately 0.25-0.50 mm square or larger and a thickness of approximately 25-50 microns or greater can collectively exhibit a vertical deviation from the wafer or film frame processing plane 192 of less than approximately +/−100 µm, or less than approximately 10 to 90 µm (e.g., less than approximately +/−20 to 80 µm, or on average less than approximately 50 µm). Very small or ultra-small die 12 (e.g., approximately 0.25-0.55 mm square) and/or very thin or ultra-thin die 12 (e.g., approximately 25-75 µm or approximately 50 µm thick) can be maintained within an inspection plane 192 such that their deviation out of the inspection plane 192 is less than approximately 20-50 µm.

As previously indicated, the maximum transverse dimension or diameter of a given volume 140 of porous material within a particular base tray compartment 130, as well as the planar spatial extent or surface area spanned by a ridge 120 that defines or limits the maximum planar spatial extent or surface area of the compartment 130 in which the volume 140 of porous material resides, is correlated with or corresponds to a particular standard or expected wafer and/or film frame size, planar spatial extent or surface area, dimension, or diameter. More particularly, in order to securely hold or retain a wafer 10 or film frame 30 of a given size to the wafer table planar surface 190, vacuum force is provided or delivered to the wafer 10 or film frame 30 by way of selectively providing or delivering vacuum force to or through the vacuum opening(s) 20 disposed within or exposed to the compartment 130 having a maximum transverse dimension or diameter that most closely matches the transverse dimension or diameter of the wafer or film frame size currently under consideration, as well as each compartment 130 corresponding to a wafer or film frame size that is smaller than that of the wafer 10 or film frame 30 currently under consideration. Thus, a wafer 10 or film frame 30 of a particular size should entirely cover the upper surface of (a) a volume 140 of porous material having a transverse dimension or diameter that most closely matches the size of the wafer 10 or film frame 30 under consideration, as well as (b) each volume 140 of porous ceramic material having a smaller transverse dimension or diameter. A wafer 10 or film frame 30 should also cover a portion of the ridge 120 that most closely matches the size of the wafer 10 or film frame 30, as well as each ridge 120 having a diameter that is smaller than the wafer 10 or film frame 30 under consideration.

Figure 5E:
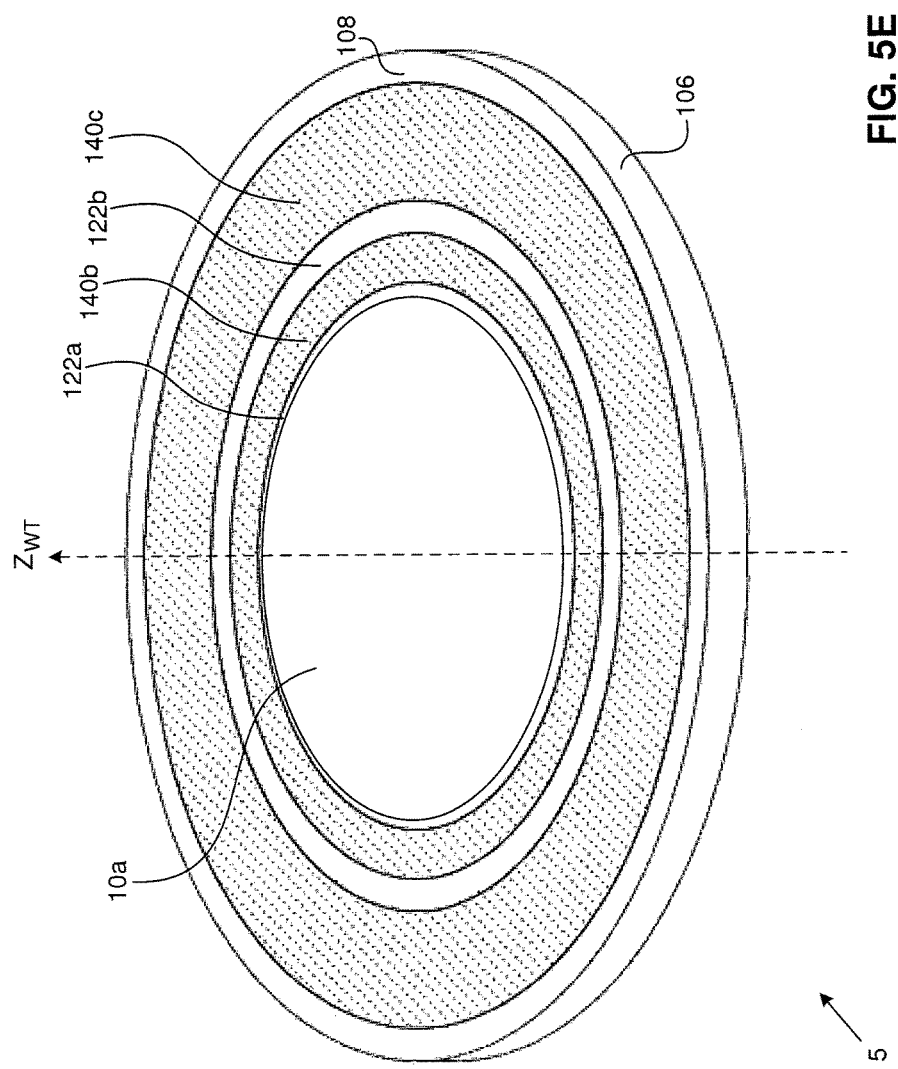
FIG. 5E is a perspective view of a representative first wafer having a first standard diameter (e.g., 8 inches) disposed upon a vacuum chuck structure in accordance with an embodiment of the present disclosure.

FIG. 5E is a perspective view of a representative first wafer 10*a* a having a first standard diameter (e.g., 8 inches) disposed upon a wafer table structure 5 in accordance with an embodiment of the present disclosure, such that the first wafer 10*a* can be securely retained upon the wafer table planar surface 190 by way of (a) the first wafer 10*a* covering the first volume 140*a* of porous material and covering at least a portion of the transverse width of the first ridge 120*a*, but not extending to or overlapping with the second volume 140*b* of porous material; and (b) the application or delivery of vacuum force to the first wafer 10*a* by way of selective or preferential provision of vacuum force to or through the first compartment's vacuum opening 20, into and through the first volume 140*a* of porous material, to an underside of the first wafer 10*a*.

Figure 5F:
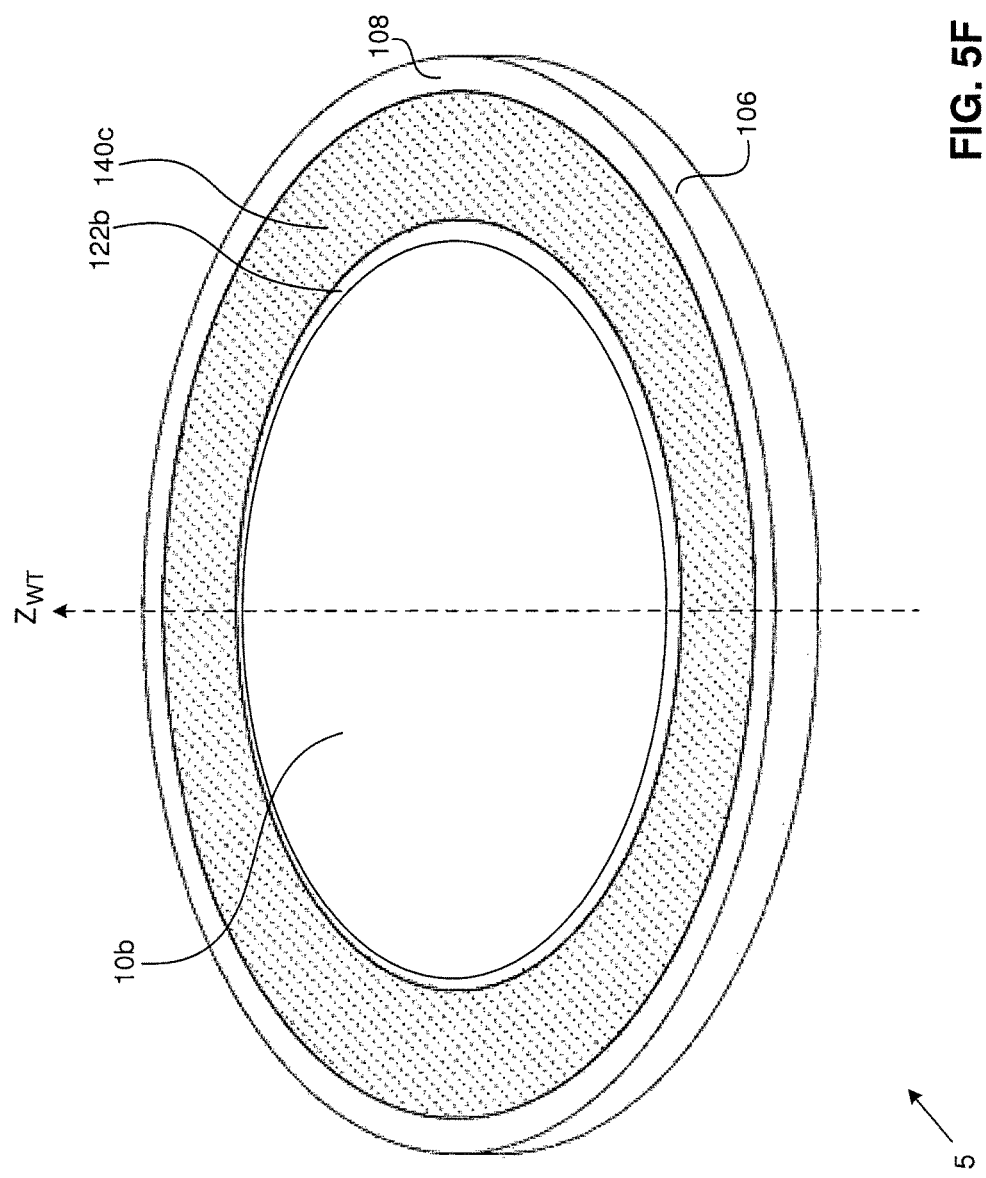
FIG. 5F is a perspective view of a representative second wafer having a second standard diameter (e.g., 12 inches) disposed upon a vacuum chuck structure in accordance with an embodiment of the present disclosure.

FIG. 5F is a perspective view of a representative second wafer 10*b* having a second standard diameter (e.g., 12 inches) disposed upon a wafer table structure 5 in accordance with an embodiment of the present disclosure. The second wafer 10*b* can be securely retained upon the wafer table planar surface 190 by way of (a) the second wafer 10*b* covering the first and second volumes 140*a-b* of porous material and covering at least a portion of the transverse width of the second ridge 120*b*, but not extending to or overlapping with the third volume 140*c* of porous material; and (b) the application or delivery of vacuum force to the second wafer 10*b* by way of selective or preferential provision of vacuum force to or through the first compartment's vacuum opening 20 and the second compartment's vacuum openings 20, into and through the first and second volumes 140*a-b* of porous material, to an underside of the second wafer 10*b*.

Figure 5G:
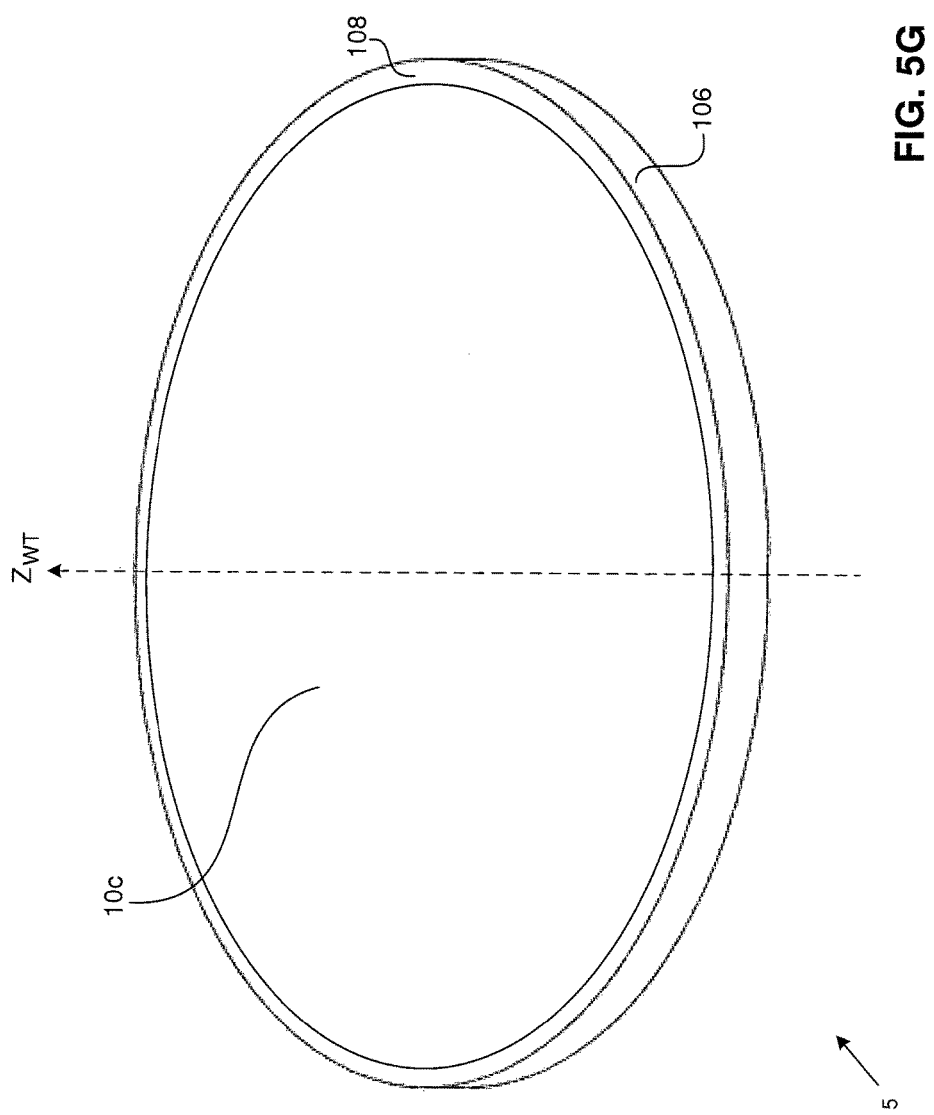
FIG. 5G is a perspective view of a representative third wafer having a third standard diameter (e.g., 16 inches)

FIG. 5G is a perspective view of a representative third wafer 10*c* having a third standard diameter (e.g., 16 inches) disposed upon a wafer table structure 5 in accordance with an embodiment of the present disclosure. The third wafer 10*c* can be securely retained upon the wafer table planar surface 190 by way of (a) the third wafer 10*c* covering the first, second, and third volumes 140*a-c* of porous material and covering a portion of the transverse width of the base tray's outer border 106; and (b) the application or delivery of vacuum force to the third wafer 10*c* by way of selective or preferential provision of vacuum force to or through the first compartment's vacuum opening 20, the second compartment's vacuum openings 20, and the third compartment's vacuum openings 20, into and through the first, second, and third volumes 140*a-c* of porous material, to an underside of the third wafer 10*c*.

In addition to the foregoing, in a number of embodiments a ceramic based base tray 100 can include or be formed to accommodate or provide one or more additional types of structural features or elements. Particular representative non-limiting embodiments of such ceramic based trays 102 are described in detail hereafter.

FIG. 6A is a perspective view of a ceramic based wafer table base tray 100 in accordance with another embodiment of the present disclosure, which includes a set of ejector pin guide members 160. FIG. 6B is a cross-sectional view of the ceramic based wafer table base tray of FIG. 6A, taken thorough a line C-C'. In such an embodiment, the base tray 100 can have a general or overall structure that is analogous or substantially identical to that described above. However, the first ridge 110*a* includes a number of ejector pin guide structures, elements, or members 160*a-c* (e.g., three in various embodiments, which is sufficient for enabling three ejector pins to handle each of 8 inch, 12 inch, and 16 inch wafers corresponding to such wafer sizes). Each ejector pin guide member 106*a-c* is shaped and configured for providing an opening 162 corresponding to or defining a passage or pathway through which an ejector pin can travel. In multiple embodiments, any given ejector pin guide member 160*a-c* can be formed as an integral portion or extension of the first ridge 110*a*, such that the ejector pin guide member 160*a-c* protrudes into a portion of the first compartment 120a. Moreover, ejector pin guide members 160a-c are dimensioned and/or constructed in such a manner such that essentially no, negligible, or minimal vacuum loss occurs through the ejector pin guide members 160a-c during wafer table structure use (e.g., during ejector pin elevation and lowering). In several embodiments, ejector pin guide members 160a-c can be strategically disposed such that a single set of ejector pins 164 can handle each wafer and film frame size that the wafer table structure 5 is designed to handle. One of ordinary skill in the relevant art will understand that ejector pin guide members 160a-c could alternatively or additionally be formed separate from the first ridge 110a, or as a portion of another ridge 110 (e.g., the second ridge 110b).

FIG. 7A is a perspective view of the base tray 100 of FIGS. 6A and 6B into which a moldable, formable, conformable, or flowable porous material has been introduced, provided, or disposed. FIG. 7B is a perspective cross sectional view of the base tray 100 carrying the moldable porous material corresponding to FIG. 7A, taken through a line D-D'. It should be noted that when the moldable porous material is introduced into the base tray 100, the opening 162 within and through each ejector pin guide member 160a-c should be sealed or blocked, such that porous material is excluded from the opening 162 and the passage through the ejector pin guide member 160a-c corresponding thereto in order to ensure that travel of an ejector pin 164a-c through the passage and the opening 162 is not impeded by hardened moldable porous material during ejector pin actuation involving the lowering or raising of wafers or film frames relative to the wafer table planar surface 190.

In some embodiments, the base tray 100 can carry, include, or incorporate a number of heating and/or cooling elements. For instance, heating elements can include resistive heating elements. Cooling elements can include tubes, channels, or passages which are configured for carrying a cooling substance or fluid (e.g., a chilled gas, or a liquid); or a thermoelectric cooling device. Heating and/or cooling elements can be enclosed or encapsulated within the non-porous ceramic based base tray material (e.g., integrally formed within one or more portions of the base tray 100). Alternatively, heating and/or cooling elements can reside external to the non-porous ceramic based base tray material, enclosed or encapsulated within portions of the porous material that occupies the base tray receptacles 130. In addition or as an alternative to the foregoing, the non-porous ceramic based base tray 100 and/or the porous material that occupies the base tray receptacles 130 can carry, include, or incorporate additional or other types of elements, such as electrodes, temperature sensing elements (e.g., thermocouples), other types of sensing elements (e.g., accelerometers, vibration sensors, or optical sensors), and/or other types of sensing elements configured for sensing surrounding/environmental conditions within and/or external to portions of the wafer table structure 5.

FIG. 8 is a flow diagram of a representative process 170 for manufacturing a wafer table structure 5 in accordance with an embodiment of the present disclosure. In an embodiment, a wafer table manufacturing process 170 includes a first process portion 172 involving providing a non-porous ceramic based wafer table base tray 100 having a plurality of compartments 130 therein; a second process portion 174 involving providing a moldable porous material; and a third process portion 176 comprising introducing the moldable porous material into the plurality of compartments 130 and filling the volumetric geometry of each compartment 130 within the plurality of compartments 130 with the moldable porous material, such that the moldable porous material conforms to or occupies the inner spatial dimensions of each compartment 130. Within each compartment 130, an initial volume 142 of moldable porous ceramic material can exceed or slightly exceed the volumetric capacity of the compartment 130 by way of the moldable porous ceramic material exhibiting a depth or thickness that exceeds the depth $D_{TC}$ of a base tray compartment 130, for instance, in a manner indicated or generally indicated in FIG. 9.

A fourth process portion 178 involves hardening or curing the moldable porous ceramic material and bonding the porous material to the inner surfaces (i.e., inner bottom surfaces 110 within the base tray 100 and compartment sidewalls corresponding to ridges 120) defining each compartment 130. Once the porous material is securely retained within or bonded to compartment inner surfaces, a fifth process portion 180 involves machining or polishing the porous material (i.e., each porous material volume 140) as well as portions of the base tray 110 such as exposed upper surfaces 122 of base tray ridges 120 and an exposed upper surface 108 of the base tray outer border 106 in order to simultaneously provide exposed, upper, or outer surfaces of porous material volumes 140, exposed upper surfaces 122 of base tray ridges 120, and the exposed upper surface 108 of the base tray outer border 106 with a very high degree of planarity, thereby defining a highly uniform wafer table planar surface 190 upon which wafers and film frames can be securely retained. Once planarized, each porous material volume 140 corresponding to any given compartment 130 is identical or essentially identical to the volume of the compartment 130.

A sixth process portion 182 involves coupling or mounting the planarized wafer table structure 5 to a displaceable wafer table or stage assembly (e.g., an x-y wafer stage), and coupling vacuum openings 20 within the planarized wafer table structure 5 to a set of stage assembly vacuum lines, links, and/or valves, such that vacuum force can be selectively actuated and applied to wafers 10 or film frames 30 disposed upon the wafer table planar surface 190.

In contrast to certain prior wafer table designs in which regions of porous material are separated by partitions made or substantially made of one or more metals, and/or which utilize an outer receptacle structure made or substantially made of one or more metals, various embodiments of wafer table structures in accordance with the present disclosure avoid or exclude ridges 120 made or substantially made of one or more metals, and typically further avoid or exclude a base tray 100 that is made or substantially made of one or more metals. More particularly, in prior wafer table designs that include upper or exposed non-porous wafer table surfaces that are at least partially or substantially made of metal, as well as upper or exposed porous wafer table surfaces that are at least substantially made of a ceramic material, such metal surfaces have quite different machining, grinding, or polishing characteristics, properties, or behavior than the porous ceramic material surfaces. During a machining, grinding, or polishing process, the metal surfaces will not planarize at the same rate or as readily as the porous ceramic material surfaces. Moreover, the metal surfaces can readily damage standard machining, grinding, or polishing elements, devices, or tools (e.g., polishing heads). The inclusion of metal surfaces makes the machining, grinding, or polishing process significantly more difficult, expensive, and time consuming compared to wafer table structures manufactured in accordance with embodiments of the present disclosure.

Furthermore, the difference between the machining, grinding, or polishing characteristics of the exposed metal surfaces and the exposed porous ceramic surfaces significantly increases the likelihood that the final as-manufactured wafer table surface will exhibit undesirable or unacceptable non-planarity, or insufficient planarity, across one or more sections or regions of the wafer table surface. Such prior wafer table designs are therefore not well suited for the inspection of large diameter, thin wafers 10 having fragile die 12 thereon, such as 12-inch or larger sawn wafers 10 carried by film frames 30 which carry small or ultra-small die 12. In contrast, wafer table structure embodiments in accordance with the present disclosure do not suffer from this drawback, and provide a highly uniform or ultra-uniform planar wafer table surface 622 that is very well suited to the inspection of such types of wafers 10 or film frames 30.

The end result of a wafer table structure manufactured in accordance with embodiments of the present disclosure is a wafer table 620 that (a) excludes or omits grooves or vacuum holes (e.g., drilled vacuum holes) on the wafer table surface 622 that can adversely affect the planarity of the wafer table surface 622 and result in one or more of the associated problems previously described; (b) has a very high or ultra-high planarity wafer table surface 622 suitable for handling (i) both wafers 10 and film frames 30, thereby eliminating the need for wafer table conversion kits, and (ii) very small or ultra-small die 12 (e.g., 0.5 mm×0.5 mm square, or smaller) residing on very thin or flexible wafers (e.g., 75 µm, 50 µm, or thinner), as the planar wafer table surface 622 facilitates the positioning and maintenance of such die 12 in/on a single plane, which may be difficult to achieve using conventional wafer table designs; and (c) structurally straightforward, low cost, and easy to manufacture, particularly compared to conventional wafer table designs which include grooves or machined/drilled vacuum holes on their wafer table surface, and/or exposed metal materials on their wafer table surface (e.g., metal plates, or a number of metal partitions across the wafer table surface).

Aspects of a Representative Wafer Alignment Station

Returning again to the description of other portions of the system 200 shown in FIG. 3A, the wafer (pre)alignment station 400 can include essentially any type of alignment apparatus or device configured to establish an initial wafer orientation or alignment relative to portions or elements of the wafer alignment station 400 and/or the inspection system 600 based upon the position(s) or orientation(s) of one or more wafer alignment features or structures in relation to the wafer alignment station 400 or the inspection system 600. Such wafer alignment features can include a major flat and possibly a minor flat, in a manner understood by one of ordinary skill in the relevant art. In a number of embodiments, the wafer alignment station 400 is conventional.

Aspects of a Representative Misalignment Inspection System

As previously described, the rotational misalignment of a wafer 10 with respect to a film frame 30 can result in decreased inspection throughput as more image capture events or frames would be required before an entire-die image of a rotationally misaligned die 12 can be captured and processed. In the description hereafter, particular embodiments of an apparatus and process for detecting wafer-to-film frame rotational misalignment are described with reference to FIG. 3A and FIGS. 10A-10C.

The misalignment inspection system 500 includes an apparatus or a set of devices configured for determining, detecting, or estimating a wafer rotational misorientation/misalignment direction and a corresponding wafer rotational misorientation/misalignment angle, magnitude, or value for a wafer 10 mounted on a film frame 30. Depending upon embodiment details, the misalignment inspection system 500 can include a film frame support or positioning apparatus or device; one or more illumination or optical signal sources (e.g., a set of broadband and/or narrowband light sources, such as LEDs); and/or one or more illumination or optical signal detectors or image capture devices. The misalignment inspection system 500 can also include a processing unit (e.g., within portions of an embedded system that includes a microcontroller configured for executing program instructions, plus a memory in which such program instructions can be stored; and signal communication or input/output resources).

Various misalignment inspection system embodiments are provided in the description hereafter, in which the misalignment inspection system 500 in some embodiments is configured for determining misalignment angles/misalignment directions and angular magnitudes by way of optically detecting the orientation of one or more wafer structural and/or visual features such as wafer gridlines or a set of flats relative to one or more film frame structural and/or visual features, for instance, film frame registration features 34*a-b*, or spatial directions associated with such film frame features. In other embodiments, the misalignment inspection system 500 is additionally or alternatively configured for determining misalignment directions and misalignment angular magnitudes by way of capturing at least one image of a wafer 10 disposed upon a film frame 30, and performing image processing operations involving a comparison between the captured image(s) of the wafer 10 and a set of reference axes that correspond to the FOV 50 of an image capture device, such as an image capture device within the misalignment inspection system 500 and/or within the inspection system 600.

Furthermore, as described below, the determination of and compensation for a wafer-to-film frame misalignment angle in accordance with an embodiment of the present disclosure can avoid, omit, or exclude, or eliminate the mechanical registration of the film frame 30 relative to the image capture device. Alternatively, in certain embodiments, the determination of a wafer-to-film frame misalignment angle can involve the mechanical registration of a film frame 30 relative to an image capture device (e.g., as a prior operation, or as an initial operation) by way of mating engagement of film frame registration features 34*a-b* with one or more registration elements, in a manner understood by one of ordinary skill in the relevant art.

In various embodiments, the determination of a misalignment angular direction and a corresponding misalignment angular magnitude occurs by way of image processing operations; and compensation or correction for a rotational misalignment of a wafer relative to a film frame on which the wafer is mounted and/or an image capture device FOV occurs by way of rotating the film frame across the rotational misalignment angular magnitude, in a direction opposite to the misalignment angular direction. Embodiments in accordance with the present disclosure can thus omit or avoid mechanical registration of the film frame 30 relative to an image capture device (e.g., a first image capture device and/or a second image capture device) by way of mating engagement of film frame registration features 34*a-b* with a set of film frame registration elements or structures.

FIG. 10A is a schematic illustration of a misalignment inspection system 500 configured for determining an extent of rotational or angular wafer misorientation/misalignment relative to a film frame 30 in accordance with an embodiment of the present disclosure. In an embodiment, the misalignment inspection system 500 includes an image capture device 540 coupled to a misalignment processing unit 510. The misalignment processing unit 510 is configured for executing program instructions (e.g., software) for determining or estimating the direction and magnitude of angular misalignment of a wafer 10 relative to a film frame 30. The misalignment processing unit is further communication with the system controller 1000, which is configured for communication with the second handling subsystem 300 and the inspection system 600.

The misalignment inspection system embodiment shown in FIG. 10A is configured for determining wafer-to-film frame misalignment by way of comparing or referencing wafer structural features to film frame structural features. More particularly, individual die 12 on a wafer 10 are typically visually identifiable or separated by grid lines, such as horizontal grid lines 6 and vertical grid lines 8, as understood by one of ordinary skill in the relevant art. If the wafer's horizontal or vertical gridlines 6, 8 exhibit a predetermined or standard reference orientation with respect to a set of film frame reference feature(s) (e.g., the wafer's horizontal or vertical gridlines 6, 8 are substantially parallel or perpendicular to particular predetermined film frame reference feature(s)), then the wafer 10 is properly aligned relative to the film frame 30, and correspondingly the wafer's die 12 will be properly aligned relative to the inspection system's image capture device FOV (thereby maximizing inspection throughput). On the other hand, if the wafer's horizontal or vertical gridlines 6, 8 do not exhibit the predetermined or standard reference orientation with respect to the set of film frame reference feature(s) (e.g., the wafer's horizontal or vertical gridlines 6, 8 are not substantially parallel or perpendicular to the particular predetermined film frame reference feature(s)), the wafer 10 is rotationally misaligned relative to the film frame 30, and the wafer's die will be misaligned with respect to the inspection system image capture device FOV in the absence of correction or compensation for such rotational wafer-to-film frame misalignment, thereby reducing inspection throughput. In multiple embodiments, the angular direction and angular magnitude of the wafer's misorientation/misalignment relative to the film frame 30 can be ascertained by determining a wafer misalignment angle. $\theta_W$ which is correlated with or which indicates or defines an angular disposition, offset, or displacement (e.g., as a number of degrees or radians) of one or more wafer gridlines 6, 8 relative to at least one film frame flat 35a-d. The wafer misalignment angle $\theta_W$ can indicate or include an angular misalignment direction (e.g., +/− direction) and an angular misalignment magnitude (e.g., e.g., a number of degrees or radians).

When a film frame 30 is under consideration by the misalignment inspection system of FIG. 10A, the misalignment inspection system image capture device 540 captures one or more images of the wafer 10 disposed upon the film frame 30 and generates corresponding image data. The image(s) captured by the misalignment inspection system image capture device 540 include (a) one or more wafer regions along which wafer grid lines 6, 8 at least partially extend (e.g., which extend along or across a significant or substantial portion of the wafer's surface area); and (b) portions (e.g., significant or substantial portions) of one or more film frame flats 35a-d relative to which the angular orientations of the grid line(s) 6, 8 within the captured image(s) can be determined or estimated. Thus, the misalignment inspection system image capture device 540 is disposed relative to the film frame 30 such that portions of at least one wafer gridline 6, 8 (e.g., a significant portion of the length of one or more gridlines 6, 8) and at portions of least one reference film frame flat 35a-d (e.g., a significant portion of the length of one or more film frame flats 35a-b) lie within a misalignment field of view $FOV_M$ 550 of said image capture device 540.

The aforementioned image data is communicated to the misalignment processing unit 510, which can perform image processing operations (e.g., conventional image processing operations performed by way of program instruction execution, in a manner understood by one of ordinary skill in the relevant art) to analyze the image data and determine or estimate the wafer misalignment angle $\theta_W$, which indicates the direction and magnitude of the angular misalignment of the wafer 10 relative to its film frame 30 (in a manner correlated with the angular orientation of the captured wafer gridline(s) 6, 8 relative to the captured film frame flat(s) 35a-d). One of ordinary skill in the art will understand that the capture of at least a significant length or spatial extent of one or more wafer gridlines 6, 8 (e.g., at least 3-5 cm) and at least a significant length or spatial extent of a one or more frame flats 35a-b (e.g., at least 2-4 cm), rather than a small segment or section of such wafer gridlines 6, 8 and film frame flats 35a-b, respectively, facilitates enhanced accuracy determination of the wafer misalignment angle $\theta_W$.

FIG. 10B is a schematic illustration showing representative aspects of determining a wafer misalignment angle $\theta_W$ by a misalignment inspection system 500 such as that shown in FIG. 10A. In the representative embodiment shown in FIGS. 10A and 10B, the misalignment system image capture device 540 is configured such that it can capture within its misalignment field of view $FOV_M$ 550 at least approximately 20%-50% (e.g., at, least approximately 25%-33%), of the surface region of the wafer 10 that is closest to the first film frame flat 35a (e.g., corresponding to a wafer region in which a wafer flat or notch 11 is expected to be disposed), and the majority of the length of the first film frame flat 35a proximate to this region of the wafer 10, for the largest film frame 30 that the system 200 is configured to handle (e.g., film frames 30 carrying 16-inch wafers 10). For smaller film frames 30 (e.g., film frames 30 carrying 12-inch or 8-inch wafers), such a misalignment system image capture device 540 can capture larger portions of such Smaller film frame's exposed surface areas.

In various embodiments, a single misalignment system image capture device 540 can be configured to capture images of each size of film frame 30 that the system 200 is configured to handle. Other embodiments can include multiple misalignment system image capture devices 540, for instance, a first image capture device 540 configured for capturing a first image corresponding to a first surface region (e.g., a lower surface region) of a wafer 10 and a corresponding first film frame flat 35a, and a second image capture device 540 configured for capturing a second image corresponding to another surface region of the wafer 10 (e.g., an upper surface region) and a corresponding other film frame flat 35c. The capture of the first and second images can occur simultaneously, substantially simultaneously, or sequentially. The first and second image capture devices can have identical or different misalignment fields of view $FOV_M$ 550, depending upon embodiment details.

In an embodiment, the misalignment processing unit 510 can determine or identify a reference wafer gridline, such as a vertical wafer gridline 6 that terminates closest to or at the wafer notch 11 or a midpoint of a wafer flat, and can generate a corresponding reference extended virtual or mathematical gridline 568 along which the vertical wafer gridline 6 is a line segment, and which extends to or past the film frame's first flat 35$a$. The misalignment processing unit 510 can additionally determine or estimate an angle between the first film frame flat 35$a$ and the reference extended gridline 568, which is correlated with the wafer misalignment angle $\theta_W$. For instance, as indicated in FIG. 10B, based upon or at an intersection point between the reference extended gridline 568 and a determined or calculated line or line segment along which the first film frame flat 35$a$ is a line segment, the misalignment processing unit 510 can determine an acute angle $\alpha_W$. One of ordinary skill in the relevant art will recognize that the wafer misalignment angle $\theta_W$ is given by $90°-\alpha_W$. Other embodiments can additionally or alternatively perform similar, analogous, or other types of calculations based upon standard geometrical and/or trigonometric relationships, in a manner understood by one of ordinary skill in the relevant art.

The misalignment processing unit 510 can communicate the wafer misalignment angle $\theta_W$ to the system control unit 1000 and/or the second handling subsystem 300 such that the wafer misalignment angle $\theta_W$ can be stored in a memory (e.g., buffered). The second handling subsystem 300 can receive, retrieve, or access the wafer misalignment angle $\theta_W$ corresponding to a film frame 300 being handled, and can rotate the entire film frame 300 opposite to the wafer misalignment angle $\theta_W$ to correct the wafer-to-film frame misalignment (e.g., under the control of program instruction execution).

FIG. 10C is a schematic illustration showing a misalignment inspection system 500 configured for determining an extent of rotational or angular wafer misorientation/misalignment relative to a film frame 30 in accordance with another embodiment of the present disclosure. In an embodiment, the misalignment inspection system 500 of FIG. 10C includes an image capture device 540 coupled to a misalignment processing unit 510, in a manner similar or analogous to that described above in relation to FIGS. 10A and 10B.

As understood by one of ordinary skill in the relevant art, within an inspection system 600, an image capture device (e.g., a camera) 640 provides a field of view FOV$_I$ 650 which corresponds to inspection system FOV axes X$_I$ and Y$_I$. Correspondingly, within the misalignment inspection system 500, an image capture device 540 provides a field of view FOV$_M$ 550 which corresponds to misalignment inspection system FOV axes X$_M$ and Y$_M$.

When a film frame 30 carrying a wafer 10 having zero misalignment (i.e., having a misalignment angle $\theta_W$ of zero degrees) with respect to the film frame 30 is registered relative to the misalignment inspection system's image capture device 540, the wafer's horizontal and vertical grid lines 6, 8 will have a predetermined orientation relative to the misalignment inspection system FOV axes X$_M$ and Y$_M$. For instance, under such conditions, the wafer's horizontal and vertical grid lines 6, 8 are aligned parallel to or geometrically coincident with, the misalignment inspection system FOV axes X$_M$ and Y$_M$. Similarly, when a film frame 30 carrying a wafer 10 having zero misalignment relative to the film frame 30 is registered with respect to the inspection system's image capture device 640, the wafer's horizontal and vertical grid lines 6, 8 will have a predetermined orientation relative to the inspection system FOV axes X$_I$ and Y$_I$ (e.g., the wafer's grid lines 6, 8 will be parallel to or geometrically coincident with the inspection system FOV axes X$_I$ and Y$_I$.

When a film frame 30 is under consideration for the determination of wafer misalignment relative to the film frame 30, the misalignment inspection system's image capture device 540 captures one or more images of the wafer 10 disposed upon the film frame 30 and generates image data corresponding thereto. Such image data is communicated to the misalignment processing unit 510, which can perform image processing operations (e.g., conventional image processing operations, in a manner understood by one of ordinary skill in the relevant art) to analyze the image data and determine the wafer misalignment angle $\theta_W$ based upon a misorientation or misalignment of one or more horizontal wafer grid lines 6 and/or one or more vertical wafer grid lines 8 with respect to the misalignment inspection system FOV axes X$_M$ and Y$_M$.

FIG. 10D is a schematic illustration showing aspects of determining an extent of rotational or angular wafer misalignment relative to a film frame 30 by a misalignment inspection system 500 such as that shown in FIG. 10C. As indicted in FIG. 10D, the extent to which a wafer's horizontal and vertical grid lines 6, 8 are rotationally or angularly offset from the misalignment inspection system FOV axes X$_M$ and Y$_M$ defines the wafer misalignment angle $\theta_W$. The misalignment processing unit 510 can communicate the wafer misalignment angle $\theta_W$ to the system control unit 1000 and/or the second handling subsystem 300, such that the wafer misalignment angle $\theta_W$ can be stored in a memory, and accessed by the second handling subsystem 300 to correct the rotational misalignment of the wafer 10 relative to its film frame 30.

As described in detail below, when the second handling subsystem 300 is handling a given film frame 30, the second handling subsystem 300 can access or retrieve (e.g., from a memory) a wafer misalignment angle $\theta_W$ corresponding to the film frame 30, and rotate the film frame 30 to correct for misalignment of the wafer 10 carried by the film frame 30, for instance, when the wafer misalignment magnitude exceeds a maximum misalignment angle threshold $\theta_{W\text{-}Max}$ (i.e., when $\theta_W > \theta_{W\text{-}Max}$), which can be predetermined, programmable, or selectable. The industry standard threshold is 15 degrees for wafer-to-film frame rotational misalignment. However, the experience of this patent applicant indicates that wafer-to-film frame rotational misalignment of more than 5 degrees should require adjustment because increasingly, die 12 are being manufactured smaller and wafer sizes are getting larger. Any delay in image capture of an entire-die or whole-die image for image processing as a result of wafer-to-film frame rotational misalignment, and hence inspection process throughput reduction, would be magnified or exacerbated given the large number of die carried by larger wafers (for instance, 10,000 or more die, such as 20,000-30,000, die), depending on die size and wafer size. For instance, $\theta_{W\text{-}Max}$ can be defined to have an angular magnitude of approximately 10 degrees, 7.5 degrees, 5 degrees, or 3 degrees. In general, the maximum misalignment angle threshold can depend upon die size and inspection system image capture device FOV 650 in relation in relation thereto.

As further described below, the second handling subsystem 300 can correct for wafer-to-film frame rotational misalignment without introducing any delay in film frame handling operations, that is, without causing a decrease in film frame handling or inspection process throughput. For instance, the second handling subsystem 300 can rotate a film frame 30 to correct for wafer-to-film frame rotational misalignment while transferring the film frame to the wafer table surface 622, in the same amount of time required to transfer a film frame 30 for which the wafer misalignment angle $\theta_W$ is zero or essentially zero. Consequently, in certain embodiments, essentially any wafer-to-film frame rotational misalignment that is detectable (e.g., reliably or repeatably detectable) by the misalignment inspection system 500 can be communicated to and/or acted upon the second handling subsystem 300, irrespective of a maximum misalignment angle threshold $\theta_{W\text{-}Max}$, such that the second handling subsystem 300 can automatically correct for wafer-to-film frame rotational misalignment on every or essentially every film frame 30 to be inspected, without affecting film frame handling throughput and inspection throughput.

In a number of embodiments, the misalignment inspection system 500 can be independent, separate, or distinct from one or both of the first and second handling subsystems 250, 300. For instance, the misalignment inspection system 500 can include or be an apparatus that is distinct from each of the first and second handling subsystems 250, 300, yet which is internal to the system 200, for instance, carried by the system's support structure 202. Alternatively, the misalignment inspection system 500 can be external to or remote from the system 200 (e.g. in a different room), for instance, disposed away from the system's support structure 202 and configured for operating at least substantially independently of the system 200 to determine for a number of film frames 30 disposed within a film frame carrier corresponding wafer angular misalignment directions and angular misalignment magnitudes, which can be stored in a memory and/or communicated to and/or retrieved by the system's control unit 1000 or the second handling subsystem 300 to facilitate wafer misalignment correction operations. In certain embodiments, the misalignment inspection system 500 can also include one or more film frame registration elements (e.g., mechanical registration elements configured for mating engagement with film frame registration features 34a-b), such that the misalignment inspection system 500 performs mechanical film frame registration prior to determining an extent of wafer-to-film frame misalignment.

In particular embodiments, portions of the misalignment inspection system 500 can include one or more portions of the second handling subsystem 300, the wafer table 620, and/or possibly portions of the inspection system 600 (e.g., a wafer table assembly 610 and one or more image capture devices). For instance, after a film frame 30 has been transferred to and placed upon the wafer table 620, an inspection system image capture device 640 can a set of capture images of the wafer 10 carried by the film frame 30 and generate one or more corresponding image data sets. A processing unit coupled to the inspection system 600 can analyze such image data sets to determine a wafer misalignment angle $\theta_W$, for the wafer 10 carried by the film frame 30 disposed on the wafer table 620. The processing unit can further compare the wafer misalignment angle $\theta_W$ to the maximum misalignment angle threshold $\theta_{W\text{-}Max}$ to determine if the magnitude of angular wafer misalignment exceeds the maximum misalignment angle threshold $\theta_{W\text{-}Max}$. If so, the processing unit can issue a misalignment correction request to the second handling subsystem 300, which can pick up the film frame 30 from the wafer table surface 622, and rotate the film frame 30 in a direction and by an angular amount that corrects or adjusts for the misalignment of the wafer 10 relative to its film frame 30. The second handling subsystem 300 can then place the film frame 30 back upon the wafer table surface 622, after which film frame inspection can begin under proper wafer to inspection system image capture device FOV 650 alignment conditions.

In other embodiments, portions of the misalignment inspection system 500 can include the first handling subsystem 200; plus an image capture device 540 that is disposed external to a film frame cassette, where the image capture device 540 is configured for capturing a set of images of a wafer 10 on a film frame 30 after the first handling subsystem 200 has withdrawn the film frame 30 from the film frame cassette. The first handling subsystem 200 can position the film frame 30 beneath the misalignment inspection system's image capture device 540, which can capture a set of images of the wafer 10 carried by the film frame 30 and communicate corresponding image data to the misalignment processing unit 510 for analysis/processing and the determination of a corresponding wafer misalignment angle $\theta_W$. In embodiments in which a portion of the first handling subsystem 200 such as an end effector 270 includes a mechanical film frame registration element 282, the film frame 30 can be mechanically registered with respect to the first handling subsystem 200 in association with withdrawal of the film frame 30 from the film frame cassette. The first handling subsystem 200 can position the film frame 30 relative to the misalignment inspection system's image capture device 540 in accordance with a known or predetermined positioning, such that the film frame 30 is mechanically registered with respect to the misalignment inspection system FOV axes $X_M$ and $Y_M$.

In still further embodiments, the second handling subsystem 300 can include, implement, or be combined or effectively combined with one or more portions of the misalignment inspection system 500. For instance, one or more portions of the second handling subsystem 300 can include or be positionable relative to a number of optical and/or image capture elements. In certain embodiments, after a film frame 30 has been transferred to the second handling subsystem 300, the second handling subsystem 300 can determine a wafer misalignment angle $\theta_W$ corresponding to a film frame 30. The second handling subsystem 300 can then rotate the film frame 30 to correct for the wafer-to-film frame rotational misalignment indicated by the wafer misalignment angle $\theta_W$, thereby establishing a proper orientation of the die 12 carried by the film frame 30 relative to the inspection system image capture device FOV 650. The second handling subsystem 300 can also transfer the film frame 30 to the wafer table 622 (e.g., simultaneous with film frame rotation, or subsequent to film frame rotation).

Aspects of Purely Mechanical Versus Image Processing Assisted Film Frame Registration One having ordinary skill in the relevant art will further recognize that if a wafer carried by a film frame is correctly mounted on the film frame with no or minimal rotational misalignment relative to the film frame, mechanical registration of the film frame by way of engaging film frame registration features 34a-b with film frame registration elements or structures results in the film frame being properly aligned relative to the FOV of an inspection system image capture device, which correspondingly results in the wafer being properly or acceptably aligned relative to the inspection system image capture device FOV.

However, when a wafer is originally mounted to a film frame, the wafer may be rotationally misaligned relative to the film frame. Consequently, when rotational misalignment of the wafer relative to the film frame exists, mechanical registration of a film frame fails to resolve the rotational misalignment of the wafer relative to the inspection system image capture device FOV. In other words, when such rotational misalignment exists, and has a magnitude beyond or outside of an acceptable range, mechanical registration of the film frame relative to an image capture device FOV is of no benefit with respect to ensuring that the wafer is properly aligned relative to the image capture device FOV.

Various embodiments in accordance with the present disclosure are configured for performing an optical or image processing assisted registration of a wafer carried by a film frame relative to an image capture device FOV, which involves image processing operations to determine a wafer rotational misalignment angle and a corresponding wafer rotational misalignment direction. Consequently, a mechanical film frame registration procedure can be omitted, avoided, or excluded. An individual of ordinary skill in the relevant art will recognize that the elimination of a manufacturing procedure, for instance, a film frame handling procedure such as a mechanical film frame registration procedure involving the mating engagement of film frame registration features 34a-b with one or more registration elements, saves time and therefore can increase throughput. Several embodiments in accordance with the present disclosure can render a mechanical film frame registration procedure unnecessary or redundant, as further described below. While a mechanical film frame registration procedure can still be performed in some of such embodiments, in multiple embodiments a mechanical film frame registration procedure can be avoided or eliminated.

Embodiments of the misalignment inspection system 500 such as that shown in FIGS. 10A-10B are configured for determining (by way of image capture and image processing operations) the wafer misalignment angle $\theta_W$ by way of determining or analyzing angular relationships between wafer structural or visual features and film frame structural or visual features. Such embodiments can accurately determine the wafer misalignment angle $\theta_W$, regardless or independent of whether the film frame 30 has been mechanically registered relative to the inspection system image capture device FOV 650. Provided that the second handling subsystem 300 has been registered or aligned relative to the inspection system image capture device 640 (e.g., as part of its installation, or an initial or one-time configuration/setup procedure), once the second handling subsystem 300 has rotated a film frame 30 to correct for the presence of a detected wafer-to-film frame rotational misalignment, the second handling subsystem 300 can directly transfer the film frame 30 to the wafer table surface 622 such that the die 12 carried by the film frame 30 are properly aligned and exhibit the correct rotational orientation (e.g., a maximum inspection process throughput orientation) relative to the inspection system image capture device FOV 650. The inspection system 600 can subsequently directly or immediately initiate film frame inspection operations without the need for a separate or an additional mechanical film frame registration procedure prior to inspection of the film frame 30.

Analogously, embodiments of the misalignment inspection system 500 such as that shown in FIGS. 10C-10D are configured for determining the wafer misalignment angle $\theta_W$ by way of determining or analyzing angular relationships between wafer structural or visual features and one or more misalignment inspection system FOV axes $X_M$ and $Y_M$. Such embodiments can also accurately determine the wafer misalignment angle $\theta_W$, regardless or independent of whether the film frame 30 has been mechanically registered relative to the inspection system image capture device FOV 650. Provided that the misalignment inspection system image capture device 540 has been registered or aligned relative to the inspection system image capture device 640 (e.g., as part of its installation, or an initial or one-time configuration/setup procedure), after the second handling subsystem 300 has rotated a film frame 30 to correct for wafer-to-film frame rotational misalignment, die 12 on the film frame 30 are properly aligned relative to the inspection system image capture device FOV 650. The second handling subsystem 300 can directly transfer the film frame 30 to the wafer table surface 622, and the inspection system 600 can directly or immediately initiate film frame inspection operations without the need for a separate or additional mechanical film frame registration procedure prior to initiating its inspection of the film frame 30.

By way of (a) the misalignment inspection system's accurate determination of a wafer misalignment angle $\theta_W$ regardless or independent of whether a film frame 30 has been mechanically registered relative to the inspection system image capture device FOV 650 and/or another portion of the system 200; (b) the second handling subsystem's rotation of the film frame 30 in accordance with $\theta_W$ (e.g., in a direction opposite to the direction indicated by $\theta_W$, and through an angular span equal or essentially equal to that indicated by $\theta_W$) to correct for wafer-to-film frame rotational misalignment, thereby providing a rotationally corrected film frame 30; and (c) the second handling subsystem's transfer of the rotationally corrected film frame 30 directly to the wafer table surface 622, embodiments in accordance with the present disclosure can effectively optically register film frames 30 relative to the inspection system image capture device FOV 650.

As long as the transfer of film frames 30 from the misalignment inspection system 500 to the second handling subsystem 300 accurately and reliably maintains or preserves each film frame's rotational orientation or disposition prior to the second handling subsystem's initiation of film frame rotation operations, such optical/image processing assisted registration of film frames 30 relative to the inspection system image capture device FOV 650 can eliminate the need for a mechanical film frame registration procedure. As further detailed below, the manner in which embodiments in accordance with the present disclosure transfer film frames 30 from the first handling subsystem 250 to the second handling subsystem 300 ensures or is intended to ensure that the rotational orientation of any given film frame 30 is accurately and reliably preserved between the time at which the misalignment inspection system 500 captures a set of images of a wafer 10 mounted on a film frame 30 and the time at which the second handling subsystem 300 initiates film frame rotation operations based upon the wafer misalignment angle $\theta_W$.

Furthermore, in multiple embodiments, a film frame handling and optical or optically assisted registration sequence involving each of (a) the misalignment inspection system's inspection of wafers 10 mounted on film frames 30 and determination of corresponding wafer misalignment angles $\theta_W$; (b) the transfer of film frames 30 from the misalignment inspection system 500 to the second handling subsystem 300; (c) the second handling subsystem's correction of wafer-to-film frame rotational misalignment, thereby effectuating an optically/image processing assisted registration of the film frame 30 relative to the inspection system image capture device FOV 650; and (d) the second handling subsystem's transfer of rotationally corrected film frames 30 to the wafer table surface 622 avoids introducing additional film frame handling time between the time at which a film frame 30 is retrieved from a film frame cassette to the time at which the film frame 30 is placed upon the wafer table surface 622. Thus, each of (a), (b), (c), and (d) within the aforementioned film frame handling and optically/image processing based registration sequence avoids decreasing film frame handling throughput and hence avoids decreasing inspection process throughput. Moreover, the omission or elimination of a conventional/purely mechanical film frame registration procedure, which requires a given mechanical registration time, results in time savings and a corresponding increase in throughput. In contrast to embodiments in accordance with the present disclosure, prior systems and methods have failed to recognize that the elimination of a mechanical film frame registration procedure is desirable or possible.

To further elaborate, as indicated above in some embodiments the misalignment inspection system 500 includes an image capture device 540 configured for capturing images of wafers 10 mounted on film frames 30 in association with the first handling subsystem's transfer of the film frames 30 from a film frame cassette to the second handling subsystem 300. For instance, the misalignment inspection system image capture device 540 can be disposed above portions of a film frame travel path along which a portion of the first handling subsystem (e.g., a robotic arm 260 coupled to an end effector 270, as described below) transports a film frame 30 to the second handling subsystem 300, such that the misalignment inspection system image capture device 540 captures images of the wafer 10 mounted on the film frame 30 as the film frame 30 moves along this travel path (e.g., "on-the-fly"). The misalignment inspection system 500 can then determine a wafer misalignment angle $\theta_W$ in a manner identical, essentially identical, analogous, or generally analogous to that described above, and communicate the wafer misalignment angle $\theta_W$ to the second handling subsystem 300. The first handling subsystem 250 can transfer the film frame 30 to the second handling subsystem 300 in a manner that accurately and reliably maintains the film frame's rotational orientation with respect to the misalignment inspection system's determination of the wafer misalignment angle $\theta_W$, after which the second handling subsystem can correct for wafer-to-film frame rotational misalignment and transfer the film frame 30 to the wafer table 622. In still another alternative embodiment, the first handling subsystem 250 can be configured for rotating the film frame 30 to compensate for a rotational misalignment of a wafer 10 mounted on a film frame 30, such as by way of a rotatable robotic arm assembly that carries the film frame 30 by way of an end effector.

Similar or analogous considerations to those described above with respect to the omission, elimination, or effective duplication of a mechanical film frame registration procedure apply to embodiments in which one or more portions of the misalignment inspection system 500 are combined with or implemented by the second handling subsystem 300, such that the second handling subsystem 300 can determine wafer misalignment angles $\theta_W$.

Aspects of a Representative First Handling Subsystem

The first handling subsystem 250 includes at least one end effector based handling apparatuses or device, such as one or more robotic arms 260 coupled to a set of corresponding end effectors 270. The first handling subsystem 250 is configured for performing particular types of wafer handling operations, and certain types of film frame handling operations. With respect to wafer handling operations, in several embodiments, the first handling subsystem 250 is configured for each of the following:
(a) retrieving wafers 10 from one or more wafer sources 210 prior to wafer processing by the inspection system 600, where a wafer source 210 can include or be a wafer carrier/cassette, or another processing system or station;
(b) transferring wafers 10 to the wafer alignment station 400;
(c) transferring initially aligned wafers 10 from the wafer alignment station 400 to the wafer table 620 (e.g., by transferring a wafer 10 to and positioning the wafer 10 upon the ejector pins 612, and subsequently releasing the wafer 10) to facilitate wafer processing operations;
(d) retrieving wafers 10 from the wafer table 620 (e.g., by capturing a wafer 10 elevated away from the wafer table 620 by way of the ejector pins 612, and removing the wafer 10 from the ejector pins 612); and
(e) transferring wafers 10 retrieved from the wafer table 620 to one or more post-processing wafer destinations 220, such as a wafer carrier or cassette or another processing system or station.

With respect to film frame handling operations, in several embodiments the first handling subsystem 250 is configured for each of the following:
(a) retrieving film frames 30 from one or more film frame sources 230 prior to film frame processing by the inspection system 600, where a film frame source 230 can include or be a film frame carrier/cassette, or another processing system or station;
(b) in some embodiments, establishing an initial film frame registration or alignment (which can be maintained relative to the wafer table 620 and/or one or more elements of the inspection system 600) by aligning, matching, engaging, or mating film frame registration features 34a-b with respect to at least one first handling subsystem registration element 282 that includes counterpart or complementary registration features 284a-b, for instance, with further reference to FIG. 11B, by way of a set of end effectors 270a-b that includes at least one end effector 270a that carries a first handling subsystem registration element 282;
(b) transferring film frames 30 to the second handling subsystem 300; and
(c) receiving film frames 30 from the second handling subsystem 300 and transferring received film frames 30 to one or more post-processing film frame destinations 240, which can include a film frame carrier or cassette or a film frame processing station.

In a number of embodiments, an initial film frame registration or alignment relative to the inspection system 600 is established in a conventional manner by way of registration elements carried by the wafer table assembly 610, and the mating engagement of film frame registration features 34a-b to such registration elements, in a manner readily understood by one of ordinary skill in the relevant art.

In an embodiment, the first handling subsystem 250 is also configured for (d) positioning film frames 30 with respect to the misalignment inspection system 500 to facilitate the determination or measurement of wafer angular misalignment magnitudes and directions relative to film frames 30 that carry the wafers 10.

Aspects of a Representative Second Handling Subsystem

In multiple embodiments, the second handling subsystem 300 is configured for the following wafer or film frame handling operations:
For film frame handling:
(a) exchanging film frames 30 with (i.e., receiving film frames 30 from, and transferring film frames 30 to) the first handling subsystem 300; and
(b) positioning film frames 30 upon the wafer table 620.
For wafer handling:
(c) selectively applying a flattening force or pressure to portions of wafers 10 that cannot be sufficiently, completely, or securely retained upon the wafer table surface 622 as a result of non-planarity or warpage, in association with wafer table application of a vacuum force to such non-planar or warped wafers 10 (and automatic/sensor-based determination of vacuum force sufficiency); and (d) spatially confining wafers 10 during wafer release from the wafer table 620, where such release can occur by way of vacuum force cessation and possible air purge application, and any ejector pin extension.

In certain embodiments, the second handling subsystem 300 is configured for establishing an initial film frame registration or alignment relative to one or more portions or elements of the inspection system 600 by aligning, matching, engaging, or mating frame registration features 34*a-b* with respect to at least one second handling subsystem registration element (not shown) that includes counterpart or complementary registration features (not shown), in a manner analogous or generally analogous to that indicated above for the first handling subsystem 250.

In an embodiment, the second handling subsystem 300 is additionally configured for rotating film frames 30 with respect to rotational misalignment information (e.g., the wafer misalignment angle $\theta_W$) corresponding to the wafer 10 mounted on the film frame 30 determined by the misalignment inspection system 500. Alternatively, wafer-to-film frame rotational misalignment can be inspected/determined by the inspection system 600 (e.g., misalignment inspection system 500 can be part of or implemented by the inspection 600 if the film frame 30 is positioned on the wafer table 622). As indicated above, the misalignment inspection system 500 can include the wafer table 620 and an image capture device 640 corresponding to the inspection system 600, and the second handling subsystem 300 can be configured for (a) positioning film frames 30 upon the wafer table 620 such that the misalignment inspection system 500 can determine a wafer-to-film frame angular misalignment direction and magnitude, and (b) retrieving film frames 30 from the wafer table 620, correcting wafer-to-film frame misalignment, and (c) subsequently placing such film frames 30 back on the wafer table 620.

In view of the foregoing, the first handling subsystem 250 can provide a wafer transport interface for transporting wafers 10 between a wafer table location corresponding to wafer table ejector pin positions and wafer sources/destinations other than or external to the wafer table 620. The second handling subsystem 300 can provide a film frame transport interface for transporting film frames 30 between the first wafer handling subsystem 200 and the wafer table 600; a film frame rotation interface; a wafer flattening interface; and a wafer lateral confinement interface.

As indicated above, with respect to a process for correcting wafer-to-film frame rotational misalignment, the second handling subsystem 300 need not perform the correction of such rotational misalignment while stationary. It can correct the rotational misalignment while transporting the film frame 30 enroute to the wafer table 620. This aspect of the design of second handling subsystem 300 ensures that no time is lost while performing wafer-to-film frame misalignment correction. Additionally, since it involves rotating the film frame 30 by a certain magnitude and direction to correct for wafer-to-film frame rotational misalignment without loss of time, it can be implemented for every inspection of a wafer 10 mounted on film frame 30.

Thus, the second handling subsystem 300 can (a) position film frames 30 upon the wafer table 620 in a manner that avoids or overcomes problems associated with rotational misalignment of wafers 10 relative to film frames 30, for instance, without loss of process time to correct rotational misalignment; (b) remove film frames 30 from the wafer table 620; (c) overcome insufficient or incomplete wafer surface area retention by the wafer table 620 due to loss of vacuum force caused by wafer non-planarity or warpage; and (d) prevent unwanted lateral displacement of wafers 10 along the wafer table surface 622 following vacuum force release or interruption, and the application of any associated air purge.

In a number of embodiments, the second handling subsystem 300 includes each of the following:

For film frame handling:
(a) a rotation compensation apparatus configured for automatically rotating a film frame 30 to correct for rotational misalignment of a wafer 10 relative to the film frame 30 (e.g., in accordance with an angular misalignment direction and magnitude, possibly in view of a maximum misalignment angle threshold or tolerance, which can be correlated with or correspond to a maximum allowable wafer-to-film frame misalignment tolerance); and
(b) a film frame placement and retrieval apparatus with respect to the wafer table ("film frame—wafer table placement/retrieval apparatus) configured for placing film frames 30 upon the wafer table surface 622 and removing film frames from the wafer table surface 622.

For wafer handling:
(a) a flattening apparatus configured for applying a force or pressure upon portions of a wafer 10 in a direction normal or substantially normal to the wafer table surface 622 (e.g., parallel to the wafer table z axis $Z_{wt}$) in association with the application of vacuum force by the wafer table 620; and
(b) a confinement or containment apparatus configured for at least substantially preventing lateral displacement of a wafer 10 along the wafer table surface 622 following cessation of a vacuum force applied to the wafer 10, and the application of any associated air burst or purge, to the underside of the wafer 10 by/through the wafer table 620.

In several embodiments, the second handling subsystem 300 includes a multifunction handling, transport, and/or pick and place apparatus that combines, integrates, or unifies portions of the rotation compensation apparatus, the flattening apparatus, and the confinement apparatus, as described in detail hereafter.

Aspects of a Representative Multifunction Pick and Place Apparatus

FIGS. 12A-12D are schematic illustrations showing aspects of a representative multifunction handling (MFH) apparatus, assembly, unit, or station 300 configured as each of a rotation compensation apparatus, a flattening apparatus, a confinement apparatus, and a film frame—wafer table placement/retrieval apparatus in a combined, integrated, or unified manner for performing wafer and film frame handling operations in accordance with an embodiment of the present disclosure. In an embodiment, the MFH apparatus 300 includes each of the following:

(a) a main body, frame element, or housing 302;
(b) a plurality of displaceable capture arms 310 coupled to the housing 302, configured for (i) selectively capturing, securely holding, and selectively releasing film frames 30 of different dimensions, sizes, or diameters by way of the application or cessation of vacuum forces provided to portions of a film frame's periphery or border, and (ii) selectively constraining or preventing lateral displacement of wafers 10 along the wafer table surface 622;

(c) a set of vacuum elements (e.g., vacuum linkages, lines, and/or valves) 318 coupled to the plurality of capture arms 310, which facilitate the control of vacuum forces or negative pressures applied by the plurality of capture arms 310 to film frames 30;

(d) a capture positioning assembly 320 that includes a capture arm displacement motor or driver 330 and a displacement linkage 334 coupled to the plurality of capture arms 310, for controllably displacing the plurality of capture arms 310 to multiple (e.g., selectable or predetermined) distinct positions or distances transverse to and away from or towards a common axis, such as a pick and place z axis $Z_{pp}$ corresponding or approximately corresponding to a midpoint, center, or centroid of a film frame 30 or a wafer 10 carried thereby, where each such distinct position or distance away from or toward $Z_{pp}$ can correspond to a different film frame dimension, size, or diameter;

(e) a rotational misalignment compensation motor or driver 340 configured for selectively and concurrently rotating each of the plurality of capture arms 310 (i.e., collectively rotating the plurality of capture arms 310) in a common direction about a common axis of rotation, such as the pick and place z axis $Z_{pp}$, to facilitate wafer angular misalignment correction operations;

(f) a support member or arm 352 configured for carrying the housing 302; and (g) a vertical displacement motor or driver 350 configured for selectively or controllably displacing the plurality of capture arms 310 along a vertical direction parallel to each of the wafer table z axis $Z_{wt}$ and the pick and place z axis $Z_{pp}$ (i.e., perpendicular or substantially perpendicular to the wafer table surface 622), for instance, by way of vertical displacement of the housing 302, to facilitate film frame—wafer table placement/retrieval.

In some embodiments, the MFH apparatus 300 can be disposed relative to, or configured for carrying, implementing, or optically communicating with a misalignment inspection system image capture device 540 which is configured for capturing images of a film frame 30 in a manner described or indicated above with reference to FIGS. 10A-10D. For instance, the MFH apparatus housing 302 can carry a set of optical and/or image capture elements, such an image capture device 540 that includes a set of image sensors, within or upon its housing 302. Alternatively, the housing 302 can be disposed below such an image capture device 540 (in which case one or more portions of the housing can include one or more openings to facilitate image capture therethrough). As a further alternative, the housing 302 can carry a set of optical elements such as a microlens array which is couplable to an optical fiber bundle, and which is configured for communicating optical or imaging signals corresponding to film frame images to an image capture device (e.g., a camera) that can be disposed external to or away from the housing 302. In such an embodiment, the set of optical elements can include a number of illumination sources (e.g., LEDs).

FIG. 12B is a schematic illustration showing portions of a capture arm 310 in accordance with an embodiment of the present disclosure. In an embodiment, each capture arm 310 includes an arm member 312 that extends in a direction or within a plane substantially transverse to the pick and place z axis $Z_{pp}$, and a corresponding terminal portion or end segment 314 that projects or extends away from the arm member 312 in a direction substantially parallel to $Z_{pp}$. Each arm member 312 and its corresponding end segment 314 includes a channel or passage therethrough configured for communicating, providing, or supplying a vacuum force. Furthermore, each end segment 314 carries, includes, or is coupled to a soft and resiliently deformable or pliable tip element 316 that facilitates secure vacuum retention of film frames (e.g., by way of end segment positioning at a peripheral portion or outer border of a film frame 30), minimal or negligible unwanted air intrusion or vacuum leakage, and reduced, minimal, or negligible likelihood of inducing damage or defects if positioned adjacent to or upon the surface of a wafer 10.

Aspects of Representative Film Frame Capture and Release

FIG. 12C is a schematic illustration showing portions of a capture positioning assembly 320 in accordance with an embodiment of the present disclosure, and a representative first positioning of the plurality of capture arms 310 at a first position or radial distance away from the pick and place z axis $Z_{pp}$, corresponding to a first film frame diameter or cross sectional area. FIG. 12C is a schematic illustration showing portions of the capture positioning assembly 320, and a representative second positioning of the plurality of capture arms 310 at a second position or radial distance away from $Z_{pp}$, corresponding to a second film frame diameter or cross sectional area, which is smaller than the first film frame diameter or cross sectional area.

The capture arm positioning motor 330 is configured for selectively orienting the plurality of capture arms 320 relative to each other and the pick and place z axis $Z_{pp}$, such that the plurality of capture arms 320 can be selectively disposed relative to or at multiple capture positions, where each capture position corresponds to a distinct film frame dimension, size, area, or diameter. In the embodiment shown in FIGS. 12B-12C, the selective positioning of the plurality of capture arms 310 occurs by way of pulleys 332a-e. More particularly, any given capture arm 310a-d is coupled to a corresponding pulley 332a-d in a manner that facilitates rotational of its arm member 312a-d about a central axis of the capture arm's corresponding pulley 332a-d; and the pulleys 332a-d corresponding to each capture arm 310a-d are mechanically coupled or linked to each other by way of the displacement linkage 334, which can be, for instance, a belt or band. An additional pulley 332e can be configured for regulating, providing, controlling, or selecting an amount of tension upon the displacement linkage 334. The capture arm positioning motor 330 is coupled to one of the pulleys 332d, which serves as a drive pulley 332d.

A rotational motion or force applied by the capture arm positioning motor 330 to the drive pulley 332d results in the simultaneous or essentially simultaneous and precise and controlled rotation of each pulley 332a-e by way of the displacement linkage 334, and hence simultaneous rotation of each arm member 312a-d about the central axis of its corresponding pulley 332a-d. Depending upon the direction in which the motor 330 rotates the drive pulley 332d, the rotation of arm member 312a-d results in radial displacement or translation of each capture arm's tip element 314a-d in a direction toward or away from the pick and place z axis $Z_{pp}$. Consequently, the tip elements 314a-d corresponding to the plurality of capture arms 310 are collectively displaced or translated transverse to, or in a common transverse plane relative to, the pick and place z axis $Z_{pp}$, in a manner that facilitates the automatic adjustment of a radial distance at which each tip element 314a-d is disposed from $Z_{pp}$. Particular distinct radial distances (e.g., selectable or predetermined distances) of the tip elements 314a-d away from $Z_{pp}$ correspond to and facilitate the capture of film frames 30 of different dimensions, sizes, or diameters (e.g., larger and smaller diameters). The ability of the tip elements 316 to move radially in equidistance towards or away from $Z_{pp}$ also facilitates the gentle pressing or holding down of a wafer 10 (e.g., a warped wafer 10) in association with a wafer handling process described in detail below.

Once the plurality of capture arms 310 is disposed at a radial distance away from $Z_{pp}$ that corresponds to the size of a film frame 30 under consideration, the plurality of capture arms 310 can be positioned such that the capture arm tip elements 316 are in contact with peripheral portions of the film frame 30. Vacuum can then be activated such that a vacuum force or negative pressure is applied to peripheral portions of the film frame 30 through the plurality of capture arms 310. The plurality of capture arms 310 can securely carry, hold, or retain the film frame 30 by way of the vacuum force applied therethrough. Analogously, the plurality of capture arms 310 can release the film frame 30 by way of cessation of the vacuum force applied therethrough.

In various embodiments, the MFH apparatus 300 is configured for positioning relative to portions of the first handling subsystem 250 (e.g., an end effector 270), such that the plurality of capture arms 310 can capture a film frame 30 from the first handling subsystem 250. For instance, when an end effector 270 has captured a film frame 30, the end effector delivers a vacuum force or negative pressure upon peripheral portions of the film frame's underside, in a manner understood by one of ordinary skill in the relevant art. When the first handling subsystem's end effector 270 carries a film frame 30, the plurality of capture arms 310 can be positioned above the end effector 270 and over the upper or top side or surface of the film frame 30. The plurality of capture arms 310 can then be vertically displaced relative to the end effector 270 (e.g., by the vertical displacement motor 350, and/or vertical displacement of a robotic arm 260 coupled to the end effector 270) such that the plurality of capture arm tip elements 316 contact peripheral portions of the film frame's top surface. During such vertical displacement of the plurality of capture arms 310, vacuum can be activated, such that a vacuum force or negative pressure flows through the plurality of capture arms. A set of vacuum sensors coupled to the second handling subsystem 300 can automatically monitor the vacuum pressure within vacuum lines coupled to the plurality of capture arms 310. Once the plurality of capture arms 310 comes into contact with peripheral portions of the film frame's upper side, the plurality of capture arms 310 can securely attach to or capture the film frame 30 bay way of the vacuum force delivered therethrough. After the vacuum sensor(s) detect that this vacuum force has exceeded a suitable capture threshold, the end effector 270 which has been holding portions of the film frame's underside can release the vacuum force it has been applying to the film frame's underside, thereby releasing the film frame form the end effector 270 and completing the transfer of the film frame 30 to the MFH apparatus 300.

In an analogous manner to that described above, the MFH apparatus 300 can be vertically displaced relative to the wafer table 620 in order to capture a film frame 30 carried by the wafer table 620 (e.g., a film frame which has been held upon the wafer table 620 by a vacuum force applied to the underside of the film frame 30). In such a situation, the wafer table 620 need not maintain its application of vacuum force to the film frame 30 throughout the transfer of the film frame 30 to the MFH apparatus 300 (e.g., since film frame 30 lateral displacement along the wafer table surface 622 may be unlikely even in the absence of wafer table vacuum force), although the wafer table 620 can maintain the application of such vacuum force to the underside of the film frame 30 in certain embodiments until, approximately until, or nearly until vacuum force capture of the film frame by the MFH apparatus 300 is complete.

In view of the foregoing, once the MFH apparatus 300 has transferred a film frame 30 captured or securely carried thereby to a given destination, such as over an end effector 270 or the vacuum table surface 622, the film frame 30 can be transferred or offloaded to the destination under consideration and released. When the offload destination is an end effector 270 or the wafer table 620, the MFH apparatus 300 will maintain its capture and secure retention of the film frame 30 until secure capture of the film frame 30 by the end effector 270 or wafer table 620, respectively has occurred (e.g., as determined by way of a vacuum sensor coupled to the end effector 270 or wafer table 620, respectively, in a manner readily understood by one of ordinary skill in the relevant art). The MFH apparatus 620 can then be displaced away from the offload destination (e.g., vertically displaced relative to the end effector 270 or the wafer table 620).

Aspects of Representative Wafer Rotational Misalignment Compensation

Once a film frame 30 has been captured by the plurality capture arms 310, the rotational misalignment compensation motor 340 can be selectively actuated to correct or compensate for rotational misorientation of a wafer 10 carried by the film frame 30. Such misalignment compensation occurs by way of the rotation of the entire film frame 30 relative to the pick and place z axis $Z_{pp}$ in accordance with a misalignment direction and misalignment magnitude or angle determined for the wafer 10.

FIG. 13A is a schematic illustration of a film frame 30 carried by a MFH apparatus 300 in accordance with an embodiment of the present disclosure. In the event that the wafer 10 supported by the film frame 30 is angularly misaligned relative to the film frame 30 by an extent or angle that exceeds a misalignment threshold magnitude value $\theta_{W\text{-}Max}$ (e.g., a maximum tolerable misalignment threshold, such as a programmable, selectable, predetermined number of degrees), the misalignment compensation motor 340 can cause the film frame 30 to rotate in a direction opposite to the direction of wafer misalignment, and across an angular span, arc length, or number of degrees that corresponds to, equals, or approximately equals the misalignment magnitude determined for the wafer 10. When the MFH apparatus 300 places such a rotated film frame 30 upon the inspection system's wafer table 620, the wafer 10 carried by the film frame 30 will have a correct or proper rotational alignment (i.e., a an angular misalignment of approximately zero degrees) with respect to the inspection system's image capture device(s) 640. This correction of the wafer's rotational misalignment can correspondingly ensure that die 12 are properly aligned relative to the image capture device's FOV 650.

In multiple embodiments, film frame rotation by the MFH apparatus 300 occurs by way of the simultaneous or collective rotation of each capture arm 310 within the plurality of capture arms 310 about the pick and place z axis $Z_{pp}$, such as by way of rotation of the housing 302 to which the capture arms 310 are coupled. In several embodiments, the misalignment compensation motor 340 provides, includes, or is coupled to a rotatable shaft 342 that is configured for rotating the housing 302; and a rotational motion encoder or rotary encoder configured for facilitating or effectuating control over the direction and extent of housing rotation, in a manner understood by one of ordinary skill in the relevant art.

FIG. 13B is a schematic illustration of the MFH apparatus 310 rotated about the pick and place z axis $Z_{pp}$ by a first misalignment compensation amount, magnitude, angle, or angular path length in a first misalignment compensation direction in accordance with an embodiment of the present disclosure, thereby compensating for or correcting a first angular misalignment of a first wafer 10a relative to a film frame 30. FIG. 13C is a schematic illustration of the MFH apparatus 310 rotated about $Z_{pp}$ by a second misalignment compensation amount, magnitude, angle, or angular path length in a second misalignment compensation direction, opposite to the first misalignment compensation direction, in accordance with an embodiment of the present disclosure, thereby compensating for or correcting a second angular misalignment of a second wafer 10b relative to a film frame 30.

When a film frame 30 carrying a misaligned wafer 10 is carried by the MFH apparatus 300, rotation of the housing 302 across or by an angle that equals or approximately equals the misaligned wafer's misalignment angle $\theta_W$, in a direction opposite to the angular direction of the wafer's misalignment, compensates for or corrects the wafer's misalignment, thereby establishing a correct or proper orientation of the wafer relative to one or more elements of the inspection system 600 (e.g., an image capture device, and a FOV provided thereby). The rotated film frame 30, and hence the correctly (re)oriented wafer 10 carried by the film frame 30, can subsequently be transferred to the inspection system 600. Furthermore, such rotation of a film frame 30 by the MFH apparatus 300 to compensate for wafer-to-film frame rotational misalignment can be performed while the MFH apparatus 300 is moving (e.g., "on the fly" film frame rotation during film frame transport), such as while the MFH apparatus 300 is transferring the film frame 300 to the wafer table 620. Hence, following or during rotation of the housing 302 by the first misalignment amount, magnitude, angle, or angular path length in the first misalignment compensation direction as indicated in FIG. 13A, the film frame 30 carrying the first wafer 10a can be transferred to a wafer table 620 such that inspection can begin under maximum throughput wafer die-to-FOV orientation conditions. Similarly, following or during rotation of the housing 302 by the second misalignment compensation amount, magnitude, angle, or angular path length in the second misalignment compensation direction as indicated in FIG. 13B, the film frame 30 carrying the second wafer 10b can be transferred to the wafer table 620 for inspection.

Because a film frame 30 that has been transferred to the wafer table 620 may have been rotated to compensate or correct for angular misalignment of the wafer 10 supported by the film frame 30, in several embodiments film frame registration operations occur away from the wafer table 620 or off of the wafer table surface 622 (otherwise, any film frame registration elements carried by the wafer table 620 would need to be rotated or repositioned in accordance with the angular extent to which the film frame 30 had been rotated). Thus, in accordance with multiple embodiments of the present disclosure, a wafer table assembly 610 or wafer table 620 need not include, and can omit or exclude, film frame registration elements or mechanisms, such as one or more film frame registration elements 282 of a type described above with reference to the first handling subsystem 250.

Furthermore, as indicated above, in some embodiments the MFH apparatus 300 can determine and correct for the wafer misalignment angle $\theta_W$ in the absence, omission, or exclusion of a film frame registration procedure (a) prior to film frame capture by the MFH apparatus 300, and (b) prior to the inspection system's initiation of film frame inspection operations upon a film frame 30 that the MFH apparatus 300 has directly transferred to the wafer table surface 622 following any such wafer-to-film frame rotational misalignment correction. As a result, such embodiments of the MFH apparatus 300 can facilitate or enable the elimination of such film frame registration procedures during film frame handling, thereby saving time and increasing throughput.

Aspects of Representative Film Frame Transfer

In various embodiments, the MFH apparatus 300 is configured to transfer film frames 30 to the wafer table 620, such as by way of placing or positioning film frames 30 directly upon the wafer table surface 622. In several embodiments, the vertical displacement motor 350 is configured for vertically displacing the housing 302 across a particular or predetermined distance in a direction parallel to each of the pick and place z axis $Z_{pp}$ and the wafer table z axis $Z_{wt}$, to thereby place or position the film frame 30 and its wafer 10 directly upon the wafer table surface 622. In such embodiments, placement of the film frame 30 upon the wafer table surface 622 and/or retrieval of the film frame 30 from the wafer table surface 622 need not involve, and can omit, avoid, or exclude the use of, wafer table ejector pins 612. After the housing 302 has been displaced by a distance at which the film frame 300 under consideration proximate, adjacent to, essentially upon, or upon the wafer table surface 622, a vacuum force can be applied by the wafer table assembly 620 to securely engage, capture, or retain the film frame 30 and its corresponding wafer 10 upon or against the wafer table surface 622, in a manner understood by one of ordinary skill in the relevant art. In association with the placement of the film frame 30 upon the wafer table surface 622 and the secure capture or retention of the film frame 30 thereupon, vacuum force(s) applied to the film frame 30 by the plurality of component capture arms 310 can be released, and the vertical displacement motor 350 can displace or raise the housing 302, and correspondingly displace or raise the plurality of capture arms 310 a given distance away from the wafer table surface 622.

Transfer of a film frame 30 held by the MFH apparatus 300 to the first handling subsystem 200 can occur in a manner that is analogous to that described above, for instance, by the first handling subsystem's positioning of an end effector 270 coupled to a robotic arm 260 under or below the plurality of capture arms 310. While embodiments described herein detail a MFH apparatus 300 configured for z-axis displacement, MFH apparatus embodiments in accordance with the present disclosure are not limited to only z-axis motion.

Aspects of Representative Wafer Warpage or Non-Planarity Remediation

If a wafer 10 is warped, a next intended process to be carried out on the wafer table 620 (e.g. inspection of wafer) cannot take place. Without manual intervention, the wafer inspection or manufacturing process will come to a halt, causing loss of throughput. Embodiments in accordance with the present disclosure provide an automatic corrective or remediative response when a wafer 10 is placed on a wafer table 620 is automatically detected to be warped, thus eliminating or essentially eliminating the need for manual intervention and correspondingly eliminating or effectively eliminating inspection system downtime or halt-time caused by warped wafers 10, thereby increasing inspection throughput (e.g., average inspection throughput that is determined/calculated based upon a number of expected warped wafers 10 within one or more inspection runs).

In association with and/or following the first handling subsystem's transfer of a wafer 10 to the wafer table surface 622, the activation or application of a vacuum force by the wafer table 620 (e.g., by way of activating one or more vacuum values) is intended or expected to facilitate secure engagement, capture, or retention the wafer 10 upon or against the wafer table surface 622 (e.g., by way of a vacuum force applied to the entire surface area of the underside of the wafer 10). However, when a wafer 10 includes one or more portions that are non-planar, substantially non-planar, or warped, secure retention of the wafer 10 to the wafer table surface 622 may not be possible (e.g., depending upon an extent of warpage). The lack of secure, suitable, sufficient, or appropriate engagement of a wafer 10 upon the wafer table surface 622 can be indicated by a determination of whether the magnitude of an applied vacuum force or negative pressure (e.g., as automatically provided or output by a vacuum gauge) is above or below an acceptable vacuum engagement pressure threshold value (e.g., which can be a programmable, selectable, or predetermined value).

In accordance with the present disclosure, multiple embodiments of the MFH apparatus 300 are configured for selectively applying or delivering one or more vacuum engagement assistance, planarizing, flattening, or tapping (e.g., gentle tapping) pressures or forces to portions of a wafer 10 supported by the wafer table surface 622, for which secure, adequate, or appropriate vacuum engagement to the wafer table surface 622 cannot be established as a result of wafer non-planarity or warpage. In several embodiments, in response to an indication or determination (e.g., an automatic determination, as performed in accordance with program instruction execution) that the activation of one or more vacuum elements (e.g., vacuum valves) has not resulted in secure or adequate vacuum engagement of a wafer 10 to the wafer table surface 622, the MFH apparatus 300 can dispose the plurality of capture arms 310 over portions of the wafer 10, such that at least a portion of each capture arm's tip element 316 is positioned directly over or is capable of engaging with or contacting a portion of an exposed, upper, or top surface of the wafer 10 under consideration.

FIGS. 14A-14B are schematic illustrations of MFH apparatus positioning of capture arm tip elements 316 over portions of a wafer 10 to facilitate secure capture of the wafer 10 upon a wafer table surface 622 in accordance with an embodiment of the present disclosure. For a wafer 10 under consideration, the positioning of capture arm tip elements 316 in such a manner can dispose each tip element 316 proximate or adjacent to and/or overlapping with a peripheral or outer boundary or border of the wafer 10. For instance, each capture arm 310 within the plurality of capture arms 310 can be positioned at a radial distance away from the pick and place z axis $Z_{pp}$ that is approximately equal to but slightly less than the spatial extent, span, or diameter of the wafer 10 under consideration. In a number of embodiments, the apparatus 300 can dispose the plurality of capture arms 310 such that (a) a circle which intersects a center or central point of each capture arm's end segment 314 is concentric or substantially concentric with a circular or substantially circular peripheral border of a wafer 10, and (b) each capture arm's tip element 316 can directly contact a peripheral portion of the exposed, upper, or top surface of the wafer 10.

The positioning of the plurality capture arms 310 over exposed portions of a wafer 10 can define an engagement assistance configuration for the capture arms 310 and/or their corresponding tip elements 316, in accordance with which the MFH apparatus 300 can apply an engagement assistance force or pressure (e.g., downward force or pressure) to particular areas or points of the wafer concurrent with the wafer table assembly's application of a vacuum force to the underside of the wafer 10, facilitating or enabling secure capture of the wafer 10 to the wafer table surface 622. One or more engagement assistance configurations defining spatial positions of capture arms 310 corresponding to particular or different wafer dimensions, sizes, areas, or diameters can be predetermined (e.g., in accordance with standard wafer sizes) and stored in and retrieved from a memory.

Following its positioning of the plurality of capture arm tip elements 316 over exposed, upper, or top portions (e.g., peripheral or outermost portions) of a wafer 10 (e.g., in accordance with a particular engagement assistance configuration), the MFH apparatus 300 can displace the capture arm tip elements 316 (e.g., by way of displacement of the housing 302) in a vertical direction parallel to the each of pick and place z axis $Z_{pp}$ and the wafer table z axis $Z_{wt}$, toward the surface 624 of the wafer table 620. The tip elements 316 can thereby establish contact with particular areas or points upon the wafer or film frame surface, and apply an engagement assistance, flattening, or planarizing force (e.g., a downward force or pressure) upon portions of the wafer 10. The wafer table assembly 620 applies a vacuum force to the underside of the wafer 10 concurrent with MFH apparatus application of the engagement assistance force to the wafer 10.

As a result of the simultaneous application of (a) the engagement assistance force to portions of the top surface of the wafer 10, and (b) the vacuum force to the underside of the wafer 10, a non-planar or warped wafer 10 can be automatically securely captured and subsequently retained upon the wafer table surface 622. Secure capture of the wafer 10 upon the wafer table surface 622 can be automatically indicated or determined by comparing a current vacuum pressure reading, measurement, or value to a vacuum engagement pressure threshold value, in a manner understood by one of ordinary skill in the relevant art. After secure capture of the wafer 10 upon the wafer table surface 622 has occurred, the MFH apparatus 300 can vertically displace the plurality of capture arms 310 away from the wafer 10, for instance, by raising or returning the housing 302 to a predetermined, default, or waiting/ready position.

The aforementioned wafer handling process is particularly well suited to or enabled by wafer tables 620 having a wafer table structure 5 in accordance with embodiments of the present disclosure, because the presence of ridges 120 in such wafer table structures 5 enables vacuum force to be confined and sealed beneath the portion of the wafer table surface area covered by the wafer 10. This effective vacuum seal prevents vacuum loss, and results in a strong vacuum force exerted upon or applied to the underside of the wafer 10, which in addition to the natural suction force helps to keep the wafer 10 in the position at which it was placed on the wafer table surface 622. Without the ridges 120, no effective vacuum force is likely to be activated because most of an applied vacuum force would be lost through wafer table surface areas not covered by the wafer 10.

In view of the foregoing, embodiments in accordance with the present disclosure can dramatically increase the likelihood that non-planar or warped wafers 10 can be automatically captured and securely retained upon a wafer table surface 622. Embodiments in accordance with the present disclosure therefore dramatically reduce or substantially eliminate the need for manual intervention associated with prior systems.

Aspects of Representative Lateral Wafer Displacement Control/Prevention

As further detailed below, when handling a very thin wafer 10 by way of a porous wafer table, a brief or very brief air spurt, burst, purge, or puff is applied to the wafer 10 to facilitate release of the wafer 10 from the wafer table surface. This can levitate the wafer 10 and cause undesirable, uncontrolled, or unpredictable lateral displacement of the wafer 10 across the wafer table surface 622. Such lateral displacement can easily shift the wafer 10 away (e.g., significantly away) from a predetermined wafer load/unload position at which an end effector 270 handling of the wafer is intended to occur. This can result in unreliable or unpredictable end effector 270 retrieval of the wafer 10, which can further prevent the end effector 270 from safely and reliably inserting the wafer 10 into a wafer cassette or positioning the wafer 10 at a subsequent processing station, quite possibly resulting in wafer damage or breakage.

In the past when wafers were thicker (e.g., on a normalized basis relative to their surface area), it was possible to use ejector pins to push up from below the wafer to lift the wafer up against the suction force, especially when there were also grooves on the wafer table. However, if grooves are absent, the natural suction force upon the wafer 10 can be very strong apart from the residual vacuum that may remain from the application of vacuum force through the wafer table 620. This means that it is harder for the vacuum beneath the wafer 10 to escape. Moreover, today, wafers 10 being processed are much thinner. Given these new constraints, it is not possible to simply use ejector pins to push against a thin wafer 10 held down by suction force. To do so would risk breaking the thin and fragile wafer 10.

Porous wafer tables had previously been used in backlapping systems/processes, but not in inspection systems/processes, until an inspection system such as that described in Singapore Patent Application No. 201103425-3, entitled "System and Method for Handling and Aligning Component Panes such as Film Frames and Wafers," filed on 12 May 2011, included a porous wafer table 620 that can be used to handle wafers 10. However, it was discovered that facilitating the release of very thin or ultra-thin wafers 10 from a very flat or ultra-flat porous wafer table surface 622 in a manner that reliably avoids damaging the thin and fragile wafer 10 during subsequent wafer handling can require human intervention.

The description herein provides a solution to this problem. To facilitate the release of very thin wafers 10 from a very flat or ultra-flat porous wafer table surface 622 in a manner that reliably avoids damaging the thin and fragile wafer 10, a momentary spurt, burst, purge, or puff of positive air pressure is applied through the porous compartment material in wafer table 620 to the underside of the wafer 10. The application of positive air pressure releases the natural suction force and reverses any residual vacuum force beneath the wafer 10. Once air is introduced beneath the surface of the wafer 10, the atmospheric pressure difference between the top and bottom surfaces of the wafer 10 will be equalized. However, this gives rise to yet another unique problem for wafer handling, which is the creation of an air cushion beneath the wafer 10 that causes the levitated wafer 10 to have unintended and unpredictable lateral movement relative to the wafer table surface 622, as the air cushion may not be evenly distributed beneath the wafer 10. The thinner the wafer 10 being handled, the more pronounced the effect that the air cushion has.

FIG. 15A is a schematic illustration of a representative wafer 10 that is held uniformly against a porous vacuum chuck surface 40 by way of the aforementioned natural suction force plus a vacuum force or negative pressure applied to the underside of the wafer 10. FIG. 15B is a schematic illustration of the wafer 10 of FIG. 15A following vacuum force cessation and the application of an air puff to the underside of the wafer 10, which results in the generation of an air cushion 42 beneath the wafer 10. The presence of an air cushion 42 beneath the wafer 10 can cause the wafer 10 to slide laterally and unpredictably along the wafer table surface 622, depending upon wafer weight distribution and/or differential support provided to the wafer 10 by the air cushion 42 underneath. FIG. 15C is a schematic illustration of the wafer 10 of FIG. 15B, indicating an unintended or unpredictable lateral displacement Δx of the wafer 10 along the wafer table surface 622 as a result of the air cushion 42.

FIGS. 15D-15E are schematic illustrations of MFH apparatus positioning of capture arms 310 and capture arm tips 316 relative to a wafer 10 in manner that limits or constrains wafer displacement along a wafer table surface 622 in accordance with an embodiment of the present disclosure. In several embodiments, following wafer inspection operations, the MFH apparatus 300 is configured for selectively disposing the plurality of capture arms 310 such that the capture arms 310 and/or capture arm tip elements 316 are positioned in accordance with a confinement configuration in which the tip elements 316 are disposed relative to each other in a manner that defines a planar spatial confinement area that is just marginally larger than the surface area of the wafer 10 on the wafer table surface 622 for the purpose of preventing any lateral movement. Vertical movement is not constrained.

When multiple capture arm tip elements 316 are (a) disposed in accordance with a confinement configuration corresponding to a wafer 10 having a given surface area A and a thickness t, and (b) touching the wafer table surface 622, or positioned at a distance away from the wafer table surface 622 that is significantly less than the wafer thickness t, each tip element 316 can be located just beyond the periphery of the wafer 10 and outside of the wafer surface area A. Such tip element positioning relative to the wafer 10 and the wafer table surface 622 can prevent or limit lateral displacement of the wafer 10 along the wafer table surface 622 beyond or outside of the spatial confinement area laterally. Multiple confinement configurations can be defined and stored in and retrieved from a memory. Each confinement configuration corresponds to a particular dimension, size, area, or diameter.

As a representative example, for a circular or generally/substantially circular wafer 10 having a given surface area $A_w$ and diameter $D_w$, a tip element confinement configuration can define or establish the positions of tip elements 316 relative to each other, the pick and place z axis $Z_{pp}$, and the wafer surface area $A_w$ or diameter $D_w$ such that a circle which (a) intersects a common point of each tip element 316 that is closest to $Z_{pp}$, and which (b) is concentric or substantially concentric to and slightly, very slightly, or marginally larger than the wafer 10 defines a spatial confinement area $A_c$ and a corresponding spatial confinement diameter $D_c$, where $A_c$ is slightly, very slightly, or marginally larger than $A_w$, and $D_c$ is slightly, very slightly, or marginally larger than $D_w$. Prior to the interruption or cessation of vacuum or suction force upon the wafer 10, the MFH apparatus 300 can position the tip elements 316 in accordance with this confinement configuration, such that each tip element 316 is (a) very slightly, slightly, or marginally beyond or outside of the wafer surface area $A_w$, and (b) is in contact with or very slightly or marginally displaced away from the wafer table surface 622. Following the interruption or cessation of a vacuum force applied to the underside of the wafer 10, the wafer 10 will be unable or highly unlikely to move beyond or outside of $A_c$, even during or after the application or delivery of an air purge to the underside of the wafer 10.

Following vacuum force cessation or interruption and the application of an associated air purge (e.g., nearly or essentially immediately after vacuum force cessation), the capture arm tip elements 316 briefly remain in the confinement configuration, positioned upon or adjacent/proximate to the wafer table surface 622 to ensure that lateral displacement of the wafer 10 is constrained or prevented. After a predetermined time delay (e.g., approximately 50 msec-250 msec or longer) and/or until the ejector pins 612 are activated to lift the wafer 10 away from the wafer table surface 622, the capture arm tip elements 316 can be elevated away from the wafer table surface 622, such as by vertical displacement of the housing 302 along the pick and place z axis $Z_{pp}$.

Once the ejector pins 612 have lifted the wafer 10 to a final vertical position relative to the wafer table surface 622, the first handling subsystem 250 can capture and transport or retrieve the wafer 10 to a wafer destination 240. More particularly, an end effector 260 that is positioned relative to the reference wafer load/unload position can reliably capture the wafer 10 supported by the ejector pins 612, reliably transport the wafer 10 to a next wafer destination 230, such as a wafer cassette, and reliably position the wafer 10 relative to the wafer destination 230 (e.g., within the wafer cassette) with minimal, negligible, or essentially no risk of wafer breakage due to wafer mispositioning relative to/upon the end effector 260.

This process is particularly well suited when the wafer handling system is processing a very thin wafer 10 to confine the wafer 10 to its original placement position, as very thin wafers tend to move unpredictably with application of positive air beneath them.

In an alternate embodiment, lateral wafer displacement control or prevention occurs by way of a precisely timed wafer release and vertical wafer displacement process or sequence involving (a) the wafer table assembly's cessation of vacuum force applied to the backside of the wafer 10; (b) the application of a brief air puff to the wafer's backside; and (c) the activation or extension of the set of ejector pins 612 to elevate or raise the wafer off of the wafer table surface 622 in a manner that is precisely timed relative to air puff application or initiation.

FIG. 16 is a flow diagram of a process 700 for limiting, controlling, or preventing unintended, unpredictable, or uncontrolled wafer displacement along a wafer table surface 622 in accordance with an embodiment of the present disclosure. In an embodiment, the wafer elevation process 700 includes a first process portion 702 involving the positioning of the wafer table 620 at a predetermined, reference, or default wafer load/unload position following completion of wafer inspection operations during which the wafer table assembly 610 applied a vacuum force to the backside of a wafer 10 to facilitate secure retention of the wafer 10 upon the wafer table surface 622.

The process 700 additionally includes a second process portion 704 involving the wafer table assembly's cessation of the application of vacuum force to the backside of the wafer 10, which is immediately, essentially immediately, or nearly immediately followed by a third process portion 706 involving the wafer table assembly's application of an air puff to the wafer's backside from an air puff onset time to an air puff cessation time, the difference between which can define an air puff duration. The air puff duration can be, for instance, approximately 500 msec or less (e.g., approximately less than or equal to 250 msec). As a result of the application of the air puff to the backside of the wafer 10, residual vacuum force beneath the wafer's backside which may be holding the wafer 10 against the wafer table surface 622 is released, and the natural suction force upon the wafer is also released.

The process 700 further includes a fourth process portion 708 involving waiting for a very brief ejector pin activation delay time following the time at which the air puff was initiated and prior to activating or displacing the ejector pins 612 in an upward or vertical direction parallel to the wafer table z axis $Z_{wt}$. The ejector pin activation delay time is typically very brief. For instance, the ejector pin activation delay time can be between approximately 5-50 msec (e.g., approximately 10-25 msec) after the air puff initiation or onset time or with a suitable time delay that can be determined experimentally. Immediately or essentially immediately after the ejector pin activation delay time has elapsed, a fifth process portion 710 involves the upward activation or elevation of the ejector pins 612 to elevate the wafer 10 away from the wafer table surface 600, and a sixth process portion 712 involves lifting the wafer off of the wafer table surface 622 with minimal or negligible lateral displacement as a result of the very brief ejector pin activation delay time relative to the air puff onset time (i.e., the time at which the air puff is initially applied to the wafer's backside). Finally, a seventh process portion 714 involves reliably retrieving the wafer 10 from the ejector pins 612 using the end effector 270.

As a result of the precise or highly controlled ejector pin activation timing relative to the air puff initiation time, the ejector pins 612 come into contact with the backside of the wafer 10 during an initial portion of the air puff duration, and lift or raise the wafer 10 away from the wafer table surface 622 essentially or substantially immediately after, or essentially or substantially synchronous with, the release of the wafer 10 from the wafer table surface 622 in response to the air puff. Because the ejector pins 316 are activated or elevated and engage with the backside of the wafer 10 following a very brief and well controlled, predictable, or precisely timed interval following the air puff onset time, it is expected that any lateral motion of the wafer 10 that occurs prior to the ejector pins 612 elevating the wafer 10 away from the wafer table surface 622 will be acceptably small, minimal, or negligible. In a manner analogous or identical to that described above, an end effector 260 which is positioned relative to the reference wafer load/unload position can reliably capture the wafer 10 supported by the ejector pins 612, reliably transport the wafer 10 to a next wafer destination 230, and reliably position the wafer 10 relative to the wafer destination 230 with minimal, negligible, or essentially no risk of wafer breakage due to wafer mispositioning relative to the end effector 260.

In certain embodiments, wafers 10 of different dimensions, sizes, areas, or diameters can exhibit different expected optimum ejector pin activation delay times. Such different expected optimum ejector pin activation times corresponding to different wafer sizes can be determined based upon experimentation or historical results, and stored in a memory or upon a computer readable medium for automatic retrieval by the control unit 1000 such that an appropriate ejector pin activation delay time is selected in accordance with the current size of wafers being inspected.

Aspects of a Representative Wafer Handling Process

FIG. 17 is a flow diagram of a representative wafer handling process 800 in accordance with an embodiment of the present disclosure. The wafer handling process 800 can be managed or controlled by a controller or control unit 1000 (e.g., a computer system, computing device, or embedded system) by way of the execution of program instructions (e.g., which are stored upon a computer readable medium such as a fixed or removable RAM or ROM, a hard disk drive, an optical disk drive, or the like). Such execution of stored program instructions can include the determination of whether a wafer 10 is securely retained upon a wafer table surface 622, and the retrieval from a memory or computer readable or data storage medium a vacuum force engagement threshold value and possibly confinement capture configuration parameters.

In an embodiment, the wafer handling process 800 includes a first process portion 802 involving retrieving a wafer 10 from a wafer cassette using an end effector 270; a second process portion 804 involving prealigning the wafer 10; and a third process portion 806 involving transferring the wafer 10 to the wafer table 620 when the wafer table 620 is positioned at a reference wafer load/unload position. A fourth process portion 808 involves applying a vacuum force to the backside of the wafer 10, and a fifth process portion 810 involves determining whether secure retention of the wafer 10 by the wafer table 620 has been established. Such a determination can include comparing a current vacuum or suction force reading or vacuum or suction force leakage reading to a threshold vacuum force engagement value, in a manner understood by one of ordinary skill in the relevant art.

If secure retention of the wafer 10 by the wafer table 620 has not been established within a given amount of time (e.g., approximately 0.5-2.0 seconds), a sixth process portion 812 involves positioning the MFH apparatus capture arm tip elements 316 over peripheral portions of the wafer 10 while the wafer 10 remains upon the wafer table surface 622, and a seventh process portion 814 involves applying a downward force upon such peripheral portions of the wafer 10 using the MFH apparatus 300 while the wafer table 620 continues to apply vacuum force to the backside of the wafer 10 to thereby establish secure capture or retention of the wafer 10 upon the wafer table 620. In certain embodiments, process portions 810, 812, and 814 can be repeated multiple times, possibly with distinct or different rotational orientations of the capture arm tip elements 316, in the event that a first attempt to establish secure retention of the wafer 10 upon the wafer table surface 622 was not successful. Establishment of secure retention of the wafer 10 upon the wafer table surface 622 in association with the sixth and seventh process portions 812, 814 can be determined by way of an automatic comparison of a current vacuum force reading or vacuum force leakage reading to a threshold vacuum force engagement value, as will be understood by one of ordinary skill in the relevant art.

Following the seventh process portion 814, or after the fifth process portion 810 in the event that secure vacuum engagement of the wafer 10 upon the wafer table surface 622 occurred without MFH apparatus assistance, an eighth process portion 816 involves inspecting the wafer 10. Once wafer inspection is complete, a ninth process portion 818 involves positioning the wafer table 620 at the wafer load/unload position.

A tenth process portion 820 involves determining whether unwanted lateral displacement of the wafer 10 is to be limited or prevented using the MFH apparatus 300. If so, an eleventh process portion 822 involves positioning MFH apparatus capture arm tip elements 316 in an appropriate wafer confinement configuration with respect to the wafer's diameter, and a twelfth process portion 824 involves disposing the tip elements 316 in this confinement configuration upon the wafer table surface 622 such that the wafer periphery is within the capture confinement area $A_C$ defined by the confinement configuration. A thirteenth process portion 626 involves terminating the wafer table's application of vacuum force to the backside of the wafer 10 and applying an air puff to the wafer's backside, and a fourteenth process portion 628 involves maintaining the capture arm tip elements 316 in the confinement configuration on the wafer table surface 622 until rising ejector pins 612 have engaged with the wafer 10 to elevate the wafer 10 away from the wafer table surface 622. While the capture arm tip elements 316 remain in the confinement configuration and are touching the wafer table surface 316, lateral displacement of the wafer 10 beyond the confinement area $A_C$ is prevented, thus ensuring that the wafer 10 remains at or approximately at a predetermined wafer retrieval position to facilitate subsequent reliable and damage-free wafer handling by an end effector 270.

Once the ejector pins 612 have begun to lift the wafer 10 away from the wafer table surface 622, a fifteenth process portion 830 involves moving the MFH apparatus 300 away from the wafer table 620 (e.g., by vertically displacing the MFH apparatus housing 302); and a final process portion 840 involves retrieving the wafer 10 from the ejector pins 612 using the end effector 270 and returning the wafer to the wafer cassette.

Aspects of a Representative Film Frame Handling Process

FIG. 18 is a flow diagram of a representative film frame handling process 900 in accordance with an embodiment of the present disclosure. In a manner analogous to that described above, a film frame handling process 900 can be managed or controlled by the control unit 1000 by way of the execution of program instructions (e.g., which are stored upon a computer readable medium such as a fixed or removable random access memory (RAM), a read-only memory (ROM), a hard disk drive, an optical disk drive, or the like). Such execution of stored program instructions can include the retrieval of maximum wafer-to-film frame misalignment threshold value from a memory; the determination of whether an extent or magnitude of wafer misalignment relative to a film frame is less than or greater than a maximum misalignment threshold value; and the retrieval from a memory a set of MFH apparatus capture arm positions corresponding to a film frame size under consideration In an embodiment, the film frame handling process 900 includes a first process portion 902 involving retrieving a film frame 30 from a film frame cassette using an end effector 270, which applies a vacuum force to peripheral portions of the film frame's underside, backside, or bottom surface. Some embodiments of film frame handling process 900 can include a second process portion 904 involving a mechanical film frame registration procedure in which film frame alignment features are matingly engaged with a set of film frame registration elements 282. For instance, a registration element 282 can be carried by the end effector 270, a portion of the MFH apparatus 300, a portion of a misalignment inspection system 500, or a portion of the wafer table 620.

As previously described, in multiple embodiments, such a mechanical film frame registration procedure can be avoided, omitted, excluded, or eliminated (in view of an optical or image processing based film frame registration procedure), thereby avoiding or eliminating a conventional film frame handling event or procedure, saving time, and increasing throughput. Consequently, depending upon embodiment details, the second process portion 904 can be omitted or eliminated, or the second process portion 904 can be optional in view of an optical film frame registration procedure performed by way of the misalignment inspection system 500 and the MFH 300.

A third process portion 906 involves determining a rotational or angular direction and magnitude of wafer misalignment relative to the film frame 30 using the misalignment inspection system 500. As indicated above, depending upon embodiment details, the determination of the angular wafer misalignment relative to the film frame 30 can occur (a) external to or remote from the system 200, before the film frame 30 has been retrieved by the end effector 270 in association with the first process portion 902; or (b) at any time following the retrieval of the film frame 30 by the end effector 270 but prior to the initiation of film frame inspection by the inspection system 600.

A fourth process portion 908 involves positioning the film frame 30 beneath the MFH apparatus 300, e.g., such that a common axis of MFH apparatus capture arm rotation, such as the pick and place z axis $Z_{pp}$, coincides with or extends through the center or approximate center of the film frame 30. A fifth process portion 910 involves positioning the MFH apparatus capture arm tip elements 316 upon peripheral portions of the film frame's upper or top surface, and applying vacuum force through the capture arms 310 such that the MFH apparatus 300 securely captures the film frame 30. A sixth process portion 912 involves terminating or releasing the end effector vacuum force applied to peripheral portions of the film frame's underside, and moving the end effector 270 away from the MFH apparatus 300.

A seventh process portion 914 involves rotating the film frame 30 using the MFH apparatus (e.g., by concurrently rotating the capture arms 310 about the aforementioned common axis of capture arm rotation) in the event that the wafer-to-film frame misalignment determined in association with the third process portion 906 exceeds the maximum misalignment threshold value, or in the event that a wafer-to-film frame misalignment was detected or determined. Such rotation occurs in a direction and through an angle that corrects the wafer-to-film frame misalignment, i.e., opposite to the wafer-to-film frame misalignment.

An eighth process portion 916 involves moving the wafer table 620 to a film frame load/unload position, which can occur concurrently with the seventy process portion 914, thereby saving time and increasing throughput. A ninth process portion 918 involves placing the film frame 30 on the wafer table 620 using the MFH apparatus 300, such as by way of vertical displacement of the MFH apparatus housing 302. The ninth process portion 918 can involve displacing the MFH apparatus housing 302 by a predetermined distance, and/or determination of whether the film frame 30 has been securely captured by the wafer table 620 in association with a tenth process portion 920 that involves applying a vacuum force to the underside of the film frame 30 using the wafer table 620. Once the film frame 30 has been securely captured by the wafer table 620, the tenth process portion 920 further involves terminating the application of the vacuum force applied through the capture arms 310 to the top surface of the film frame 30 and moving the MFH apparatus 300 away from the wafer table 620, thereby enabling subsequent film frame inspection. In particular embodiments, the ninth process portion 918 can additionally or alternatively involve displacing the housing 302 toward the wafer table surface 622 until the capture arm tip elements 316 touch the wafer table surface 622, which can be determined by way of a set of sensors (e.g., optical sensors).

An eleventh process portion 922 involves inspecting the film frame 30, and a twelfth process portion 924 involves positioning the wafer table 620 at the film frame load/unload position. A thirteenth process portion 926 involves positioning the MFH apparatus capture arm tip elements 316 on peripheral portions of the film frame's top side, and applying a vacuum force to the top side of the film frame 30 to capture the film frame 30 while the film frame 30 remains upon (e.g., is securely held to) the wafer table surface 622. A fourteenth process portion 928 involves discontinuing the wafer table's application of vacuum force to the film frame's underside, such that the MFH apparatus can capture and remove the film frame 30 from the wafer table 620.

A fifteenth process portion 930 involves moving the MFH apparatus 300, which securely holds the film frame 30, away from the wafer table surface 622, such as by way of vertically displacing the MFH apparatus housing 302. A sixteenth process portion 932 involves positioning the end effector 270 beneath the MFH apparatus 300, and a seventeenth process portion 934 involves capturing portions of the film frame's backside periphery using the end effector 270 by way of vacuum force applied through the end effector 270, such that the film frame 30 is securely retained by the end effector 270 (and simultaneously retained by the MFH apparatus 300). An eighteenth process portion 936 involves discontinuation of the vacuum force applied to peripheral portions of the film frame by the MFH apparatus 300, such that the film frame 30 is released from the MFH apparatus 300. Finally, a nineteenth process portion 938 involves lowering the end effector 270 relative to the MFH apparatus 300 and transferring the film frame 30 back to the film frame cassette using the end effector 270.

Aspects of various embodiments in accordance the present disclosure address at least one aspect, problem, limitation, and/or disadvantage associated with existing systems and methods for handling wafers and/or film frames. Aspects of multiple embodiments in accordance with the present disclosure address each of the problems, limitations, and/or disadvantages described above associated with existing systems and methods for handling wafers and/or film frames. Moreover, multiple embodiments in accordance with the present disclosure improve wafer and/or film frame handling in one or more manners that prior systems and methods do not or cannot, such as by way of the elimination of particular handling events or procedures which results in enhanced throughput. While features, aspects, and/or advantages associated with certain embodiments have been described in the disclosure, other embodiments may also exhibit such features, aspects, and/or advantages, and not all embodiments need necessarily exhibit such features, aspects, and/or advantages to fall within the scope of the disclosure. It will be appreciated by a person of ordinary skill in the art that several of the above-disclosed systems, components, processes, or alternatives thereof, may be desirably combined into other different systems, components, processes, and/or applications. In addition, various modifications, alterations, and/or improvements may be made to various embodiments that are disclosed by a person of ordinary skill in the art within the scope of the present disclosure.

The invention claimed is:

1. A system for handling wafers, each wafer having a periphery and a surface area, the system comprising:
a wafer table assembly comprising a wafer table providing a planar wafer table surface configured for carrying a wafer, the wafer table assembly configured for applying a negative pressure or a positive pressure to an underside of the wafer;
a flattening apparatus configured for automatically applying a downward force to portions of a warped or non-planar wafer in a direction normal to the wafer table surface,
wherein the flattening apparatus eliminates a need for manual intervention when the warped or non-planar wafer cannot be reliably retained on the wafer table surface as a result of its warpage or non-planarity; and
a displacement limitation apparatus configured for automatically constraining or preventing uncontrolled lateral displacement of the wafer relative to the wafer table surface after cessation of an applied negative pressure and/or an application of a positive pressure to the underside of the wafer via the wafer table, to thereby eliminate a need for manual intervention in response to such uncontrolled lateral displacement of the wafer.

2. The system of claim 1, wherein the wafer table surface comprises a porous material.

3. The system of claim 1, wherein the flattening apparatus comprises:
a main body positionable over the wafer table surface and displaceable along a vertical axis that is perpendicular to the wafer table surface;
a plurality of arms coupled to the main body, each arm within the plurality of arms having a tip element comprising a soft and resiliently deformable material coupled thereto, each arm controllably displaceable to multiple distinct positions transverse to and towards or away from the vertical axis;
a vertical displacement driver configured for (a) controllably displacing the main body and consequently simultaneously displacing the plurality of arms and the tip elements coupled thereto along a vertical direction parallel to the vertical axis to position the tip elements in accordance with an engagement assistance position corresponding to a dimension of the wafer upon the wafer table, such that a portion of each tip element is disposed directly over an exposed upper surface of the wafer for engaging with or contacting a portion of the exposed surface of the wafer, and (b) controllably displacing the tip elements positioned in accordance with the engagement assistance position in a downward direction toward the wafer table surface.

4. The system of claim 3, wherein the plurality of tip elements is displaceable to a plurality of engagement assistance positions, each engagement assistance position disposing the tip elements away from each other across an area that is slightly less than a standard wafer diameter at the periphery of the wafer on the wafer table surface,
wherein each engagement assistance position corresponds to a different standard wafer dimension.

5. The system of claim 1, wherein the displacement limitation apparatus comprises:
a main body positionable over the wafer table surface and displaceable along a vertical axis that is perpendicular to the wafer table surface;
a plurality of arms coupled to the main body, each arm within the plurality of arms having a tip element comprising a soft and resiliently deformable material coupled thereto, each arm controllably displaceable to multiple distinct positions transverse to and towards or away from the vertical axis; and
a vertical displacement driver configured for (a) controllably displacing the main body and consequently simultaneously displacing the plurality of arms and the tip elements coupled thereto along a vertical direction parallel to the vertical axis to position the tip elements in accordance with a confinement configuration corresponding to a dimension of the wafer upon the wafer table, such that each tip element is disposed slightly beyond the periphery of the wafer, and (b) controllably displacing the tip elements positioned in accordance with the confinement configuration in a downward direction toward the wafer table surface.

6. The system of claim 5, wherein the tip elements are displaceable to a plurality of confinement configurations, each confinement configuration disposing the tip elements away from each other across a planar spatial confinement area that is marginally larger than the surface area of the wafer on the wafer table surface, wherein each confinement configuration corresponds to a different standard wafer dimension.

7. The system of claim 1, wherein the wafer table assembly includes a set of ejector pins displaceable along a vertical direction perpendicular to the wafer table surface, and wherein the displacement limitation apparatus further comprises:
a control unit configured for controlling:
(a) an application of an air puff to the underside of the wafer essentially immediately after interruption or cessation of the applied negative pressure to the underside of the wafer, the air puff applied from an air puff onset time to an air puff cessation time; and
(b) activation of the set of ejector pins to displace the set of ejector pins in an upward direction after a very brief ejector pin activation delay time following the air puff onset time to thereby lift the wafer off of the wafer table surface with minimal or negligible lateral displacement as a result of the very brief ejector pin activation delay time relative to the air puff onset time,
wherein the ejector pin activation delay time is precisely controlled relative to the air puff onset time such that the wafer is vertically raised away from the wafer table surface synchronous with the release of the wafer from the wafer table surface in response to the air puff.

8. The system of claim 7, wherein the ejector pin activation delay time is experimentally determined.

9. The system of claim 7, wherein the ejector pin activation delay time is between 5-50 msec.

10. A method for handling wafers, each wafer having a periphery and a surface area, the method comprising:
transporting a wafer to a planar wafer table surface corresponding to a wafer table assembly comprising a wafer table configured for applying a negative pressure or a positive pressure to an underside of the wafer;
automatically remediating insufficient retention of the wafer upon the wafer table surface due to wafer warpage or non-planarity; and automatically preventing uncontrolled lateral displacement of the wafer relative to the wafer table surface following interruption or cessation of an applied negative pressure and/or an application of positive pressure to the underside of the wafer.

11. The method of claim 10, wherein automatically remediating insufficient retention of the wafer upon the wafer table surface comprises:
automatically detecting insufficient retention of the wafer upon the wafer table surface; and
responsively applying a set of downward forces to portions of an exposed upper surface of the wafer concurrent with the application of the negative pressure to the underside of the wafer to facilitate secure retention of the wafer upon the wafer table surface.

12. The method of claim 11, wherein applying the set of downward forces comprises:
positioning a flattening apparatus above the wafer, the flattening apparatus comprising a housing coupled to a plurality of displaceable arms, each arm within the plurality of arms coupled to a tip element comprising a soft and resiliently deformable material;
positioning the tip elements in accordance with an engagement assistance position corresponding to a dimension of the wafer upon the wafer table, such that a portion of each tip element is disposed directly over the exposed upper surface of the wafer for engaging with or contacting a portion of the exposed surface of the wafer; and
displacing the tip elements disposed over the exposed upper surface of the wafer downward toward the wafer table surface.

13. The method of claim 11, further comprising:
detecting secure retention of the wafer upon the wafer table surface by way of a vacuum gauge; and
terminating the application of the set of downward forces to portions of the exposed upper surface of the wafer in response to secure retention of the wafer on the wafer table surface.

14. The method of claim 10, wherein automatically preventing uncontrolled lateral displacement of the wafer relative to the wafer table surface comprises:
positioning a confinement apparatus above the wafer, the confinement apparatus comprising a housing coupled to a plurality of displaceable arms, each arm within the plurality of arms coupled to a tip element comprising a soft and resiliently deformable material;
positioning the tip elements in accordance with a confinement configuration corresponding to a dimension of the wafer upon the wafer table, such that a portion of each tip element is disposed just beyond the periphery of the wafer;
interrupting or terminating the application of the negative pressure to the underside of the wafer; and
activating a set of ejector pins corresponding to the wafer table in an upward direction to elevate the wafer away from the wafer table surface.

15. The method of claim 10, wherein automatically preventing uncontrolled lateral displacement of the wafer relative to the wafer table surface comprises:
interrupting or terminating the application of the negative pressure to the underside of the wafer;
applying an air puff to the underside of the wafer essentially immediately after interruption or cessation of the application of the negative pressure to the underside of the wafer, the air puff applied from an air puff onset time to an air puff cessation time; and
activating a set of ejector pins corresponding to the vacuum table to displace the set of ejector pins in an upward direction after a very brief ejector pin activation delay time following the air puff onset time to thereby lift the wafer off of the wafer table surface with minimal or negligible lateral displacement as a result of the very brief ejector pin activation delay time relative to the air puff onset time, wherein the ejector pin activation delay time is precisely controlled relative to the air puff onset time such that the wafer is vertically raised away from the wafer table surface synchronous with the release of the wafer from the wafer table surface in response to the air puff.

16. The method of claim 15, wherein the ejector pin activation delay time is experimentally determined.

17. The method of claim 15, wherein the ejector pin activation delay time is between 5-50 msec.

18. A method for handling a wafer in association with an inspection process, comprising:
retrieving the wafer from a wafer source;
transporting the wafer to a wafer prealigner;
disposing the wafer on a wafer table surface provided by a wafer table following prealignment of the wafer;
applying a negative pressure to an underside of the wafer;
automatically remediating insufficient retention of the wafer upon the wafer table surface due to wafer warpage or non-planarity by way of:
detecting whether the wafer is securely retained upon the wafer table surface prior to the initiation of the inspection process; and
automatically applying a downward force to portions of the wafer until secure retention of the wafer upon the wafer table surface is detected; and
automatically preventing uncontrolled lateral displacement of the wafer along the wafer table surface following the inspection process as a result of cessation of the application of the negative pressure to the wafer by way of:
(a) automatically confining the wafer to reside within a confinement position on the wafer table; or
(b) coordinating the cessation of the application of the negative pressure to the underside of the wafer with an application of an air puff to the underside of the wafer and an activation of a set of ejector pins that is vertically displaceable relative to the wafer table surface, such that the wafer is vertically raised away from the wafer table surface synchronous with the release of the wafer from the wafer table surface in response to the air puff;
and
retrieving the wafer from the wafer table and transferring the wafer to a wafer destination.

* * * * *